US010201619B2

(12) United States Patent
Chen et al.

(10) Patent No.: US 10,201,619 B2
(45) Date of Patent: Feb. 12, 2019

(54) REGENERATING FUNCTIONAL NEURONS FOR TREATMENT OF DISEASE AND INJURY IN THE NERVOUS SYSTEM

(71) Applicant: The Penn State Research Foundation, University Park, PA (US)

(72) Inventors: Gong Chen, State College, PA (US); Lei Zhang, State College, PA (US); Zheng Wu, State College, PA (US); Yuchen Chen, State College, PA (US); Fan Wang, State College, PA (US); Ziyuan Guo, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 15 days.

(21) Appl. No.: 15/643,186

(22) Filed: Jul. 6, 2017

(65) Prior Publication Data

US 2017/0304463 A1    Oct. 26, 2017

Related U.S. Application Data

(63) Continuation of application No. 14/438,765, filed as application No. PCT/US2013/051277 on Jul. 19, 2013, now Pat. No. 9,717,804.

(60) Provisional application No. 61/762,506, filed on Feb. 8, 2013, provisional application No. 61/673,471, filed on Jul. 19, 2012.

(51) Int. Cl.
*A61K 48/00* (2006.01)
*C12N 15/86* (2006.01)
*A61K 38/17* (2006.01)

(52) U.S. Cl.
CPC ........ *A61K 48/005* (2013.01); *A61K 38/1709* (2013.01); *C12N 15/86* (2013.01); *A01K 2227/105* (2013.01); *A01K 2267/0356* (2013.01); *C12N 2740/13043* (2013.01)

(58) Field of Classification Search
None
See application file for complete search history.

(56) References Cited

U.S. PATENT DOCUMENTS

| | | | |
|---|---|---|---|
| 5,695,995 | A | 12/1997 | Weintraub et al. |
| 6,444,463 | B1 | 9/2002 | Tapscott |
| 7,041,507 | B1 | 5/2006 | Levesque et al. |
| 9,717,804 | B2 * | 8/2017 | Chen ............... A61K 48/005 |
| 2013/0022583 | A1 | 1/2013 | Wernig et al. |

FOREIGN PATENT DOCUMENTS

| WO | WO-2011050476 | 5/2011 |
|---|---|---|
| WO | WO-2011097181 | 8/2011 |
| WO | WO-2012010675 | 1/2012 |

OTHER PUBLICATIONS

Richardson et al, Neuron 2011;70:661-73. (Year: 2011).*
Cho, J. et al., The Role of BETA2/NeuroD1 in the Development of the Nervous System, *Molecular Neurobiology*, 30(1): 35-47, 2004.
Escartin, C. et al., Targeted Activation of Astrocytes: A Potential Neuroprotective Strategy, *Mol Neurobiol*, 38: 231-241, 2008.
Gao, Z. et al., Neurod1 is essential for the survival and maturation of adult-born neurons, 12(9): 1090-1092, Sep. 2009.
Kitagawa, (Rinsho Shinkelgaku) 44: 756-9, 2004 (Abstract).
Roybon, L. et al., Neurogenin2 Directs Granule Neuroblast Production and Amplification While NeuroD1 Specifies Neuronal Fate During Hippocampal Neurogenesis, Plos One, 4(3): 1-19, Mar. 10, 2009.
Torper, O. et al., Generation of induced neurons via direct conversion in vivo, PNAS Early Edition, Mar. 25, 2013.
Zhao, J. et al., Neuronal Transcription Factors Induce Conversion of Human Glioma Cells to Neurons and Inhibit Tumorigenesis, *PLoS One*, 7(7): 1-11, Jul. 31, 2012.
Gallo, V. et al., Glial Development: The Crossroads of Regeneration and Repair in the CNS, *Neuron*, 83: 285-308, Jul. 16, 2014.
Guo, Z. et al., In Vivo Direct Reprogramming of Reactive Glial Cells into Functional Neurons after Brain Injury and in an Alzheimer's Disease Model, *Cell Stem Cell*, 14: 188-202, Feb. 6, 2014.
Lu, J. et al., Turning Reactive Glia into Functional Neurons in the Brain, *Cell Stem Cell*, 14: 133-34, Feb. 6, 2014.
Yang, N. et al., Induced Neuronal Cells: How to Make and Define a Neuron, Cell Stem Cell, 9: 517-525, Dec. 2, 2011.
Richardson, R. et al., Future Applications: Gene Therapy, Neurosurgery Clinics of North America, 20: 219-224, 2009.
Lee, J. et al., Conversion of Xenopus Ectoderm into Neurons by NeuroD, a Basic Helix-Loop-Helix Protein, Science, 268: 836-44, May 12, 1995.
Fang Hongbo, The Molecular Mechanism of the NeuroD1 Gene Regulation Induced by All-trans Retinoic Acid in Neural Cells Differentiation, China Doctor Dissertation Full-text Database (Electronic Journal) Basic Science vol. No. 11, pp. A006-4, published on Nov. 15, 2011.
English abstract of Fang Hongbo, The Molecular Mechanism of the NeuroDI Gene Regulation Induced by All-trans Retinoic Acid in Neural Cells Differentiation, China Doctor Dissertation Full-text Database (Electronic Journal) Basic Science vol. No. 11, pp. A006-4, published on Nov. 15, 2011.

(Continued)

*Primary Examiner* — Qian Janice Li
(74) *Attorney, Agent, or Firm* — Dinsmore & Shohl LLP

(57) ABSTRACT

Methods for producing new neurons in the brain in vivo are provided according to aspects of the present invention which include introducing NeuroD1 into a glial cell, particularly into a reactive astrocyte or NG2 cell, thereby "converting" the reactive glial cell to a neuron. Methods of producing a neuronal phenotype in a glial cell are provided according to aspects of the present invention which include expressing exogenous NeuroD1 in the glial cell, wherein expressing exogenous NeuroD1 includes delivering an expression vector, such as a viral expression vector, including a nucleic acid encoding the exogenous NeuroD1 to the glial cell.

19 Claims, 42 Drawing Sheets

Specification includes a Sequence Listing.

(56) References Cited

OTHER PUBLICATIONS

Chinese Application No. 201380048924.2, Office Action dated Mar. 21, 2017, Chinese Language.
Chinese Application No. 201380048924.2, Office Action dated Mar. 21, 2017, English Language.
Chinese Application No. 201380048924.2, Office Action dated Jun. 17, 2016, Chinese Language.
Chinese Application No. 201380048924.2, Office Action dated Jun. 17, 2016, English Language.
Yokoyama, M. et al., Molecular cloning of a human neuroD from a neuroblastoma cell line specifically expressed in the fetal brain and adult cerebellum, Molecular Brain Research, 42: 135-139, 1996.

* cited by examiner

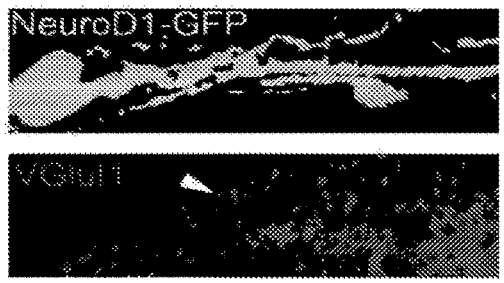
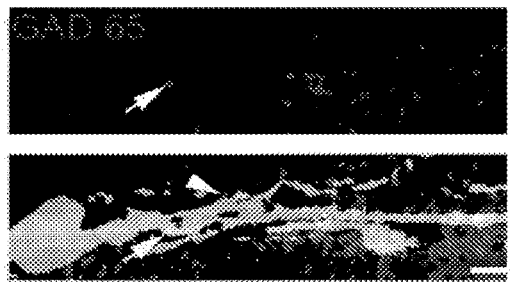
FIG.3D          FIG.3E
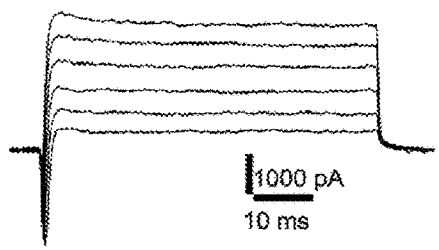
FIG.3F          FIG.3H
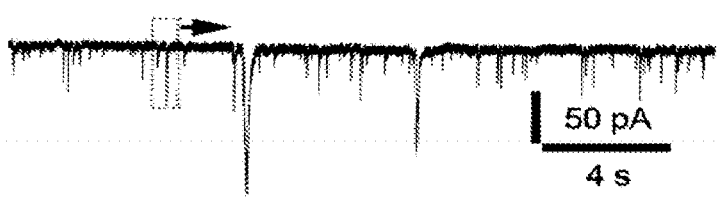
FIG.3G

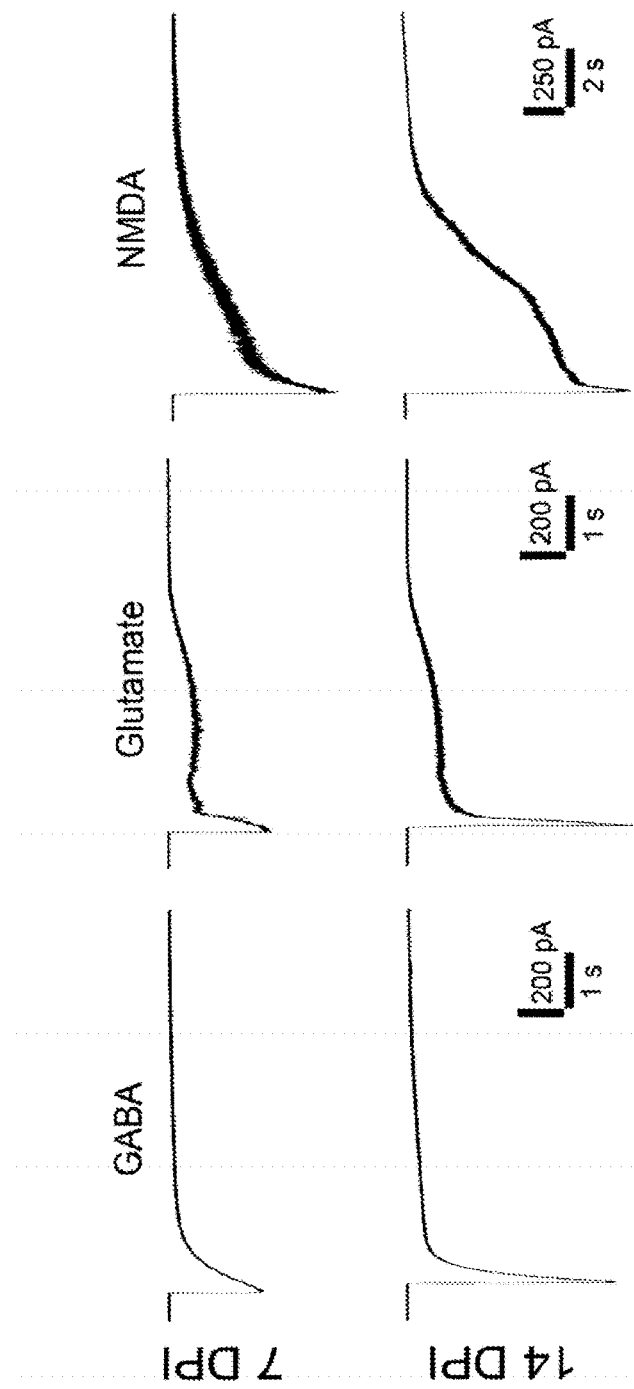
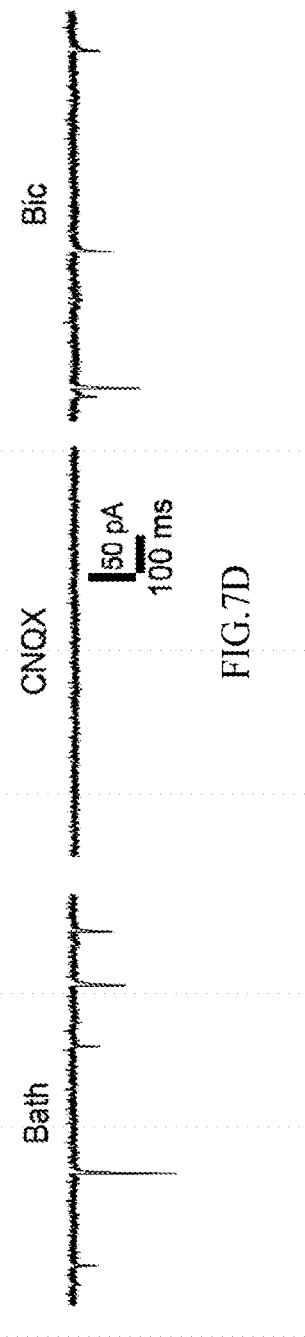
FIG. 7A  FIG. 7B  FIG. 7C  FIG. 7D

CNQX

Bic

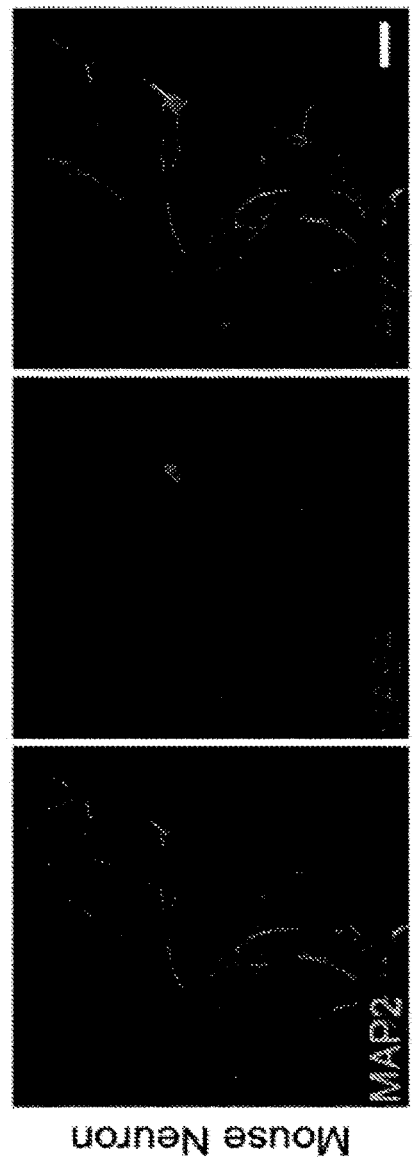
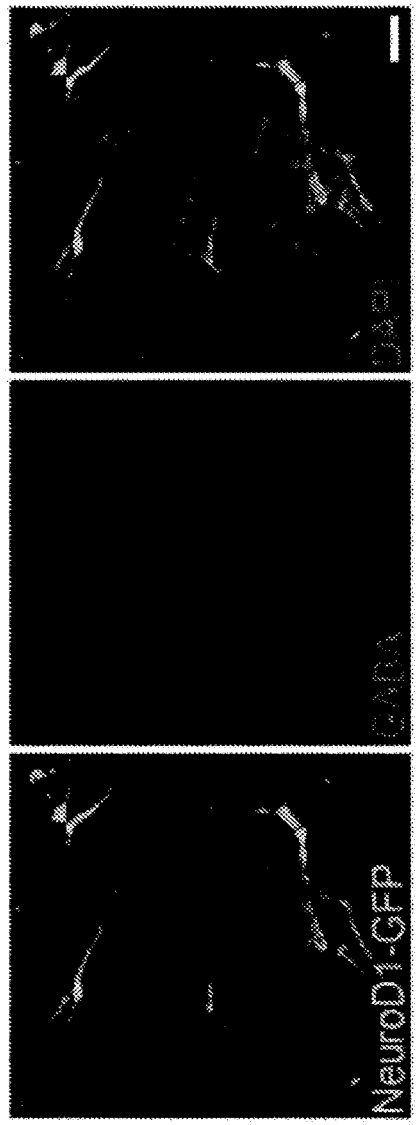
FIG. 17C
FIG. 17D

SEQUENCE LISTING

<160> NUMBER OF SEQ ID NOS: 9

<210> SEQ ID NO 1
<211> LENGTH: 1071
<212> TYPE: DNA
<213> ORGANISM: Homo sapiens

<400> SEQUENCE: 1

```
atgaccaaat cgtacagcga gagtgggctg atgggcgagc ctcagcccca aggtcctcca      60
agctggacag acgagtgtct cagttctcag gacgaggagc acgaggcaga caagaaggag     120
gacgacctcg aagccatgaa cgcagaggag gactcactga ggaacggggg agaggaggag     180
gacgaagatg aggacctgga agaggaggaa gaagaggaag aggaggatga cgatcaaaag     240
cccaagagac gcggccccaa aaagaagaag atgactaagg ctcgcctgga gcgttttaaa     300
ttgagacgca tgaaggctaa cgcccgggag cggaaccgca tgcacggact gaacgcggcg     360
ctagacaacc tgcgcaaggt ggtgccttgc tattctaaga cgcagaagct gtccaaaatc     420
gagactctgc gcttggccaa gaactacatc tgggctctgt cggagatcct gcgctcaggc     480
aaaagcccag acctggtctc cttcgttcag acgctttgca agggcttatc caacccacc      540
accaacctgg ttgcgggctg cctgcaactc aatcctcgga cttttctgcc tgagcagaac     600
caggacatgc cccccacct gccgacggcc agcgcttcct ccctgtaca ccctactcc       660
taccagtcgc ctgggctgcc cagtccgcct acggtacca tggacagctc ccatgtcttc     720
cacgttaagc ctccgccgca cgcctacagc gcagcgctgg agcccttctt tgaaagccct     780
ctgactgatt gcaccagccc ttcctttgat ggacccctca gcccgccgct cagcatcaat     840
ggcaacttct ctttcaaaca cgaaccgtcc gccgagtttg agaaaaatta tgcctttacc     900
atgcactatc ctgcagcgac actggcaggg gcccaaagcc acggatcaat cttctcaggc     960
accgctgccc ctcgctgcga gatccccata gacaatatta tgtccttcga tagccattca    1020
catcatgagc gagtcatgag tgcccagctc aatgccatat ttcatgatta g              1071
```

<210> SEQ ID NO 2
<211> LENGTH: 356
<212> TYPE: PRT
<213> ORGANISM: Homo sapiens

<400> SEQUENCE: 2

```
Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Leu Glu Ala Met Asn Ala
        35                  40                  45

Glu Glu Asp Ser Leu Arg Asn Gly Gly Glu Glu Asp Glu Asp
    50                  55                  60

Asp Leu Glu Glu Glu Glu Glu Glu Glu Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175
```

```
Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
            245                 250                 255

Phe Glu Ser Pro Leu Thr Asp Cys Thr Ser Pro Ser Phe Asp Gly Pro
        260                 265                 270

Leu Ser Pro Pro Leu Ser Ile Asn Gly Asn Phe Ser Phe Lys His Glu
    275                 280                 285

Pro Ser Ala Glu Phe Glu Lys Asn Tyr Ala Phe Thr Met His Tyr Pro
290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
            325                 330                 335

Asp Ser His Ser His His Glu Arg Val Met Ser Ala Gln Leu Asn Ala
        340                 345                 350

Ile Phe His Asp
        355

<210> SEQ ID NO 3
<211> LENGTH: 1074
<212> TYPE: DNA
<213> ORGANISM: Mus musculus

<400> SEQUENCE: 3
atgaccaaat catacagcga gagcgggctg atgggcgagc ctcagcccca aggtccccca      60
agctggacag atgagtgtct cagttctcag gacgaggaac acgaggcaga caagaaagag     120
gacgagcttg aagccatgaa tgcagaggag gactctctga aaacgggggg agaggaggag     180
gaggaagatg aggatctaga ggaagaggag gaagaagaag aggaggagga ggatcaaaag     240
cccaagagac ggggtcccaa aaagaaaaag atgaccaagg cgcgcctaga cgttttaaa     300 ttaaggcgca tgaaggccaa cgcccgcgag cggaaccgca tgcacgggct gaacgcggcg     360
ctggacaacc tgcgcaaggt ggtaccttgc tactccaaga cccagaaact gtctaaaata     420
gagacactgc gcttggccaa gaactacatc tgggctctgt cagagatcct gcgctcaggc     480
aaaagccctg atctggtctc cttcgtacag acgctctgca aggtttgtc ccagcccact     540 accaatttgg tcgccggctg cctgcagctc aaccctcgga cttttcttgcc tgagcagaac     600 ccggacatgc cccgcatct gccaaccgcc agcgcttcct tcccggtgca tccctactcc     660
taccagtccc ctggactgcc cagcccgccc tacggcacca tggacagctc ccacgtcttc     720
cacgtcaagc cgccgccaca cgcctacagc gcagctctgg agcccttctt tgaaagcccc     780
ctaactgact gcaccagccc ttcctttgac ggacccctca gccgccgct cagcatcaat     840 ggcaacttct ctttcaaaca cgaaccatcc gccgagtttg aaaaaaatta tgcctttacc     900
atgcactacc ctgcagcgac gctggcaggg ccccaaagcc acggatcaat cttctcttcc     960
ggtgccgctg cccctcgctg cgagatcccc atagacaaca ttatgtcttt cgatagccat    1020
```
tcgcatcatg agcgagtcat gagtgcccag cttaatgcca tctttcacga ttag 1074

<210> SEQ ID NO 4
<211> LENGTH: 357
<212> TYPE: PRT
<213> ORGANISM: Mus musculus

<400> SEQUENCE: 4

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Glu Leu Glu Ala Met Asn Ala
        35                  40                  45

Glu Glu Asp Ser Leu Arg Asn Gly Gly Glu Glu Glu Glu Glu Asp Glu
    50                  55                  60

Asp Leu Glu Glu Glu Glu Glu Glu Glu Glu Glu Glu Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Pro Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Pro Gln Ser His Gly Ser Ile Phe Ser Ser
305                 310                 315                 320

Gly Ala Ala Ala Pro Arg Cys Glu Ile Pro Ile Asp Asn Ile Met Ser
                325                 330                 335

Phe Asp Ser His Ser His His Glu Arg Val Met Ser Ala Gln Leu Asn
            340                 345                 350

Ala Ile Phe His Asp
        355

<210> SEQ ID NO 5
<211> LENGTH: 1053
<212> TYPE: DNA
<213> ORGANISM: Mus musculus

<400> SEQUENCE: 5

| | | | | | |
|---|---|---|---|---|---|
| gcagtgtgga | gacacaccca | ctttccccaa | gggctcctgc | tcccccaagt | gatcccctta | 60 |
| tcctccgtgc | taagatgaca | ccgaggttgc | agtccttacc | tttgaaagca | gccacaaggg | 120 |
| cgtggggggtg | cacaccttta | atcccagcac | tcgggaggca | gaggcaggca | gatttctgag | 180 |
| ttcgagacca | gcctggtcta | caaagtgaat | tccaggacag | ccagggctat | acagagaaac | 240 |
| cctgtcttga | aaaaaaaga | gaaagaaaaa | agaaaaaaaa | aatgaaagc | agccacatct | 300 |
| aaggactacg | tggcacagga | gagggtgagt | ccctgagagt | tcagctgctg | ccctgtctgt | 360 |
| tcctgtaaat | ggcagtgggg | tcatgggaaa | gtgaaggggc | tcaaggtatt | ggacacttcc | 420 |
| aggataatct | tttggacgcc | tcaccctgtg | ccaggaccaa | ggctgagctt | ggcaggctca | 480 |
| gaacagggtg | tcctgttctt | ccctgtctaa | acattcact | ctcagcttgc | tcacccttcc | 540 |
| ccagacaagg | aagctgcaca | gggtctggtg | ttcagatggc | tttggcttac | agcaggtgtg | 600 |
| ggtgtggggt | aggaggcagg | gggtaggggt | ggggaagcc | tgtactatac | tcactatcct | 660 |
| gtttctgacc | ctctaggact | cctacagggt | tatgggagtg | acaggcagt | ccagatctga | 720 |
| gctgctgacc | cacaagcagt | gccctgtgcc | tgccagaatc | caaagccctg | ggaatgtccc | 780 |
| tctggtcccc | ctctgtcccc | tgcagcccttt | cctgttgctc | aaccttgcac | agttccgacc | 840 |
| tgggggagag | agggacagaa | atcttgccaa | gtatttcaac | agaatgtact | ggcaattact | 900 |
| tcatggcttc | ctggacttgg | taaaggatgg | actaccccgc | ccaacagggg | ggctggcagc | 960 |
| caggtaggcc | cataaaaagc | ccgctgggga | gtcctcctca | ctctctgctc | ttcctcctcc | 1020 |
| agcacacatc | agacctagta | gctgtggaaa | cca | | | 1053 |

<210> SEQ ID NO 6
<211> LENGTH: 1672
<212> TYPE: DNA
<213> ORGANISM: Homo sapiens

<400> SEQUENCE: 6

| | | | | | |
|---|---|---|---|---|---|
| gtctgcaagc | agacctggca | gcattgggct | ggccgccccc | cagggcctcc | tcttcatgcc | 60 |
| cagtgaatga | ctcaccttgg | cacagacaca | atgttcgggg | tgggcacagt | gcctgcttcc | 120 |
| cgccgcaccc | cagcccccct | caaatgcctt | ccgagaagcc | cattgagtag | ggggcttgca | 180 |
| ttgcacccca | gcctgacagc | ctggcatctt | gggataaaag | cagcacagcc | cctaggggc | 240 |
| tgcccttgct | gtgtggcgcc | accgcggtg | gagaacaagg | ctctattcag | cctgtgccca | 300 |
| ggaaagggga | tcagggggatg | cccaggcatg | gacagtgggt | ggcaggggg | gagaggaggg | 360 |
| ctgtctgctt | cccagaagtc | caaggacaca | aatgggtgag | gggactgggc | agggttctga | 420 |
| ccctgtggga | ccagagtgga | gggcgtagat | ggacctgaag | tctccaggga | caacagggcc | 480 |
| caggtctcag | gctcctagtt | gggcccagtg | gctccagcgt | ttccaaaccc | atccatcccc | 540 |
| agaggttctt | cccatctctc | caggctgatg | tgtgggaact | cgaggaaata | aatctccagt | 600 |
| gggagacgga | ggggtggcca | gggaaacggg | gcgctgcagg | aataaagacg | agccagcaca | 660 |
| gccagctcat | gcgtaacggc | tttgtggagc | tgtcaaggcc | tggtctctgg | gagagaggca | 720 |
| cagggagggcc | agacaaggaa | ggggtgacct | ggagggacag | atccagggc | taagtcctg | 780 |
| ataaggcaag | agagtgccgg | cccccctcttg | ccctatcagg | acctccactg | ccacatagag | 840 |

| | |
|---|---|
| gccatgattg acccttagac aaagggctgg tgtccaatcc cagcccccag ccccagaact | 900 |
| ccagggaatg aatgggcaga gagcaggaat gtgggacatc tgtgttcaag gaaggactc | 960 |
| caggagtctg ctgggaatga ggcctagtag gaaatgaggt ggcccttgag ggtacagaac | 1020 |
| aggttcattc ttcgccaaat tcccagcacc ttgcaggcac ttacagctga gtgagataat | 1080 |
| gcctgggtta tgaaatcaaa aagttggaaa gcaggtcaga ggtcatctgg tacagccctt | 1140 |
| ccttcccttt ttttttttt tttttgtga gacaaggtct ctctctgttg cccaggctgg | 1200 |
| agtggcgcaa acacagctca ctgcagcctc aacctactgg gctcaagcaa tcctccagcc | 1260 |
| tcagcctccc aaagtgctgg gattacaagc atgagccacc ccactcagcc ctttccttcc | 1320 |
| tttttaattg atgcataata attgtaagta ttcatcatgg tccaaccaac cctttcttga | 1380 |
| cccaccttcc tagagagagg gtcctcttga ttcagcggtc agggcccag acccatggtc | 1440 |
| tggctccagg taccacctgc ctcatgcagg agttggcgtg cccaggaagc tctgcctctg | 1500 |
| ggcacagtga cctcagtggg gtgaggggag ctctccccat agctgggctg cggcccaacc | 1560 |
| ccacccctc aggctatgcc aggggtgtt gccagggca cccgggcatc gccagtctag | 1620 |
| cccactcctt cataaagccc tcgcatccca ggagcgagca gagccagagc at | 1672 |

<210> SEQ ID NO 7
<211> LENGTH: 1610
<212> TYPE: DNA
<213> ORGANISM: Mus musculus

<400> SEQUENCE: 7

| | |
|---|---|
| aactgagagt ggaggggcac agaagagccc aagaggctcc ttaggttgtg tggagggtac | 60 |
| aatatgtttg ggctgagcaa cccagagcca gactttgtct ggctggtaag agacagaggt | 120 |
| gcctgctatc acaatccaag ggtctgcttg aggcagagcc agtgcaaagg atgtggttag | 180 |
| agccagcctg gtgtactgaa gaggggcgaa gagcttgagt aaggagtctc agcggtggtt | 240 |
| tgagaggcag ggtggttaat ggagtagctg caggggagaa tccttgggag ggagcctgca | 300 |
| ggacagagct ttggtcagga agtgatgggc atgtcactgg accctgtatt gtctctgact | 360 |
| tttctcaagt aggacaatga ctctgcccag ggaggggtc tgtgacaagg tggaagggcc | 420 |
| agaggagaac ttctgagaag aaaaccagag gccgtgaaga ggtgggaagg gcatgggatt | 480 |
| cagaacctca ggcccaccag gacacaaccc caggtccaca gcagatgggt gaccttgcat | 540 |
| gtctcagtca ccagcattgt gctccttgct tatcacgctt gggtgaagga aatgacccaa | 600 |
| atagcataaa gcctgaaggc cgggactagg ccagctaggg cttgcccttc ccttcccagc | 660 |
| tgcactttcc ataggtccca ccttcagcag attagacccg cctcctgctt cctgcctcct | 720 |
| tgcctcctca ctcatgggtc tatgcccacc tccagtctcg ggactgaggc tcactgaagt | 780 |
| cccatcgagg tctggtctgg tgaatcagcg gctggctctg ggccctgggc gaccagttag | 840 |
| gttccgggca tgctaggcaa tgaactctac ccggaattgg gggtgcgggg aggcggggag | 900 |
| gtctccaacc cagccttttg aggacgtgcc tgtcgctgca cggtgctttt tatagacgat | 960 |
| ggtggcccat tttgcagaag ggaaagccgg agccctctgg ggagcaaggt ccccgcaaat | 1020 |
| ggacggatga cctgagcttg gttctgccag tccacttccc aaatccctca ccccattcta | 1080 |
| gggactaggg aaagatctcc tgattggtca tatctggggg cctggccgga gggcctccta | 1140 |
| tgattggaga gatctaggct gggcgggccc tagagcccgc ctcttctctg cctggaggag | 1200 |
| gagcactgac cctaacccctc tctgcacaag acccgagctt gtgcgccctt ctgggagctt | 1260 |

```
gctgcccctg tgctgactgc tgacagctga ctgacgctcg cagctagcag gtacttctgg    1320
gttgctagcc cagagccctg ggccggtgac cctgttttcc ctacttcccg tctttgacct    1380
tgggtaagtt tcttttttctt ttgtttttga gagaggcacc cagatcctct ccactacagg    1440
cagccgctga accttggatc ctcagctcct gccctgggaa ctacagttcc tgccctttttt    1500 ttcccacctt gagggaggtt ttccctgagt agcttcgact atcctggaac aagctttgta    1560
gaccagcctg ggtctccgga gagttgggat taaaggcgtg caccaccacc                1610
```

```
<210> SEQ ID NO 8
<211> LENGTH: 1387
<212> TYPE: DNA
<213> ORGANISM: Homo sapiens

<400> SEQUENCE: 8
ctctggtttc aagaccaata ctcataaccc ccacatggac caggcaccat cacacctgag     60
cactgcactt agggtcaaag acctggcccc acatctcagc agctatgtag actagctcca   120
gtcccttaat ctctctcagc ctcagtttct tcatctgcaa aacaggtctc agtttcgttg    180
caaagtatga agtgctgggc tgttactggt caaagggaag agctgggaag agggtgcaag   240
gtggggttgg gctggagatg ggctggagca gatagatgga gggacctgaa tggaggaagt   300
aaaccaaggc ccgtaacat tgggactgga cagagaacac gcagatcctc taggcaccgg    360
aagctaagta acattgccct ttctcctcct gtttgggact aggctgatgt tgctgcctgg    420
aagggagcca gcagaagggc cccagcctga agctgttagg tagaagccaa atccagggcc   480
agatttccag gaggcagcct cgggaagttg aaacacccgg attcagggt caggaggcct    540 gggcttctgg caccaaacgg ccagggacct actttccacc tggagtcttg taagagccac   600
tttcagcttg agctgcactt tcgtcctcca tgaaatgggg gaggggatgc tcctcaccca   660
ccttgcaagg ttattttgag gcaaatgtca tggcgggact gagaattctt ctgccctgcg   720
aggaaatcca gacatctctc ccttacagac agggagactg aggtgaggcc cttccaggca   780
gagaaggtca ctgttgcagc catgggcagt gccccacagg acctcgggtg gtgcctctgg   840
agtctggaga agttcctagg ggacctccga ggcaaagcag cccaaaagcc gcctgtgagg   900
gtggctggtg tctgtccttc ctcctaaggc tggagtgtgc ctgtggaggg gtctcctgaa   960
ctcccgcaaa ggcagaaagg agggaagtag gggctgggac agttcatgcc tcctcccctga  1020 gggggtctcc cgggctcggc tcttggggcc agagttcagg gtgtctgggc ctctctatga  1080
ctttgttcta agtctttagg gtggggctgg ggtctggccc agctgcaagg gccccctcac  1140
ccctgcccca gagaggaaca gccccgcacg ggcccttttaa gaaggttgag ggtgggggca  1200
ggtgggggag tccaagcctg aaacccgagc gggcgcgcgg gtctgcgcct gccccgcccc  1260
cggagttaag tgcgcggaca cccggagccg gcccgcgccc aggagcagag ccgcgctcgc  1320
tccactcagc tcccagctcc caggactccg ctggctcctc gcaagtcctg ccgcccagcc  1380
cgccggg                                                              1387
```

```
<210> SEQ ID NO 9
<211> LENGTH: 9232
<212> TYPE: DNA
<213> ORGANISM: Artificial Sequence
<220> FEATURE:
<223> OTHER INFORMATION: Expression cassette including CAG promoter,
      woodchuck hepatitis virus posttranscriptional regulatory element
      (WPRE), and nucleic acid encoding NeuroD1 and eGFP separated by
      IRES
```

<400> SEQUENCE: 9

```
gatccggcca ttagccatat tattcattgg ttatatagca taaatcaata ttggctattg      60
gccattgcat acgttgtatc catatcataa tatgtacatt tatattggct catgtccaac     120
attaccgcca tgttgacatt gattattgac tagttattaa tagtaatcaa ttacggggtc     180
attagttcat agcccatata tggagttccg cgttacataa cttacggtaa atggcccgcc     240
tggctgaccg cccaacgacc cccgcccatt gacgtcaata atgacgtatg ttcccatagt     300
aacgccaata gggactttcc attgacgtca atgggtggag tatttacggt aaactgccca     360
cttggcagta catcaagtgt atcatatgcc aagtacgccc cctattgacg tcaatgacgg     420
taaatggccc gcctggcatt atgcccagta catgacctta tgggactttc ctacttggca     480
gtacatctac gtattagtca tcgctattac catggtgatg cggttttggc agtacatcaa     540
tgggcgtgga tagcggtttg actcacgggg atttccaagt ctccacccca ttgacgtcaa     600
tgggagtttg ttttggcacc aaaatcaacg ggactttcca aaatgtcgta acaactccgc     660
cccattgacg caaatgggcg gtaggcatgt acggtgggag gtctatataa gcagagctca     720
ataaaagagc ccacaacccc tcactcgggg cgccagtcct ccgattgact gagtcgcccg     780
ggtacccgta ttcccaataa agcctcttgc tgtttgcatc cgaatcgtgg tctcgctgtt     840
ccttgggagg gtctcctctg agtgattgac tacccacgac ggggtctttt catttggggg     900
ctcgtccgga atttggagac ccctgcccag ggaccaccga cccaccaccg ggaggtaagc     960
tggccagcaa cttatctgtg tctgtccgat tgtctagtgt ctatgtttga tgttatgcgc    1020
ctgcgtctgt actagttagc taactagctc tgtatctggc ggacccgtgg tggaactgac    1080
gagttctgaa cacccggccg caaccctggg agacgtccca gggactttgg gggccgtttt    1140
tgtggcccga cctgaggaag ggagtcgatg tggaatccga cccgtcagg atatgtggtt     1200
ctggtaggag acgagaacct aaaacagttc ccgcctccgt ctgaattttt gctttcggtt    1260
tggaaccgaa gccgcgcgtc ttgtctgctg cagcgctgca gcatcgttct gtgttgtctc    1320
tgtctgactg tgtttctgta tttgtctgaa aattagggcc agactgttac cactccctta    1380
agtttgacct taggtcactg gaaagatgtc gagcggatcg ctcacaacca gtcggtagat    1440
gtcaagaaga gacgttgggt taccttctgc tctgcagaat ggccaacctt taacgtcgga    1500
tggccgcgag acggcacctt taaccgagac ctcatcaccc aggttaagat caaggtcttt    1560
tcacctggcc cgcatggaca cccagaccag gtcccctaca tcgtgacctg ggaagccttg    1620
gcttttgacc cccctccctg ggtcaagccc tttgtacacc ctaagcctcc gcctcctctt    1680
cctccatccg ccccgtctct ccccccttgaa cctcctcgtt cgaccccgcc tcgatcctcc    1740
ctttatccag ccctcactcc ttctctaggc gccggaattc gatgtcgaca ttgattattg    1800
actagttatt aatagtaatc aattacgggg tcattagttc atagcccata tatggagttc    1860
cgcgttacat aacttacggt aaatggcccg cctggctgac cgcccaacga ccccgccca    1920
ttgacgtcaa taatgacgta tgttcccata gtaacgccaa tagggacttt ccattgacgt    1980
caatgggtgg actatttacg gtaaactgcc cacttggcag tacatcaagt gtatcatatg    2040
ccaagtacgc cccctattga cgtcaatgac ggtaaatggc ccgcctggca ttatgcccag    2100
tacatgacct tatgggactt tcctacttgg cagtacatct acgtattagt catcgctatt    2160
accatgggtc gaggtgagcc ccacgttctg cttcactctc cccatctccc ccccctcccc    2220
accccccaatt ttgtatttat ttattttta attatttttgt gcagcgatgg gggcgggggg    2280
ggggggggcg cgcgccaggc ggggcggggc ggggcgaggg gcggggcggg gcgaggcgga    2340
```

-continued

```
gaggtgcggc ggcagccaat cagagcggcg cgctccgaaa gtttcctttt atggcgaggc    2400
ggcggcggcg gcggccctat aaaaagcgaa gcgcgcggcg ggcgggagtc gctgcgttgc    2460
cttcgccccg tgccccgctc cgcgccgcct cgcgccgccc gccccggctc tgactgaccg    2520
cgttactccc acaggtgagc gggcgggacg gcccttctcc tccgggctgt aattagcgct    2580
tggtttaatg acggctcgtt tcttttctgt ggctgcgtga agccttaaa gggctccggg     2640 agggcccttt gtgcgggggg gagcggctcg ggggtgcgt gcgtgtgtgt gtgcgtgggg     2700
agcgccgcgt gcggcccgcg ctgcccggcg gctgtgagcg ctgcgggcgc ggcgcggggc    2760
tttgtgcgct ccgcgtgtgc gcgaggggag gcggccggg ggcggtgccc cgcggtgcgg     2820
gggggctgcg aggggaacaa aggctgcgtg cggggtgtgt gcgtgggggg gtgagcaggg    2880
ggtgtgggcg cggcggtcgg gctgtaaccc ccccctgcac ccccctcccc gagttgctga    2940
gcacggcccg gcttcgggtg cggggctccg tgcggggcgt ggcgcggggc tcgccgtgcc    3000 gggcggggg tggcggcagg tgggggtgcc gggcggggcg gggccgcctc gggccggga     3060 gggctcgggg gaggggcgcg gcggcccgg agcgccggcg gctgtcgagg cgcggcgagc     3120
cgcagccatt gccttttatg gtaatcgtgc gagagggcgc agggacttcc tttgtcccaa    3180
atctggcgga gccgaaatct gggaggcgcc gccgcacccc ctctagcggg cgcgggcgaa    3240
gcggtgcggc gccggcagga aggaaatggg cgggagggc cttcgtgcgt cgccgcgccg     3300
ccgtcccctt ctccatctcc agcctcgggg ctgccgcagg gggacggctg ccttcggggg    3360
ggacggggca gggcggggtt cggcttctgg cgtgtgaccg gcggctctag agcctctgct    3420
aaccatgttc atgccttctt ctttttccta cagctcctgg gcaacgtgct ggttgttgtg    3480
ctgtctcatc attttggcaa agaattcgct agcggatccg gccgcctcgg ccaccggtcg    3540
ccaccatcgc caccatgacc aaatcataca gcgagagcgg gctgatgggc gagcctcagc    3600
cccaaggtcc cccaagctgg acagatgagt gtctcagttc tcaggacgag gaacacgagg    3660
cagacaagaa agaggacgag cttgaagcca tgaatgcaga ggaggactct ctgagaaacg    3720
ggggagagga ggaggaggaa gatgaggatc tagaggaaga ggaggaagaa gaagaggagg    3780
aggaggatca aaagcccaag agacggggtc ccaaaaagaa aaagatgacc aaggcgcgcc    3840
tagaacgttt taaattaagg cgcatgaagg ccaacgcccg cgagcggaac cgcatgcacg    3900
ggctgaacgc ggcgctggac aacctgcgca aggtggtacc ttgctactcc aagacccaga    3960
aactgtctaa aatagagaca ctgcgcttgg ccaagaacta catctgggct ctgtcagaga    4020
tcctgcgctc aggcaaaagc cctgatctgg tctccttcgt acagacgctc tgcaaaggtt    4080
tgtcccagcc cactaccaat ttggtcgccg gctgctgca gctcaaccct cggactttct    4140
tgcctgagca gaacccggac atgccccgc atctgccaac cgccagcgct tccttcccgg    4200
tgcatcccta ctcctaccag tcccctggac tgcccagccc gcctacggc accatggaca    4260 gctcccacgt cttccacgtc aagcgccgc acacgcctta cagcgcagct ctggagccct    4320
tctttgaaag cccctaact gactgcacca gcccttcctt tgacggaccc ctcagcccgc     4380
cgctcagcat caatggcaac ttctctttca acacgaacc atccgccgag tttgaaaaaa    4440
attatgcctt taccatgcac tacctgcag cgacgctggc agggccccaa agccacggat     4500
caatcttctc ttccggtgcc gctgccctc gctgcgagat cccatagac aacattatgt      4560 ctttcgatag ccattcgcat catgagcgag tcatgagtgc ccagcttaat gccatctttc    4620
acgattaggt ttaaacgcgg ccgcgcccct ctccctcccc cccccctaac gttactggcc    4680
```

```
gaagccgctt ggaataaggc cggtgtgcgt tgtctatat gttattttcc accatattgc      4740
cgtcttttgg caatgtgagg gcccggaaac ctggccctgt cttcttgacg agcattccta      4800
ggggtctttc ccctctcgcc aaaggaatgc aaggtctgtt gaatgtcgtg aaggaagcag      4860
ttcctctgga agcttcttga agacaaacaa cgtctgtagc gacccttttgc aggcagcgga     4920 accccccacc tggcgacagg tgcctctgcg gccaaaagcc acgtgtataa gatacacctg      4980
caaaggcggc acaaccccag tgccacgttg tgagttggat agttgtggaa agagtcaaat      5040
ggctctcctc aagcgtattc aacaaggggc tgaaggatgc ccagaaggta ccccattgta      5100
tgggatctga tctggggcct cggtgcacat gctttacatg tgtttagtcg aggttaaaaa      5160
aacgtctagg cccccgaac cacggggacg tggttttcct ttgaaaaca cgatgataat        5220 atggccacaa ccatggtgag caagggcgag gagctgttca ccggggtggt gcccatcctg      5280
gtcgagctgg acggcgacgt aaacggccac aagttcagcg tgtccggcga gggcgagggc      5340
gatgccacct acggcaagct gaccctgaag ttcatctgca ccaccggcaa gctgcccgtg      5400
ccctggccca ccctcgtgac cacccctgacc tacggcgtgc agtgcttcag ccgctacccc      5460
gaccacatga gcagcacga cttcttcaag tccgccatgc ccgaaggcta cgtccaggag      5520
cgcaccatct tcttcaagga cgacggcaac tacaagaccc gcgccgaggt gaagttcgag      5580
ggcgacaccc tggtgaaccg catcgagctg aagggcatcg acttcaagga ggacggcaac      5640
atcctggggc acaagctgga gtacaactac aacagccaca acgtctatat catggccgac      5700
aagcagaaga acggcatcaa ggtgaacttc aagatccgcc acaacatcga ggacggcagc      5760
gtgcagctcg ccgaccacta ccagcagaac acccccatcg gcgacggccc cgtgctgctg      5820
cccgacaacc actacctgag cacccagtcc gccctgagca agaccccaa cgagaagcgc      5880 gatcacatgg tcctgctgga gttcgtgacc gccgccggga tcactctcgg catggacgag      5940
ctgtacaagt aagtcgacaa tcaacctctg gattacaaaa tttgtgaaag attgactggt      6000
attcttaact atgttgctcc ttttacgcta tgtggatacg ctgctttaat gcctttgtat      6060
catgctattg cttcccgtat ggctttcatt ttctcctcct tgtataaatc ctggttgctg      6120
tctctttatg aggagttgtg gcccgttgtc aggcaacgtg gcgtggtgtg cactgtgttt      6180
gctgacgcaa cccccactgg ttggggcatt gccaccacct gtcagctcct ttccgggact      6240
ttcgctttcc ccctccctat tgccacggcg gaactcatcg ccgcctgcct tgcccgctgc      6300
tggacagggg ctcggctgtt gggcactgac aattccgtgg tgttgtcggg aagctgacg      6360 tccttttccat ggctgctcgc ctgtgttgcc acctggattc tgcgcgggac gtccttctgc     6420
tacgtccctt cggccctcaa tccagcggac cttccttccc gcggcctgct gccggctctg      6480
cggcctcttc cgcgtcttcg ccttcgccct cagacgagtc ggatctccct ttgggccgcc      6540
tccccgcctg gaattcgagc tcgagcttgt taacatcgat aaaataaaag attttattta      6600
gtctccagaa aaaggggga atgaaagacc ccacctgtag gtttggcaag ctagcttaag      6660
taacgccatt ttgcaaggca tggaaaaata cataactgag aatagagaag ttcagatcaa      6720
ggtcaggaac agatggaaca gctgaatatg ggccaaacag gatatctgtg gtaagcagtt      6780
cctgccccgg ctcagggcca agaacagatg gaacagctga atatgggcca acaggatat       6840 ctgtggtaag cagttcctgc cccggctcag ggccaagaac agatggtccc cagatgcggt      6900
ccagccctca gcagtttcta gagaaccatc agatgtttcc agggtgcccc aaggacctga     6960
aatgaccctg tgccttattt gaactaacca atcagttcgc ttctcgcttc tgttcgcgcg      7020
cttctgctcc ccgagctcaa taaaagagcc cacaacccct cactcggggc gccagtcctc      7080
```

```
cgattgactg agtcgcccgg gtacccgtgt atccaataaa ccctcttgca gttgcatccg    7140
acttgtggtc tcgctgttcc ttgggagggt ctcctctgag tgattgacta cccgtcagcg    7200
ggggtctttc atttccgact tgtggtctcg ctgccttggg agggtctcct ctgagtgatt    7260 gactaccccgt cagcggggt cttcacatgc agcatgtatc aaaattaatt tggttttttt    7320
tcttaagtat ttacattaaa tggccatagt tgcattaatg aatcggccaa cgcgcgggga    7380
gaggcggttt gcgtattggc gctcttccgc ttcctcgctc actgactcgc tgcgctcggt    7440
cgttcggctg cggcgagcgg tatcagctca ctcaaaggcg gtaatacggt tatccacaga    7500
atcaggggat aacgcaggaa agaacatgtg agcaaaaggc cagcaaaagg ccaggaaccg    7560
taaaaaggcc gcgttgctgg cgttttttcca taggctccgc cccctgacg agcatcacaa    7620 aaatcgacgc tcaagtcaga ggtggcgaaa cccgacagga ctataaagat accaggcgtt    7680
tccccctgga agctccctcg tgcgctctcc tgttccgacc ctgccgctta ccggatacct    7740
gtccgccttt ctcccttcgg gaagcgtggc gctttctcat agctcacgct gtaggtatct    7800
cagttcggtg taggtcgttc gctccaagct gggctgtgtg cacgaaccccc ccgttcagcc    7860 cgaccgctgc gccttatccg gtaactatcg tcttgagtcc aacccggtaa gacacgactt    7920
atcgccactg gcagcagcca ctggtaacag gattagcaga gcgaggtatg taggcggtgc    7980
tacagagttc ttgaagtggt ggcctaacta cggctacact agaaggacag tatttggtat    8040
ctgcgctctg ctgaagccag ttaccttcgg aaaaagagtt ggtagctctt gatccggcaa    8100
acaaaccacc gctggtagcg gtggtttttt tgtttgcaag cagcagatta cgcgcagaaa    8160
aaaaggatct caagaagatc ctttgatctt ttctacgggg tctgacgctc agtggaacga    8220
aaactcacgt taagggattt tggtcatgag attatcaaaa aggatcttca cctagatcct    8280
tttaaattaa aaatgaagtt tgcggccggc cgcaaatcaa tctaaagtat atatgagtaa    8340
acttggtctg acagttacca atgcttaatc agtgaggcac ctatctcagc gatctgtcta    8400
tttcgttcat ccatagttgc ctgactcccc gtcgtgtaga taactacgat acgggagggc    8460
ttaccatctg gccccagtgc tgcaatgata ccgcgagacc cacgctcacc ggctccagat    8520
ttatcagcaa taaaccagcc agccggaagg gccgagcgca gaagtggtcc tgcaacttta    8580
tccgcctcca tccagtctat taattgttgc cgggaagcta gagtaagtag ttcgccagtt    8640
aatagtttgc gcaacgttgt tgccattgct acaggcatcg tggtgtcacg ctcgtcgttt    8700
ggtatggctt cattcagctc cggttcccaa cgatcaaggc gagttacatg atcccccatg    8760
ttgtgcaaaa aagcggttag ctccttcggt cctccgatcg ttgtcagaag taagttggcc    8820
gcagtgttat cactcatggt tatggcagca ctgcataatt ctcttactgt catgccatcc    8880
gtaagatgct tttctgtgac tggtgagtac tcaaccaagt cattctgaga atagtgtatg    8940
cggcgaccga gttgctcttg cccggcgtca cacgggata ataccgcgcc acatagcaga    9000
actttaaaag tgctcatcat tggaaaacgt tcttcggggc gaaaactctc aaggatctta    9060
ccgctgttga tccagttc gatgtaaccc actcgtgcac ccaactgatc ttcagcatct    9120
tttactttca ccagcgtttc tgggtgagca aaaacaggaa ggcaaaatgc cgcaaaaaag    9180
ggaataaggg cgacacggaa atgttgaata ctcatactct tcctttttca at           9232
```

REGENERATING FUNCTIONAL NEURONS FOR TREATMENT OF DISEASE AND INJURY IN THE NERVOUS SYSTEM

REFERENCE TO RELATED APPLICATIONS

This application is a continuation of U.S. patent application Ser. No. 14/438,765, filed Apr. 27, 2015, which is a U.S. national stage of PCT/US2013/051277, filed Jul. 19, 2013, which claims priority from U.S. Provisional Patent Application Ser. Nos. 61/673,471, filed Jul. 19, 2012 and 61/762,506, filed Feb. 8, 2013, the entire content of each application is incorporated herein by reference.

GOVERNMENT SUPPORT

This invention was made with government support under Grant No. MH083911, awarded by the National Institutes of Health. The Government has certain rights in the invention.

FIELD OF THE INVENTION

General aspects of the invention relate to the in situ conversion of glial cells to functional neuronal cells in the central nervous system (CNS), and the methods to transforming glial cells to neuronal cells both in vitro and in vivo.

BACKGROUND OF THE INVENTION

The central nervous system in mammals is largely unable to regenerate itself following injury. Neurons are often killed or injured as a result of an injury or neurological condition, such as a disease or other pathology. It is well known that glial cells become reactive following brain or spinal cord injury, after a stroke or neurodegenerative diseases such as Alzheimer's disease. These reactive glial cells can proliferate and maintain a high number in the injury site, and eventually form a dense scar tissue called glial scar to prevent the growth of neurons.

Currently there is no method available to reverse glial scar for brain repair. There is an urgent need for methods of treatment of neurological conditions, particularly for generation of neurons in a subject having a neurological condition.

SUMMARY OF THE INVENTION

Methods of producing a neuronal phenotype in a glial cell are provided according to aspects of the present invention including expressing exogenous NeuroD1 in the glial cell, wherein the glial cell is selected from the group consisting of: an astrocyte, a reactive astrocyte, an NG2 cell and a reactive NG2 cell. The glial cell may be human or non-human mammalian, in vitro or in vivo.

Methods of producing a neuronal phenotype in a glial cell are provided according to aspects of the present invention including expressing exogenous NeuroD1 in the glial cell, wherein the glial cell is selected from the group consisting of: an astrocyte, a reactive astrocyte, an NG2 cell and a reactive NG2 cell and wherein expressing exogenous NeuroD1 comprises delivering an expression vector comprising a nucleic acid encoding NeuroD1 to the glial cell.

Methods of producing a neuronal phenotype in a glial cell are provided according to aspects of the present invention including expressing exogenous NeuroD1 in the glial cell, wherein the glial cell is selected from the group consisting of: an astrocyte, a reactive astrocyte, an NG2 cell and a reactive NG2 cell and wherein expressing exogenous NeuroD1 comprises delivering a viral expression vector comprising a nucleic acid encoding NeuroD1 to the glial cell.

Methods of producing a neuronal phenotype in a glial cell are provided according to aspects of the present invention including expressing exogenous NeuroD1 in the glial cell, wherein the glial cell is selected from the group consisting of: an astrocyte, a reactive astrocyte, an NG2 cell and a reactive NG2 cell and wherein expressing exogenous NeuroD1 comprises delivering a retrovirus expression vector comprising a nucleic acid encoding NeuroD1 to the glial cell.

The neuronal phenotype produced in a glial cell in which NeuroD1 is exogenously expression include one or more, or all, of: neuronal morphology, expression of one or more neuronal markers, electrophysiologic characteristics of neurons, synapse formation and release of neurotransmitter.

Methods of producing a neuronal phenotype in a glial cell are provided according to aspects of the present invention including expressing exogenous NeuroD1 in the glial cell, wherein NeuroD1 is the only exogenously expressed transcription factor in the glial cell and wherein the glial cell is selected from the group consisting of: an astrocyte, a reactive astrocyte, an NG2 cell and a reactive NG2 cell. The glial cell may be human or non-human mammalian, in vitro or in vivo.

The neuronal phenotype produced in a glial cell in which NeuroD1 is the only exogenously expressed transcription factor include one or more, or all, of: neuronal morphology, expression of one or more neuronal markers, electrophysiologic characteristics of neurons, synapse formation and release of neurotransmitter.

Methods of producing a neuronal phenotype in a glial cell are provided according to aspects of the present invention including expressing exogenous NeuroD1 in the glial cell, wherein NeuroD1 is the only exogenously expressed transcription factor in the glial cell, wherein the glial cell is selected from the group consisting of an astrocyte, a reactive astrocyte, an NG2 cell and a reactive NG2 cell and wherein expressing exogenous NeuroD1 comprises delivering an expression vector comprising a nucleic acid encoding NeuroD1 to the glial cell.

Methods of producing a neuronal phenotype in a glial cell are provided according to aspects of the present invention including expressing exogenous NeuroD1 in the glial cell, wherein NeuroD1 is the only exogenously expressed transcription factor in the glial cell, wherein the glial cell is selected from the group consisting of: an astrocyte, a reactive astrocyte, an NG2 cell and a reactive NG2 cell and wherein expressing exogenous NeuroD1 comprises delivering a viral expression vector comprising a nucleic acid encoding NeuroD1 to the glial cell.

Methods of producing a neuronal phenotype in a glial cell are provided according to aspects of the present invention including expressing exogenous NeuroD1 in the glial cell, wherein NeuroD1 is the only exogenously expressed transcription factor in the glial cell, wherein the glial cell is selected from the group consisting of an astrocyte, a reactive astrocyte, an NG2 cell and a reactive NG2 cell and wherein expressing exogenous NeuroD1 comprises delivering a retrovirus expression vector comprising a nucleic acid encoding NeuroD1 to the glial cell.

Methods of producing a neuronal phenotype in a glial cell are provided according to aspects of the present invention including expressing exogenous NeuroD1 in the glial cell, wherein NeuroD1 is the only exogenously expressed transcription factor in the glial cell, wherein the glial cell is selected from the group consisting of: an astrocyte, a reactive astrocyte, an NG2 cell and a reactive NG2 cell and wherein expressing exogenous NeuroD1 comprises delivering a retrovirus expression vector comprising a nucleic acid encoding NeuroD1 to the glial cell.

Compositions including an in vitro glial cell including exogenous NeuroD1 are provided according to aspects of the present invention.

Compositions including an in vitro glial cell comprising an expression vector encoding NeuroD1 are provided according to aspects of the present invention.

Compositions including an in vitro glial cell including exogenous NeuroD1 are provided according to aspects of the present invention which have a neuronal phenotype, wherein the neuronal phenotype comprises one or more of: neuronal morphology, expression of one or more neuronal markers, electrophysiologic characteristics of neurons, synapse formation and release of neurotransmitter.

Compositions including an in vitro glial cell comprising an expression vector encoding NeuroD1 are provided according to aspects of the present invention which have a neuronal phenotype, wherein the neuronal phenotype comprises one or more of: neuronal morphology, expression of one or more neuronal markers, electrophysiologic characteristics of neurons, synapse formation and release of neurotransmitter.

Compositions including an in vitro glial cell including exogenous NeuroD1 are provided according to aspects of the present invention, wherein NeuroD1 is the only exogenously expressed transcription factor in the glial cell and which have a neuronal phenotype, wherein the neuronal phenotype comprises one or more of: neuronal morphology, expression of one or more neuronal markers, electrophysiologic characteristics of neurons, synapse formation and release of neurotransmitter.

Compositions including an in vitro glial cell comprising an expression vector encoding NeuroD1 are provided according to aspects of the present invention, wherein NeuroD1 is the only exogenously expressed transcription factor in the glial cell and which have a neuronal phenotype, wherein the neuronal phenotype comprises one or more of: neuronal morphology, expression of one or more neuronal markers, electrophysiologic characteristics of neurons, synapse formation and release of neurotransmitter.

Methods of treating a neurological condition in a subject in need thereof are provided according to aspects of the present invention which include administering a therapeutically effective dose of NeuroD1 to a glial cell of the subject; whereby exogenous NeuroD1 is expressed in the glial cell, producing a neuronal phenotype in the glial cell to ameliorate the neurological condition of the subject.

Methods of treating a neurological condition in a subject in need thereof are provided according to aspects of the present invention which include administering a therapeutically effective dose of NeuroD1 to a glial cell of the subject, wherein administering the therapeutically effective dose of NeuroD1 comprises administering an expression vector comprising a nucleic acid sequence encoding NeuroD1 protein; whereby exogenous NeuroD1 is expressed in the glial cell, producing a neuronal phenotype in the glial cell to ameliorate the neurological condition of the subject.

Methods of treating a neurological condition in a subject in need thereof are provided according to aspects of the present invention which include administering a therapeutically effective dose of NeuroD1 to a glial cell of the subject, wherein administering the therapeutically effective dose of NeuroD1 comprises administering an expression vector comprising a nucleic acid sequence encoding NeuroD1 protein, wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof; whereby exogenous NeuroD1 is expressed in the glial cell, producing a neuronal phenotype in the glial cell to ameliorate the neurological condition of the subject.

Method of treating a neurological condition in a subject in need thereof according to aspects of the present invention are methods of treating a neurological condition characterized by presence of reactive astrocytes.

Method of treating a neurological condition in a subject in need thereof according to aspects of the present invention are methods of treating an injury to the central or peripheral nervous system.

Method of treating a neurological condition in a subject in need thereof according to aspects of the present invention are methods of treating Alzheimer disease, Parkinson disease, amyotrophic lateral sclerosis (ALS), epilepsy and stroke.

Method of treating a neurological condition in a subject in need thereof according to aspects of the present invention include administering a therapeutically effective dose of NeuroD1 by local administration, systemic administration or a combination thereof.

Method of treating a neurological condition in a subject in need thereof according to aspects of the present invention include administering an expression vector comprising a nucleic acid sequence encoding NeuroD1 protein, the nucleic acid sequence operably linked to a ubiquitous promoter by local administration.

Method of treating a neurological condition in a subject in need thereof according to aspects of the present invention include administering an expression vector comprising a nucleic acid sequence encoding NeuroD1 protein, the nucleic acid sequence operably linked to a ubiquitous promoter by local administration to a site of injury or disease in the nervous system of the subject where additional neurons and/or fewer glial cells or reactive glial cells are desirable.

Method of treating a neurological condition in a subject in need thereof according to aspects of the present invention include administering an expression vector comprising a nucleic acid sequence encoding NeuroD1 protein, the nucleic acid sequence operably linked to a cell type-specific promoter selected from the group consisting of: an astrocyte-specific promoter and an NG2 cell-specific promoter, by local administration to a site of injury or disease in the nervous system of the subject where additional neurons and/or fewer glial cells or reactive glial cells are desirable or by systemic administration to the subject.

Method of treating a neurological condition in a subject in need thereof according to aspects of the present invention include administering an expression vector comprising a nucleic acid sequence encoding NeuroD1 protein, wherein the expression vector is a viral expression vector.

Method of treating a neurological condition in a subject in need thereof according to aspects of the present invention include administering an expression vector comprising a nucleic acid sequence encoding NeuroD1 protein, wherein the expression vector is a retrovirus.

Method of treating a neurological condition in a subject in need thereof according to aspects of the present invention include administering an expression vector comprising a nucleic acid sequence encoding NeuroD1 protein, wherein the expression vector is an adenovirus.

Method of treating a neurological condition in a subject in need thereof according to aspects of the present invention include administering an expression vector comprising a nucleic acid sequence encoding NeuroD1 protein, wherein the expression vector is an adeno-associated virus.

Method of treating a neurological condition in a subject in need thereof according to aspects of the present invention include administering an expression vector comprising a nucleic acid sequence encoding NeuroD1 protein, wherein the expression vector is a lentivirus.

Method of treating a neurological condition in a subject in need thereof according to aspects of the present invention include administering an expression vector comprising a nucleic acid sequence encoding NeuroD1 protein, wherein administering the therapeutically effective dose of NeuroD1 comprises administering NeuroD1 protein.

Method of treating a neurological condition in a subject in need thereof according to aspects of the present invention include administering an expression vector comprising a nucleic acid sequence encoding NeuroD1 protein, wherein administering the therapeutically effective dose of NeuroD1 comprises administering mRNA encoding NeuroD1 protein.

Method of treating a neurological condition in a subject in need thereof according to aspects of the present invention include providing a viral expression vector comprising a nucleic acid encoding NeuroD1; and delivering the viral expression vector to the central nervous system or peripheral nervous system of the subject, whereby the viral vector infects dividing cells of the central nervous system or peripheral nervous system, respectively, producing infected cells and whereby exogenous NeuroD1 is expressed in the infected cells at a therapeutically effective level, wherein the expression of NeuroD1 in the infected cells results in a greater number of neurons in the subject compared to an untreated subject having the same neurological condition, whereby the neurological condition is treated.

Methods of treating a neurological condition in a subject in need thereof are provided according to aspects of the present invention which include administering a therapeutically effective dose of NeuroD1 to a glial cell of the subject, wherein NeuroD1 is the only exogenously expressed transcription factor in the glial cell; whereby exogenous NeuroD1 is expressed in the glial cell, producing a neuronal phenotype in the glial cell to ameliorate the neurological condition of the subject.

Expression vectors are provided according to aspects of the present invention which include a glial cell specific promoter operably linked to a nucleic acid encoding NeuroD1.

Expression vectors are provided according to aspects of the present invention which include a glial cell specific promoter operably linked to a nucleic acid encoding NeuroD1, wherein NeuroD1 is the only transcription factor encoded by the nucleic acid.

Expression vectors are provided according to aspects of the present invention which include a glial cell specific promoter operably linked to a nucleic acid encoding NeuroD1, wherein the glial cell specific promoter is an astrocyte specific promoter or an NG2 cell specific promoter.

Expression vectors are provided according to aspects of the present invention which include a glial cell specific promoter operably linked to a nucleic acid encoding NeuroD1, wherein the glial cell specific promoter is an astrocyte specific promoter or an NG2 cell specific promoter and wherein the expression vector is a viral vector.

Expression vectors are provided according to aspects of the present invention which include a glial cell specific promoter operably linked to a nucleic acid encoding NeuroD1, wherein the glial cell specific promoter is an astrocyte specific promoter or an NG2 cell specific promoter and wherein the expression vector is a retroviral expression vector.

Expression vectors are provided according to aspects of the present invention which include a glial cell specific promoter operably linked to a nucleic acid encoding NeuroD1, wherein the glial cell specific promoter is an astrocyte specific promoter or an NG2 cell specific promoter and wherein the expression vector is an adenovirus, adeno-associated virus or lentivirus.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter and wherein the expression vector is a viral vector.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter and wherein the expression vector is a retroviral expression vector.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter and wherein the expression vector is an adenovirus, adeno-associated virus or lentivirus.

Expression vectors are provided according to aspects of the present invention which include a glial cell specific promoter operably linked to a nucleic acid encoding NeuroD1, wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter and wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter, wherein the expression vector is a viral vector and wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter, wherein the expression vector is a retroviral vector and wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof.

Expression vectors are provided according to aspects of the present invention which include a glial cell specific promoter operably linked to a nucleic acid encoding NeuroD1, wherein the promoter is a GFAP promoter, NG2 promoter, Aldh1L1 promoter or LCN2 promoter, wherein the expression vector is an adenovirus, adeno-associated virus or lentivirus vector and wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof.

BRIEF DESCRIPTION OF THE DRAWINGS

FIG. 3D shows representative images illustrating NeuroD1-GFP fluorescence in 5xFAD mouse cortex in the top panel and VGlut1 immunofluorescence, arrowhead, in the same field shown in the bottom panel;

FIG. 3E shows representative images illustrating GAD65 immunofluorescence, arrow, in 5xFAD mouse cortex in the same field as in FIG. 3D in the top panel and the overlap of NeuroD1-GFP fluorescence, VGlut1 immunofluorescence and GAD65 immunofluorescence in the same field, shown in the bottom panel;

FIG. 3F shows representative traces of sodium and potassium currents of NeuroD1-converted neurons at 28 DPI with retrovirus construct encoding NeuroD1-GFP in AD cortical slices (5xFAD mouse cortex);

FIG. 3G shows representative traces of spontaneous synaptic events recorded from NeuroD1-converted neurons at 28 DPI with retrovirus construct encoding NeuroD1-GFP in the AD cortical slices;

FIG. 3H shows an enlarged view of two synaptic events shown in FIG. 3G;

FIG. 7A shows large receptor currents induced by bath application of GABA (100 µM) in mouse astrocyte-converted neurons;

FIG. 7B shows glutamate (100 µM) evoked currents;

FIG. 7C shows NMDA (100 µM) evoked currents;

FIG. 7D shows spontaneous synaptic currents recorded from NeuroD1-converted neurons;

FIGS. 17C and 17D are representative images showing GABA immunostaining in mouse cultured neurons;

DETAILED DESCRIPTION OF THE INVENTION

Figure 1A:
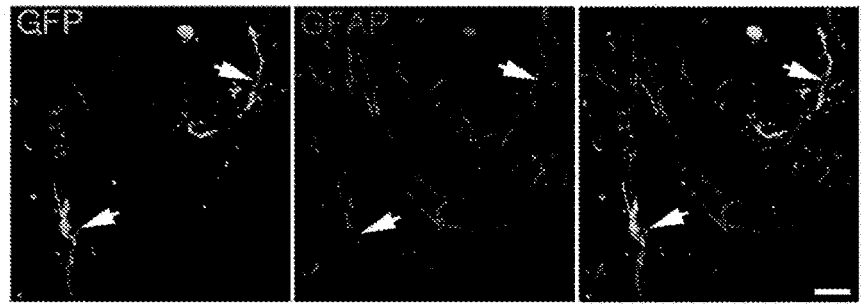
FIG. 1A shows representative images illustrating GFP fluorescence in the left panel, GFAP immunofluorescence in the same field, shown in the middle panel, and the overlap of GFP fluorescence and GFAP immunofluorescence in the same field, shown in the right panel.

Unexpectedly, a single transcription factor, NeuroD1, converts astrocytes, reactive astrocytes, NG2 cells and reactive NG2 cells into functional neurons, as disclosed herein. NeuroD1 converts astrocytes and reactive astrocytes into functional glutamatergic neurons and converts NG2 cells and reactive NG2 cells predominantly into functional GABAergic neurons, along with a few functional glutamatergic neurons.

Conversion of astrocytes, reactive astrocytes, NG2 cells and/or reactive NG2 cells to neurons in vitro, ex vivo and/or in vivo may be used to treat neurodegenerative disease and injury, replacing degenerated neurons and restoring neural function.

Provided by the present invention are methods for direct conversion of reactive glial cells into functional neurons by a single transcription factor, NeuroD1, to treat injury and/or disease of the nervous system.

Expression of NeuroD1 in astrocytes and/or NG2 cells converts the astrocytes and NG2 cells into functional neurons and has several significant consequences on brain injury: 1) reduces the number of reactive glial cells in the injury site; 2) generates new functional neurons to connect with existing neurons; 3) axon fibers increase in the injury site; 4) blood vessels increase after conversion of astrocytes and NG2 cells into functional neurons; 5) cell death decreases after conversion of astrocytes and NG2 cells into functional neurons. Therefore, the entire landscape of the injury site is changed into a more neuro-permissive environment, which will be a critical step toward functional recovery.

NeuroD1-mediated direct conversion of glial cells into functional neurons not only occurs in young adult animals, but also in very old animals and even old animals with Alzheimer's disease, making it possible for brain repair in the adult brain. Moreover, reactive glial cells in an accepted model of Alzheimer's disease are converted into functional neurons by the exogenous expression of a single transcription factor, NeuroD1, and such conversion was accompanied with reduced amyloid β peptide deposits.

Conversion of astrocytes, reactive astrocytes, NG2 cells and reactive NG2 cells into functional neurons by expression of exogenous NeuroD1 alone, called NeuroD1 converted neurons herein, represent the first in vitro and in vivo direct conversion of these cells to functional neurons. The NeuroD1 converted neurons are characterized by long-term stability of the neuronal phenotype.

Methods for producing new neurons in the brain in vivo are provided according to aspects of the present invention which include introducing NeuroD1 into a glial cell, particularly into an astrocyte, reactive astrocyte, NG2 cell or reactive NG2 cell, thereby "converting" the glial cell to a neuron, a "NeuroD1 converted neuron."

Methods and compositions of the present invention have various uses, including for example, production of neurons in situ to treat a neurological condition of a subject.

Advantageously, in situ replacement of injured neuronal cells by conversion of endogenous reactive astrocytes into neurons eliminates the possibility of immunorejection such as can occur when a tissue/cell transplant is performed to replace damaged neuronal cells.

After brain/spinal cord injury or neurological disorders, glial cells such as astrocytes often over proliferate. Changing surplus glial cells into neurons will reduce the number of reactive glial cells, and in the mean while replenish lost neurons for internal brain repair.

Methods of producing a neuronal phenotype from a glial cell, such as an NG2 cell, reactive NG2 cell, astrocyte and/or reactive astrocyte, are provided according to aspects of the present invention which include expressing exogenous NeuroD1 in the glial cell.

The glial cell, such as an NG2 cell, reactive NG2 cell, astrocyte and/or reactive astrocyte, is in vitro, ex vivo or in vivo. Glial cells expressing exogenous NeuroD1 may be transferred to a site of nervous system injury or disease to treat a subject in need thereof.

The glial cell, such as an NG2 cell, reactive NG2 cell, astrocyte and/or reactive astrocyte, may be human or non-human mammalian, but can be non-mammalian as well.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3$^{rd}$ Ed., 2001; F. M. Asubel, Ed., Short Protocols in Molecular Biology, Current Protocols; 5$^{th}$ Ed., 2002; B. Alberts et al., Molecular Biology of the Cell, 4$^{th}$ Ed., Garland, 2002; D. L. Nelson and M. M. Cox, Lehninger Principles of Biochemistry, 4$^{th}$ Ed., W.H. Freeman & Company, 2004; Engelke, D. R., RNA Interference (RNAi): Nuts and Bolts of RNAi Technology, DNA Press LLC, Eagleville, Pa., 2003; Herdewijn, p. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, Cold Spring Harbor Laboratory Press, 3$^{rd}$ Ed.; Dec. 15, 2002, ISBN-10:0879695919; Kursad Turksen (Ed.), Embryonic Stem Cells: Methods and Protocols in Methods in Molecular Biology, 2002; 185, Human Press: Current Protocols in Stem Cell Biology, ISBN: 9780470151808.

The singular terms "a," "an," and "the" are not intended to be limiting and include plural referents unless explicitly stated otherwise or the context clearly indicates otherwise.

The term "NeuroD1 protein" refers to a bHLH proneural transcription factor involved in embryonic brain development and in adult neurogenesis, see Cho, J. H. et al., Mol, Neurobiol., 30:35-47, 2004; Kuwabara, T. et al., Nature Neurosci., 12:1097-1105, 2009; and Gao, Z. et al., Nature Neurosci., 12:1090-1092, 2009. NeuroD1 is expressed late in development, mainly in the nervous system and is involved in neuronal differentiation, maturation and survival.

The with "NeuroD1 protein" encompasses human NeuroD1 protein, identified here as SEQ ID NO: 2 and mouse NeuroD1 protein, identified here as SEQ ID NO: 4. In addition to the NeuroD1 protein of SEQ ID NO: 2 and SEQ ID NO: 4, the term "NeuroD1 protein" encompasses variants of NeuroD1 protein, such as variants of SEQ ID NO: 2 and SEQ ID NO: 4, which may be included in methods of the present invention. As used herein, the term "variant" refers to naturally occurring genetic variations and recombinantly prepared variations, each of which contain one or more changes in its amino acid sequence compared to a reference NeuroD1 protein, such as SEQ ID NO: 2 or SEQ ID NO: 4. Such changes include those in which one or more amino acid residues have been modified by amino acid substitution, addition or deletion. The term "variant" encompasses orthologs of human NeuroD1, including for example mammalian and bird NeuroD1, such as, but not limited to NeuroD1 orthologs from a non-human primate, cat, dog, sheep, goat, horse, cow, pig, bird, poultry animal and rodent such as but not limited to mouse and rat. In a non-limiting example, mouse NeuroD1, exemplified herein as amino acid sequence SEQ ID NO: 4 is an ortholog of human NeuroD1.

Preferred variants have at least 75%, 80%, 85%, 90%, 91%, 92%, 93%, 94%, 95%, 96%, 97%, 98%, or 99% identity to SEQ ID NO: 2 or SEQ ID NO: 4.

Mutations can be introduced using standard molecular biology techniques, such as site-directed mutagenesis and PCR-mediated mutagenesis. One of skill in the art will recognize that one or more amino acid mutations can be introduced without altering the functional properties of the NeuroD1 protein. For example, one or more amino acid substitutions, additions, or deletions can be made without altering the functional properties of the NeuroD1 protein of SEQ ID NO: 2 or 4.

Conservative amino acid substitutions can be made in a NeuroD1 protein to produce a NeuroD1 protein variant. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

NeuroD1 variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped. BLAST, and PSI Blast programs, the default parameters of the respective programs (e.g., of XBLAST and NBLAST) are used (see, e.g., the NCBI website). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

The term "NeuroD1 protein" encompasses fragments of the NeuroD1 protein, such as fragments of SEQ ID NOs. 2 and 4 and variants thereof, operable in methods and compositions of the present invention.

NeuroD1 proteins and nucleic acids may be isolated from natural sources, such as the brain of an organism or cells of a cell line which expresses NeuroD1. Alternatively, NeuroD1 protein or nucleic acid may be generated recombinantly, such as by expression using an expression construct, in vitro or in vivo. NeuroD1 proteins and nucleic acids may also be synthesized by well-known methods.

NeuroD1 included in methods and compositions of the present invention is preferably produced using recombinant nucleic acid technology. Recombinant NeuroD1 production includes introducing a recombinant expression vector encompassing a DNA sequence encoding NeuroD1 into a host cell.

A nucleic acid sequence encoding NeuroD1 introduced into a host cell to produce NeuroD1 according to embodiments of the invention encodes SEQ ID NO: 2, SEQ ID NO: 4, or a variant thereof.

According to aspects of the present invention, the nucleic acid sequence identified herein as SEQ ID NO: 1 encodes SEQ ID NO: 2 and is included in an expression vector and expressed to produce NeuroD1. According to aspects of the present invention, the nucleic acid sequence identified herein as SEQ ID NO: 3 encodes SEQ ID NO: 4 and is included in an expression vector and expressed to produce NeuroD1.

It is appreciated that due to the degenerate nature of the genetic code, nucleic acid sequences substantially identical to SEQ ID NOs. 1 and 3 encode NeuroD1 and variants of NeuroD1, and that such alternate nucleic acids may be included in an expression vector and expressed to produce NeuroD1 and variants of NeuroD1. One of skill in the art will appreciate that a fragment of a nucleic acid encoding NeuroD1 protein can be used to produce a fragment of a NeuroD1 protein.

The term "expression vector" refers to a recombinant vehicle for introducing a nucleic acid encoding NeuroD1 into a host cell in vitro or in vivo where the nucleic acid is expressed to produce NeuroD1. In particular embodiments, an expression vector including SEQ ID NO: 1 or 3 or a substantially identical nucleic acid sequence is expressed to produce NeuroD1 in cells containing the expression vector. The term "recombinant" is used to indicate a nucleic acid construct in which two or more nucleic acids are linked and which are not found linked in nature. Expression vectors include, but are not limited to plasmids, viruses, BACs and YACs. Particular viral expression vectors illustratively include those derived from adenovirus, adeno-associated virus, retrovirus, and lentivirus.

An expression vector contains a nucleic acid that includes segment encoding a polypeptide of interest operably linked to one or more regulatory elements that provide for transcription of the segment encoding the polypeptide of interest. The term "operably linked" as used herein refers to a nucleic acid in functional relationship with a second nucleic acid. The term "operably linked" encompasses functional connection of two or more nucleic acid molecules, such as a nucleic acid to be transcribed and a regulatory element. The term "regulatory element" as used herein refers to a nucleotide sequence which controls some aspect of the expression of an operably linked nucleic acid. Exemplary regulatory elements include an enhancer, such as, but not limited to: woodchuck hepatitis virus posttranscriptional regulatory element (WPRE); an internal ribosome entry site (IRES) or a 2A domain; an intron; an origin of replication; a polyadenylation signal (pA); a promoter; a transcription termination sequence; and an upstream regulatory domain, which contribute to the replication, transcription, posttranscriptional processing of an operably linked nucleic acid sequence. Those of ordinary skill in the art are capable of selecting and using these and other regulatory elements in an expression vector with no more than routine experimentation.

The term "promoter" as used herein refers to a DNA sequence operably linked to a nucleic acid sequence to be transcribed such as a nucleic acid sequence encoding NeuroD1. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors.

As will be recognized by the skilled artisan, the 5' non-coding region of a gene can be isolated and used in its entirety as a promoter to drive expression of an operably linked nucleic acid. Alternatively, a portion of the 5' non-coding region can be isolated and used to drive expression of an operably linked nucleic acid. In general, about 500-6000 bp of the 5' non-coding region of a gene is used to drive expression of the operably linked nucleic acid. Optionally, a portion of the 5' non-coding region of a gene containing a minimal amount of the 5' non-coding region needed to drive expression of the operably linked nucleic acid is used. Assays to determine the ability of a designated portion of the 5' non-coding region of a gene to drive expression of the operably linked nucleic acid are well-known in the art.

Particular promoters used to drive expression of NeuroD1 according to methods described herein are "ubiquitous" or "constitutive" promoters, that drive expression in many, most, or all cell types of an organism into which the expression vector is transferred. Non-limiting examples of ubiquitous promoters that can be used in expression of NeuroD1 are cytomegalovirus promoter, simian virus 40 (SV40) early promoter, rous sarcoma virus promoter, adenovirus major late promoter, beta actin promoter, glyceraldehyde 3-phosphate dehydrogenase, glucose-regulated protein 78 promoter, glucose-regulated protein 94 promoter, heat shock protein 70 promoter, beta-kinesin promoter, ROSA promoter, ubiquitin B promoter, eukaryotic initiation factor 4A1 promoter and elongation Factor I promoter, all of which are well-known in the art and which can be isolated from primary sources using routine methodology or obtained from commercial sources.

Promoters can be derived entirely from a single gene or can be chimeric, having portions derived from more than one gene.

Combinations of regulatory sequences may be included in an expression vector and used to drive expression of NeuroD1. A non-limiting example included in an expression vector to drive expression of NeuroD1 is the CAG promoter which combines the cytomegalovirus CMV early enhancer element and chicken beta-actin promoter.

Particular promoters used to drive expression of NeuroD1 according to methods described herein are those that drive expression preferentially in glial cells, particularly astrocytes and/or NG2 cells. Such promoters are termed "astrocyte-specific" and/or "NG2 cell-specific" promoters.

Non-limiting examples of astrocyte-specific promoters are glial fibrillary acidic protein (GFAP) promoter and aldehyde dehydrogenase 1 family, member L1 (Aldh1L1) promoter.

Human GFAP promoter is shown herein as SEQ ID NO:6. Mouse Aldh1L1 promoter is shown herein as SEQ ID NO:7.

A non-limiting example of an NG2 cell-specific promoter is the promoter of the chondroitin sulfate proteoglycan 4 gene, also known as neuron-glial antigen 2 (NG2). Human NG2 promoter is shown herein as SEQ ID NO:8.

Particular promoters used to drive expression of NeuroD1 according to methods described herein are those that drive expression preferentially in reactive glial cells, particularly reactive astrocytes and/or reactive NG2 cells. Such promoters are termed "reactive astrocyte-specific" and/or "reactive NG2 cell-specific" promoters.

A non-limiting example of a "reactive astrocyte-specific" promoter is the promoter of the lipocalin 2 (lcn2) gene. Mouse lcn2 promoter is shown herein as SEQ ID NO:5.

Homologues and variants of ubiquitous and cell type-specific promoters may be used in expressing NeuroD1.

Promoter homologues and promoter variants can be included in an expression vector for expressing NeuroD1 according to the present invention. The terms "promoter homologue" and "promoter variant" refer to a promoter which has substantially similar functional properties to confer the desired type of expression, such as cell type-specific expression of NeuroD1 or ubiquitous expression of NeuroD1, on an operably linked nucleic acid encoding NeuroD1 compared to those disclosed herein. For example, a promoter homologue or variant has substantially similar functional properties to confer cell type-specific expression on an operably linked nucleic acid encoding NeuroD1 compared to GFAP, Aldh1L1, NG2, lcn2 and CAG promoters.

One of skill in the art will recognize that one or more nucleic acid mutations can be introduced without altering the functional properties of a given promoter. Mutations can be introduced using standard molecular biology techniques, such as site-directed mutagenesis and PCR-mediated mutagenesis, to produce promoter variants. As used herein, the term "promoter variant" refers to either an isolated naturally occurring or a recombinantly prepared variation of a reference promoter, such as, but not limited to, GFAP, Aldh1L1, NG2, lcn2 and pCAG promoters.

It is known in the art that promoters from other species are functional, e.g. the mouse Aldh1L1 promoter is functional in human cells. Homologues and homologous promoters from other species can be identified using bioinformatics tools known in the art, see for example. Xuan et al., 2005, Genome Biol 6:R72; Zhao et al., 2005. Nucl Acid. Res 33:D103-107; and Halees et al. 2003, Nucl. Acids. Res. 2003 31:3554-3559.

Structurally, homologues and variants of cell type-specific expression of NeuroD1 or and/or ubiquitous promoters have at least 80%, 81%, 82%, 83%, 84%, 85%, 86%, 87%, 88%, 89, 90%, 91%, 92%, 93%, 94%, 95%, 96%, 97%, 98%, 99%, or greater, nucleic acid sequence identity to the reference developmentally regulated and/or ubiquitous promoter and include a site for binding of RNA polymerase and, optionally, one or more binding sites for transcription factors.

A nucleic acid sequence which is substantially identical to SEQ ID NO: 1 or 3 is characterized as having a complementary nucleic acid sequence capable of hybridizing to SEQ ID NO: 1 or 3 under high stringency hybridization conditions.

In addition to one or more nucleic acids encoding NeuroD1, one or more nucleic acid sequences encoding additional proteins can be included in an expression vector. For example, such additional proteins include non-NeuroD1 proteins such as reporters, including, but not limited to, beta-galactosidase, green fluorescent protein and antibiotic resistance reporters.

In particular embodiments, the recombinant expression vector encodes at least NeuroD1 of SEQ ID NO: 2, a protein having at least 95% identity to SEQ ID NO: 2, or a protein encoded by a nucleic acid sequence substantially identical to SEQ ID NO: 1.

In particular embodiments, the recombinant expression vector encodes at least NeuroD1 of SEQ ID NO: 4, a protein having at least 95% identity to SEQ ID NO: 4, or a protein encoded by a nucleic acid sequence substantially identical to SEQ ID NO: 2.

SEQ ID NO:9 is an example of a nucleic acid including CAG promoter operably linked to a nucleic acid encoding NeuroD1, and further including a nucleic acid sequence encoding EGFP and an enhancer, WPRE. An IRES separates the nucleic acid encoding NeuroD1 and the nucleic acid encoding EGFP. SEQ ID NO:9 is inserted into an expression vector for expression of NeuroD1 and the reporter gene EGFP. Optionally, the IRES and nucleic acid encoding EGFP are removed and the remaining CAG promoter and operably linked nucleic acid encoding NeuroD1 is inserted into an expression vector for expression of NeuroD1. The WPRE or another enhancer is optionally included.

Optionally, a reporter gene is included in a recombinant expression vector encoding NeuroD1. A reporter gene may be included to produce a peptide or protein that serves as a surrogate marker for expression of NeuroD1 from the recombinant expression vector. The term "reporter gene" as used herein refers to gene that is easily detectable when expressed, for example by chemiluminescence, fluorescence, calorimetric reactions, antibody binding, inducible markers and/or ligand binding assays. Exemplary reporter genes include, but are not limited to, green fluorescent protein (GFP), enhanced green fluorescent protein (eGFP), yellow fluorescent protein (YFP), enhanced yellow fluorescent protein (eYFP), cyan fluorescent protein (CFP), enhanced cyan fluorescent protein (eCFP), blue fluorescent protein (BFP), enhanced blue fluorescent protein (eBFP), MmGFP (Zernicka-Goetz et al., Development, 124:1133-1137, 1997, dsRed, luciferase and beta-galactosidase (lacZ).

The process of introducing genetic material into a recipient host cell, such as for transient or stable expression of a desired protein encoded by the genetic material in the host cell is referred to as "transfection." Transfection techniques are well-known in the art and include, but are not limited to, electroporation, particle accelerated transformation also known as "gene gun" technology, liposome-mediated transfection, calcium phosphate or calcium chloride co-precipitation-mediated transfection, DEAE-dextran-mediated transfection, microinjection, polyethylene glycol mediated transfection, heat shock mediated transfection and virus-mediated transfection. As noted herein, virus-mediated transfection may be accomplished using a viral vector such as those derived from adenovirus, adeno-associated virus and lentivirus.

Optionally, a host cell is transfected ex-vivo and then re-introduced into a host organism. For example, cells or tissues may be removed from a subject, transfected with an expression vector encoding NeuroD1 and then returned to the subject.

Introduction of a recombinant expression vector including a nucleic acid encoding NeuroD1. or a functional fragment thereof into a host glial cell in vitro or in vivo for expression of exogenous NeuroD1 in the host glial cell to convert the glial cell to a neuron is accomplished by any of various transfection methodologies.

Expression of exogenous NeuroD1 in the host glial cell to convert the glial cell to a neuron is optionally achieved by introduction of mRNA encoding NeuroD1, or a functional fragment thereof, to the host glial cell in vitro or in vivo.

Expression of exogenous NeuroD1 in the host glial cell to convert the glial cell to a neuron is optionally achieved by introduction of NeuroD1 protein to the host glial cell in vitro or in vivo.

Details of these and other techniques are known in the art, for example, as described in J. Sambrook and D. W. Russell, Molecular Cloning: A Laboratory Manual, Cold. Spring Harbor Laboratory Press; 3rd Ed., 2001; F. M. Ausubel, Ed., Short Protocols in Molecular Biology, Current Protocols; 5th Ed., 2002; and Engelke, D. R., RNA Interference (RNAi): Nuts and Bolts of RNAi Technology, DNA Press LLC, Eagleville, Pa., 2003.

An expression vector including a nucleic acid encoding NeuroD1 or a functional fragment thereof, mRNA encoding NeuroD1 or a functional fragment thereof, and/or NeuroD1 protein, full-length or a functional fragment thereof, is optionally associated with a carrier for introduction into a host cell in-vitro or in-vivo.

In particular aspects, the carrier is a particulate carrier such as lipid particles including liposomes, micelles, unilamellar or multilamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further aspects of nanoparticles are described in S. M. Moghimi et al., FASEB J. 2005, 19, 311-30.

Expression of NeuroD1 using a recombinant expression vector is accomplished by introduction of the expression vector into a eukaryotic or prokaryotic host cell expression system such as an insect cell, mammalian cell, yeast cell, bacterial cell or any other single or multicellular organism recognized in the art. Host cells are optionally primary cells or immortalized derivative cells. Immortalized cells are those which can be maintained in-vitro for at least 5 replication passages.

Host cells containing the recombinant expression vector are maintained under conditions wherein NeuroD1 is produced. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

According to aspects of the present invention, a recombinant expression vector including a nucleic acid encoding NeuroD1 is introduced into glial cells of a subject. Expression of exogenous NeuroD1 in the glial cells "converts" the glial cells into neurons.

According to aspects of the present invention, a recombinant expression vector including a nucleic acid encoding NeuroD1 or a functional fragment thereof is introduced into astrocytes of a subject. Expression of exogenous NeuroD1 in the glial cells "converts" the astrocytes into neurons.

According to aspects of the present invention, a recombinant expression vector including a nucleic acid encoding NeuroD1 or a functional fragment thereof is introduced into reactive astrocytes of a subject. Expression of exogenous NeuroD1 or a functional fragment thereof in the reactive astrocytes "converts" the reactive astrocytes into neurons.

According to aspects of the present invention, a recombinant expression vector including a nucleic acid encoding NeuroD1 or a functional fragment thereof is introduced into NG2 cells of a subject. Expression of exogenous NeuroD1 or a functional fragment thereof in the NG2 cells "converts" the NG2 cells into neurons.

Detection of expression of exogenous NeuroD1 following introduction of a recombinant expression vector including a nucleic acid encoding the exogenous NeuroD1 or a functional fragment thereof is accomplished using any of various standard methodologies including, but not limited to, immunoassays to detect NeuroD1, nucleic acid assays to detect NeuroD1 nucleic acids and detection of a reporter gene co-expressed with the exogenous NeuroD1.

The terms "converts" and "converted" are used herein to describe the effect of expression of NeuroD1 or a functional fragment thereof resulting in a change of a glial cell, astrocyte or reactive astrocyte phenotype to a neuronal phenotype. Similarly, the phrases "NeuroD1 converted neurons" and "converted neurons" are used herein to designate a cell including exogenous NeuroD1 protein or a functional fragment thereof which has consequent neuronal phenotype.

The term "phenotype" refers to well-known detectable characteristics of the cells referred to herein. The neuronal phenotype can be, but is not limited to, one or more of: neuronal morphology, expression of one or more neuronal markers, electrophysiological characteristics of neurons, synapse formation and release of neurotransmitter. For example, neuronal phenotype encompasses but is not limited to: characteristic morphological aspects of a neuron such as presence of dendrites, an axon and dendritic spines; characteristic neuronal protein expression and distribution, such as presence of synaptic proteins in synaptic puncta, presence of MAP2 in dendrites; and characteristic electrophysiological signs such as spontaneous and evoked synaptic events.

In a further example, glial phenotype such as astrocyte phenotype and reactive astrocyte phenotypes encompasses but is not limited to: characteristic morphological aspects of astrocytes and reactive astrocytes such as a generally "star-shaped" morphology; and characteristic astrocyte and reactive astrocyte protein expression, such as presence of glial fibrillary acidic protein (GFAP).

The term "NeuroD1 nucleic acid" refers to an isolated NeuroD1 nucleic acid molecule.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "NeuroD1 nucleic acid" encompasses isolated NeuroD1 nucleic acids having a sequence that has at least 70%, 75%, 80%, 85%, 90%, 91%, 92%, 93%, 94%, 95%, 96%, 97%, 98%, or 99% identity to the DNA sequence set forth in SEQ ID NO: 1 or SEQ ID NO: 3, or the complement thereof, or a fragment thereof, or an isolated DNA molecule having a sequence that hybridizes under high stringency hybridization conditions to the nucleic acid set forth as SEQ ID NO: 1 or SEQ ID NO: 3, a complement thereof or a fragment thereof. The nucleic acid of SEQ ID NO: 3 is an example of an isolated DNA molecule having a sequence that hybridizes under high stringency hybridization conditions to the nucleic acid set forth in SEQ ID NO: 1. A fragment of a NeuroD1 nucleic acid is any fragment of a NeuroD1 nucleic acid that is operable in aspects of the present invention including a NeuroD1 nucleic acid.

A nucleic acid probe or primer able to hybridize to a target NeuroD1 mRNA or cDNA can be used for detecting and/or quantifying mRNA or cDNA encoding NeuroD1 protein. A nucleic acid probe can be an oligonucleotide of at least 10, 15, 30, 50 or 100 nucleotides in length and sufficient to specifically hybridize under stringent conditions to NeuroD1 mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof.

The terms "complement" and "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, SEQ ID NO: 1 and SEQ ID NO: 3 will hybridize to the complement of substantially identical targets and not to unrelated sequences.

Methods of Treating a Neurological Condition

Methods of treating a neurological condition in a subject in need thereof are provided according to aspects of the present invention which include delivering a therapeutically effective amount of NeuroD1 to glial cells of the central nervous system or peripheral nervous system of the subject, the therapeutically effective amount of NeuroD1 in the glial cells results in a greater number of neurons in the subject compared to an untreated subject having the same neurological condition, whereby the neurological condition is treated.

The conversion of reactive glial cells into neurons also reduces neuroinflammation and neuroinhibitory factors associated with reactive glial cells, thereby making the glial scar tissue more permissive to neuronal growth so that neurological condition is alleviated.

The term "neurological condition" as used herein refers to any condition of the central and/or peripheral nervous system of a subject which is alleviated, ameliorated or prevented by additional neurons. Injuries or diseases which result in loss or inhibition of neurons and/or loss or inhibition of neuronal function are neurological conditions for treatment by methods according to aspects of the present invention.

Injuries or diseases which result in loss or inhibition of glutamatergic neurons and/or loss or inhibition of glutaminergic neuronal functions are neurological conditions for treatment by methods according to aspects of the present invention. Loss or inhibition of other types of neurons, such as GABAergic, cholinergic, dopaminergic, norepinephrinergic, or seratonergic neurons can be treated with the similar method.

Thus, for example, injuries or diseases which result in loss or inhibition of neurons and/or loss or inhibition of neuronal functions including, but not limited to, Alzheimer's disease, Parkinson disease, Amyotrophic lateral sclerosis (ALS), stroke, epilepsy, physical injury such as brain or spinal cord injury, and tumor, are neurological conditions for treatment by methods according to aspects of the present invention.

The term "therapeutically effective amount" as used herein is intended to mean an amount of an inventive composition which is effective to alleviate, ameliorate or prevent a symptom or sign of a neurological condition to be treated. In particular embodiments, a therapeutically effective amount is an amount which has a beneficial effect in a subject having signs and/or symptoms of a neurological condition.

The terms "treat," "treatment," and "treating" as used herein refer to alleviating, inhibiting or ameliorating a neurological condition, symptoms or signs of a neurological condition, and preventing symptoms or signs of a neurological condition, and include, but are not limited to therapeutic and/or prophylactic treatments.

Signs and symptoms of neurological conditions are well-known in the art along with methods of detection and assessment of such signs and symptoms.

Method of treating a neurological condition in a subject in need thereof are provided according to aspects of the present invention which include providing a viral vector comprising a nucleic acid encoding NeuroD1; and delivering the viral vector to the central nervous system or peripheral nervous system of the subject, whereby the viral vector infects glial cells of the central nervous system or peripheral nervous system, respectively, producing infected glial cells and whereby exogenous NeuroD1 is expressed in the infected glial cells at a therapeutically effective level, wherein the expression of NeuroD1 in the infected cells results in a greater number of neurons in the subject compared to an untreated subject having the same neurological condition, whereby the neurological condition is treated. In addition to the generation of new neurons, the number of reactive glial cells will also be reduced, resulting in less neuroinhibitory factors released, thereby making local environment more permissive to neuronal growth or axon penetration, hence alleviating neurological conditions.

Administration of a pharmaceutical composition to the central nervous system or peripheral nervous system of a subject is accomplished by methods including systemic or local administration.

According to aspects of the present invention, a viral vector comprising a nucleic acid encoding NeuroD1 is delivered by injection into the central nervous system or peripheral nervous system of a subject, such as by intracerebral injection, spinal cord injection and/or injection into the cerebrospinal fluid. Alternative viral delivery methods include but not limited to intravenous injection and intraperitoneal injection.

Combinations of therapies for a neurological condition of a subject are administered according to aspects of the present invention.

The term "subject" refers to humans and also to non-human mammals such as, but not limited to, non-human primates, cats, dogs, sheep, goats, horses, cows, pigs and rodents, such as but not limited to, mice and rats; as well as to non-mammalian animals such as, but not limited to, birds, poultry, reptiles, amphibians.

Embodiments of inventive compositions and methods are illustrated in the following examples. These examples are provided for illustrative purposes and are not considered limitations on the scope of inventive compositions and methods.

EXAMPLES

Example 1

Mouse Cortical Astrocyte and NG2 Culture

For astrocyte culture, postnatal (P3-P5) mouse cortical tissue was dissociated and plated onto 25 cm$^2$ flasks. Cells were cultured for 5-6 days, and flasks were rigorously shaken daily to remove neurons and non-astrocytic cells. After reaching confluence, astrocytes were centrifuged for 5 mM at 1,000 rpm, re-suspended, and plated on poly-D-lysine (Sigma) coated coverslips (12 mm). Astrocyte culture medium contained DMEM/F12 (Gibco), 10% fetal bovine serum (Gibco), penicillin/streptomycin (Gibco), 3.5 mM glucose (Sigma), and supplemented with B27 (Gibco), 10 ng/mL epidermal growth factor (EGF, Invitrogen), and 10 ng/mL fibroblast growth factor 2 (FGF2, Invitrogen).

For mouse NG2 culture, the cortical tissue of postnatal mice (P3-P5) was dissociated and plated in 25 cm$^2$ flasks coated with poly-D-lysine (Sigma). The cells were maintained in DMEM/F12 (Gibco) with 10% fetal bovine serum (Gibco) for 9 days, with a medium change every 3 days. On the 9$^{th}$ day, the flasks were shaken rigorously and the supernatant was collected and centrifuged to harvest NG2 cells with a small number of neurons and microglia cells. After centrifuge, cells were resuspended and seeded on poly-D-lysine (Sigma) coated coverslips (12 mm). The cells were cultured in serum-free DMEM medium (Gibco) with N2 supplements (STEMCELL™) and 10 ng/ml platelet-derived growth factor (PDGF, Invitrogen), 10 ng/mL epidermal growth factor (EGF, Invitrogen), and 10 ng/mL fibroblast growth factor 2 (FGF2, Invitrogen) for 3 days. Cells were maintained at 37° C. in humidified air with 5% $CO_2$. Mouse neuronal culture was the same as described in Wu, X. et al., J. Biol. Chem., 287(33):27417-27430, 2012.

Example 2

Human Cortical Astrocyte and Microglia Culture

Human cortical astrocytes (HA1800) were purchased from ScienCell (California). Cells were subcultured when they were over 90% confluent. For subculture, cells were trypsinized by TrypLE™ Select (Invitrogen), centrifuged for 5 min at 1,000 rpm, re-suspended, and plated in a medium consisting of DMEM/F12 (Gibco), 10% fetal bovine serum (Gibco), penicillin/streptomycin (Gibco), 3.5 mM glucose (Sigma), and supplemented with B27 (Gibco), 10 ng/mL epidermal growth factor (EGF, Invitrogen), and 10 ng/mL fibroblast growth factor 2 (FGF2, Invitrogen). The astrocytes were cultured on poly-D-lysine (Sigma) coated coverslips (12 mm) at a density of 50,000 cells per coverslip in 24-well plates (BD Biosciences). Human primary microglial cells were obtained from Clonexpress, Inc. (Maryland). The cells were cultured in DMEM/F-12 (Gibco) supplemented with 5% FBS, 10 ng/ml of macrophage colony-stimulating factor (M-CSF, Invitrogen), 10 ng/mL epidermal growth factor (EGF, Invitrogen), and 10 ng/mL fibroblast growth factor 2 (FGF2, Invitrogen). Cells were maintained at 37° C. in humidified air with 5% $CO_2$.

Example 3

Retrovirus Production

The mouse NeuroD1 gene was subcloned from the pAd NeuroD-I-nGFP construct, described in Zhou, Q. et al., Nature 455(7213):627-632, 2008 (Addgene) and inserted into a pCAG-GFP-IRES-GFP retroviral vector described in Zhao, C. et al., J. Neurosci., 26(1):3-11, 2006 to generate pCAG-NeuroD1-IRES-GFP retroviral vector. The sequence of CAG-NeuroD1-IRES-GFP is shown herein as SEQ ID NO:9. A control retrovirus construct, pCAG-GFP, encodes GFP and not NeuroD1.

The human GFAP promoter gene was subcloned from hGFAP Promoter-Cre-MP-1 (Addgene) and replaced the CAG promoter to generate pGFAP-NeuroD1-IRES-GFP and pGFAP-GFP-IRES-GFP retroviral vectors.

The human NG2 promoter was subcloned and replaced the CAG promoter to generate hNG2-NeuroD1-IRES-GFP and hNG2-GFP-IRES-GFP retroviral vectors.

The mouse Lcn2 promoter was subcloned and replaced the CAG promoter to generate mLen2-NeuroD1-IRES-GFP and mLcn2-GFP-IRES-GFP retroviral vectors. Reactive glial cells typically have high expression of Lcn2, an inflammation marker after injury.

The mouse Aldh1L1 promoter was subcloned and replaced the CAG promoter to generate mAldh1L1-NeuroD1-IRES-GFP and mAldh1L1-GFP-IRES-GFP retroviral vectors. Reactive glial cells typically have high expression of Aldh1L1.

The nucleic acid encoding GFP is not included for expression of NeuroD1 without GFP. Similarly, when only NeuroD1 is to be expressed, the IRES need not be included in the construct.

Viral particles were packaged in gpg helperfree HEK (human embryonic kidney) cells to generate VSV-G (vesicular stomatitis virus glycoprotein)-pseudotyped retroviruses encoding neurogenic factors in CellMax™ hollow fiber cell culture system (Spectrum Laboratories). The titer of viral particles was about $10^8$ particles/µl, determined after transduction of HEK cells.

Example 4

Trans-Differentiation of Glial Cells into Neurons

Twenty-four hours after infection of astrocytes, NG2 cells, or microglia with GFP or NeuroD1 retrovirus, the culture medium was completely replaced by a differentiation medium including DMEM/F12 (Gibco), 0.5% FBS (Gibco), 3.5 mM glucose (Sigma), penicillin/streptomycin (Gibco), and N2 supplement (Gibco). Brain-derived neurotrophic factor (BDNF, 20 ng/mL, Invitrogen) was added to the cultures every four days during the differentiation to promote synaptic maturation as described in Song, H. et al., Nature, 417(6884):39-44, 2002. Due to the morphological change from astrocytes or NG2 cells to neurons during conversion, the empty space was filled with additional human or mouse astrocytes to support the functional development of converted neurons.

Example 5

Gap Junction Assay

Sulforhodamine B (SRB, 558 Da, 2 mM) was added to the pipette solution for dye dialysis into cells. Whole-cell recordings were made on newly converted neurons infected by NeuroD1-GFP (1-3 DPI), and dye dialysis was held for a 20-min period. The dye spreading was observed under 40× objective lens. To block gap junctions, carbenoxolone (CBX, 100 µM, Sigma) was added into differentiation medium and changed every 2 days. To induce cell death in astrocyte culture, cells were treated with 100 µM LPS for 6 hours.

Example 6

Animals and In Vivo Assays

In vivo experiments were conducted on wild-type C57/BL6 and a 5xFAD transgenic mouse model of Alzheimer disease, referred to herein as "AD transgenic mice." AD transgenic mice were purchased from The Jackson Laboratory (B6SJL-Tg (APPSwFlLon,PSEN1*M146L*L286V) 6799Vas/Mmjax), described in Oakley, H. et al., J. Neurosci., 26(40):10129-10140, 2006, and mated with C57/BL6 mice. Mice were housed in a 12 hr light/dark cycle and supplied with enough food and water.

Example 7

Stereotaxic Viral Injection

Surgeries were performed on 1, 5-7 and 14 months old WT mice, and on 5-7 and 14 month old AD mice for virus injection or pure stab injury. The mice were anesthetized by injecting 20 mL/kg 2.5% Avertin (a mixture of 25 mg/ml of Tribromoethylethanol and 25 µl/ml T-amyl-alcohol) into the peritoneum and then placed in a stereotaxic setup. Artificial eye ointment was applied to cover and protect the eye. The animals were operated with a midline scalp incision and a drilling hole on the skulls above somatosensory cortex. Each mouse received injection (site: AP 1.25 mm, ML 1.4 mm, DV −1.5 mm) of virus with a 5 µl syringe and a 34 gauge needle. The injection volume and flow rate were controlled as 3 µl at 0.2 µl/min, and the needle was moved up during the injection at speed of 0.1 mm/min. After injection, the needle was kept for at least 5 additional minutes and then slowly withdrawn. The needle injection itself was used as stab injury model.

Example 8

Immunocytochemistry

For brain section staining, the mice were anesthetized with 2.5% Avertin and then sequentially perfused, first with saline solution (0.9% NaCl) to wash the blood off and then with 4% paraformaldehyde (PFA) to fix the brain. The brains were removed and post fixed in 4% PFA overnight at 4°, and then cut at 45 μm sections by a vibratome (Leica). For analyzing blood vessel area, the animals were perfused by 10 KD Lysine Fixable dextran-Texas red (Invitrogen, 0.5 ml of 10 mg/ml) after fixation. Coronal brain sections were first pretreated in 0.3% Triton X-100 in phosphate-buffered saline (PBS, pH 7.4) for 1 hour, followed by incubation in 3% normal goat serum, 2% normal donkey serum and 0.1% Triton X-100 in PBS for 1 hour.

For cell culture staining, the cultures were fixed in 4% PFA in PBS for 15 min at room temperature. Cells were first washed three times by PBS and then pretreated in 0.1% Triton X-100 in PBS for 30 min, followed by incubation in 3% normal goat serum, 2% normal donkey serum and 0.1% Triton X-100 in PBS for 1 hour. Primary antibodies were incubated with either brain slices or cultures overnight at 4° C. in 3% normal goat serum, 2% normal donkey serum and 0.1% Triton X-100 in PBS. After additional washing in PBS, the samples were incubated with appropriate secondary antibodies conjugated to Alexa Fluor 488, Alexa 546, Alexa 647 (1:300, Molecular Probes), FITC, TRITC, or Dylight (1:500, Jackson ImmunoResearch) for 1 h at room temperature, followed by extensive washing in PBS. Coverslips were finally mounted onto a glass slide with an anti-fading mounting solution with DAPI (Invitrogen). Slides were first examined with an epifluorescent microscope (Nikon TE-2000-S) and further analyzed with a confocal microscope (Olympus FV1000). Z-stacks of digital images, which can either release single confocal images or collapse as one resulting picture, were acquired and analyzed using FV10-ASW 3.0 Viewer software (Olympus).

The following primary antibodies were used: polyclonal anti-green fluorescent protein (GFP, chicken, 1:1000, Abcam, AB13970), polyclonal anti-Glial Fibrillary Acidic Protein (GFAP, rabbit, 1:500, Abcam, Z0334), polyclonal anti-Glial Fibrillary Acidic Protein (GFAP, chicken, 1:500, Millipore, AB5541), monoclonal anti S100β (mouse, 1:500, Abcam, ab66028) monoclonal anti-Red Fluorescent Protein (RFP, mouse, 1:300, CELL BIOLABS), polyclonal anti-Red Fluorescent Protein (RFP, rabbit, 1:2000, Rockland), polyclonal anti-vesicular glutamate transporter 1 (vGluT1, rabbit, 1:500, Synaptic Systems), polyclonal anti-vesicular glutamate transporter (SV2, rabbit, 1:2000, Developmental Studies Hybridoma Bank, Iowa City), polyclonal anti-Microtubule Associated Protein 2 (MAP2, Chicken, 1:1000, Abcam, AB5392), polyclonal anti-Microtubule Associated Protein 2 (MAP2, rabbit, 1:500, Chemicon, AB5622), polyclonal anti-T-box, brain, 1 (Tbr1, 1:300, rabbit, Abcam, AB31940), polyclonal anti-Prox1 (rabbit, 1:1000, ReliaTech GmbH, 102-PA32), polyclonal anti-musashi-1 (rabbit, 1:300, Neuromics, RA14128), monoclonal anti-SRY (sex determining region Y)-box 2 (Sox-2, mouse, 1:300, Abcam, AB79351), polyclonal anti-SRY (sex determining region Y)-box 2 (Sox-2, rabbit, 1:500, Millipore, AB5603), monoclonal anti-GAD6, monoclonal anti-βIII tubulin (Tuj1, mouse, 1:500, COVANCE, MMS-435P), polyclonal anti-Doublecortin (DCX, rabbit, 1:500, Abcam, AB18723), monoclonal anti-beta Amyloid (Aβ, mouse, 1:200, Abcam, AB11132), monoclonal anti-beta Amyloid 1-42 (rabbit, 1:1000, Invitrogen, 700524), monoclonal anti-ApoE [D6E10] (mouse, 1:200. Abcam, AB1906) polyclonal anti-NeuN (rabbit, 1:500, Millipore, ABN78), monoclonal anti-NG2 (mouse, 1:200, Abcam, AB50009), polyclonal anti-Iba1 (goat, 1:200, Abcam, AB5076), polyclonal anti-Iba1 (rabbit, 1:1000, Wako, 019-19741), monoclonal anti-CNPase (mouse, 1:200, Abcam, AB6319), monoclonal anti-Chondroitin sulfate proteoglycan (CSPG, 1:200, mouse, Sigma, C8035), monoclonal anti-Vascular endothelial growth factor (VEGF, 1:500, mouse, Abcam, AB1316), monoclonal anti-Pan-Axonal Neurofilament Marker (SMI 312, 1:1000, mouse, Covance, SMI-312R), polyclonal anti-Glial Glutamate Transporter GLT-1 (EAAT2) (Glt1, Guinea pig, 1:2000, Millipore, AB1783), polyclonal anti-Connexin 43 (Cx43, rabbit, 1:1000, Abcam, AB11370), monoclonal anti-BrdU (mouse, 1:500, Dako, 074401-8), monoclonal anti-NeuroD1 (mouse, 1:1000, Abcam, ab60704), polyclonal-MBP (rabbit, 1:300, Millipore, AB908), polyclonal anti-GABA (rabbit, 1:2000, Sigma, A2052), and monoclonal anti-glutamate (mouse, 1:500, Sigma, G9282).

Example 9

BrdU Immunohistochemistry 100 mg/kg of BrdU (5-bromo-2-deoxyuridine; Invitrogen) was administered to stab-injured mice through intraperitoneal injection for 3 consecutive days starting from 2 days post injury (DPI) to 4 DPI. Mice were euthanized at 4 DPI or 1 month post injury. Floating brain sections were immersed in 85-90° C. 1× citrate buffer (Sigma # C9999) for 15 min and cool down to room temperature (RT) for 20 min. After wash with PBS for 3 times, brain sections were treated with 2 M HCl at 37° C. for 20 min and washed with PBS for 6 times. Then, brain slices were permeabilized with 0.3% triton in PBS at RT for 2 hours and blocked in blocking buffer (2.5% normal donkey serum, 2.5% normal goat serum, 0.1% triton in PBS) for 1 hour at RT. Sections were incubated in primary anti-BrdU (Dako, 1:500) antibody overnight at 4° C. overnight.

Example 10

TUNEL Assay

The TUNEL assay was performed with floating brain sections or fixed cell culture to detect apoptotic cells. The In Situ Cell Death Detection Kit (Roche, Laval, Quebec, Canada) was used according to manufacturer's instruction. Briefly, enzyme solution and label solution were 1:9 mixed to obtain TUNEL reaction mixture. Brain sections were incubated with TUNEL reaction mixture at 37° C. for 1 hour. After incubation, brain sections were rinsed with PBS for 3 times. TUNEL signal was detected under fluorescent microscope using the detection wavelength of 570-620 nm.

Example 11

Patch-Clamp Recordings in Cell Cultures

For NeuroD1-converted neurons, whole-cell recordings were performed using Multiclamp 700A patch-clamp amplifier (Molecular Devices, Palo Alto, Calif.) as described in Deng, L. et al., J. Neurosci., 27(40):10860-10869, 2007, and the chamber was constantly perfused with a bath solution consisting of 128 mM NaCl, 30 mM glucose, 25 mM HEPES, 5 mM KCl, 2 mM $CaCl_2$, and 1 mM $MgCl_2$. The pH of bath solution was adjusted to 7.3 with NaOH, and osmolarity at 315-325 mOsm/L. Patch pipettes were pulled from borosilicate glass (4-5 MΩ) and filled with a pipette solution consisting of 135 mM KCl (or 10 mM KCl+125 mM K-Gluconate), 5 mM Na-phosphocreatine, 10 mM HEPES, 2 mM EGTA, 4 mM MgATP, and 0.5 mM Na$_2$GTP, pH 7.3 adjusted with KOH. To distinguish EPSCs versus IPSCs, 0 mM Cl$^-$ (135 mM K-Gluconate) pipette solution was also used. The series resistance was typically 10-25 MΩ. For voltage-clamp experiments, the membrane potential was typically held at −70 or −80 mV. Drugs were applied through a gravity-driven drug delivery system (VC-6, Warner Hamden, CT). NMDA currents were recorded in Mg$^{2+}$ free bath solution (128 mM NaCl, 30 mM D-glucose, 25 mM HEPES, 5 mM KCl, and 2 mM CaCl$_2$, pH 7.3, adjusted with NaOH) plus 10 μM glycine, 0.5 μM TTX, and 20 μM BIC. Data were acquired using pClamp 9 software (Molecular Devices, Palo Alto, Calif.), sampled at 10 kHz and filtered at 1 kHz. Na$^+$ and K$^+$ currents and action potentials were analyzed using pClamp 9 Clampfit software. Spontaneous synaptic events were analyzed using MiniAnalysis software (Synaptosoft, Decator, Ga.). All experiments were conducted at room temperature.

Example 12

Brain Slice Recordings

Cortical slices were prepared typically 1 month after virus injection and cut at 300 μm thick coronal slices with a Leica vibratome in ice cold cutting solution (containing 75 mM sucrose, 87 mM NaCl, 2.5 mM KCl, 0.5 mM CaCl$_2$, 7 mM MgCl$_2$, 25 mM NaHCO$_3$, 1.25 mM NaH$_2$PO4 and 20 mM glucose). Slices were maintained in artificial cerebral spinal fluid (ACSF) containing 119 mM NaCl, 2.5 mM KCl, 1.25 mM NaH$_2$PO$_4$, 26 mM NaHCO$_3$, 1.3 mM MgCl$_2$, 2.5 mM CaCl$_2$ and 10 mM glucose. Slices were incubated in ACSF, continuously bubbled with 95% O$_2$ and 5% CO$_2$, first at 34° C. for 30 minutes, and then at room temperature. Whole-cell recordings were performed using a pipette solution containing 135 mM K-Gluconate, 10 mM KCl, 5 mM Na-phosphocreatine, 10 mM HEPES, 2 mM EGTA, 4 mM MgATP, and 0.5 mM Na$_2$GTP (pH 7.3 adjusted with KOH, 290 mOsm/L). Pipette resistance was 3-4 MΩ, and series resistance was typically 20-40 MΩ. The holding potential for voltage-clamp experiments was −70 mV. Data were collected using pClamp 9 software (Molecular Devices, Palo Alto, Calif.), sampled at 10 kHz and filtered at 1 kHz, analyzed with Clampfit and Synaptosoft softwares.

Example 13

Data Analysis

Cell counts were performed by taking images of several randomly chosen views per coverslip and analyzed by Image J software. The intensity or pixel area was analyzed by Image J software. Data were represented as mean±SEM. Student's t-test (paired or unpaired) was used for statistical analysis. *P<0.05, P<0.01, *P<0.001.

Example 14

Figure 5A:
FIG. 5A is a set of low power images showing GFP retrovirus-infected reactive glial cells in the vicinity of injury core shown at 14 DPI.

In Vivo Conversion of Reactive Astrocytes and NG2 Cells into Functional Neurons after Brain Injury Injecting control retrovirus encoding only GFP into mouse cortex revealed GFAP-positive reactive astrocytes in the injury site at 14 days post injection, DPI. 52.1±4.3% of the GFP-positive cells were GFAP-positive, n=3 animals, see FIG. 1A and also FIG. 5A. FIG. 1A shows representative images illustrating GFP fluorescence in the left panel, GFAP immunofluorescence in the same field, shown in the middle panel, and the overlap of GFP fluorescence and GFAP immunofluorescence in the same field, shown in the right panel, scale bar, 20 μm.

Figure 1B:
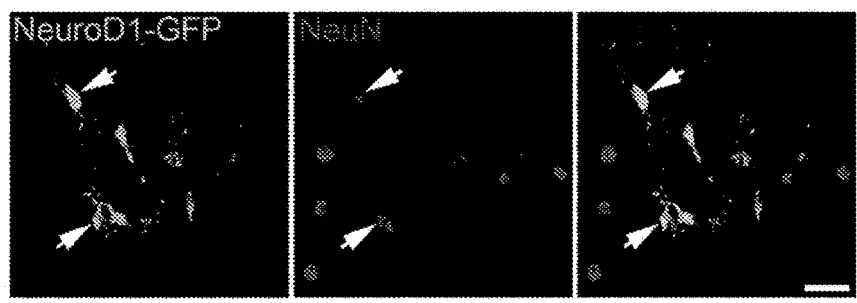
FIG. 1B shows representative images illustrating NeuroD1-GFP fluorescence in the left panel, NeuN immunofluorescence in the same field, shown in the middle panel, and the overlap of NeuroD1-GFP fluorescence and NeuN immunofluorescence in the same field, shown in the right panel.
Figure 5B:
FIG. 5B shows NeuroD1-GFP fluorescence along with DCX immunostaining of the same field, middle and overlap of GFP fluorescence and DCX immunostaining of the same field, right.
Figure 5C:
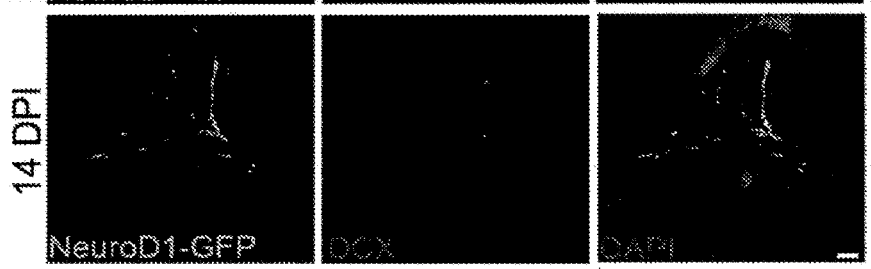
FIG. 5C shows low power images of DCX-positive cells infected by NeuroD1-GFP along the injection site at 14 DPI.
Figure 5D:
FIG. 5D are high power images showing DCX-positive cells infected by NeuroD1-GFP along the injection site at 14 DPI.

Cells infected with a retrovirus construct encoding both NeuroD1 and GFP showed extensive neurites and were immunopositive for neuronal marker NeuN at 7 DPI, FIG. 1B, see also FIG. 5B-D; n=6 animals. FIG. 1B shows representative images illustrating NeuroD1-GFP fluorescence in the left panel, NeuN immunofluorescence in the same field, shown in the middle panel, and the overlap of NeuroD1-GFP fluorescence and NeuN immunofluorescence in the same field, shown in the right panel, scale bar, 20 μm. The term "NeuroD1-GFP fluorescence" as used in the Examples herein refers to GFP fluorescence detected in cells infected with a retrovirus construct encoding both NeuroD1 and GFP, such that the GFP fluorescence is a surrogate marker for expression of NeuroD1. In particular cases, expression of NeuroD1 was independently verified using an anti-NeuroD1 antibody assay, examples of which are described and/or shown herein. Note the significant number of NeuN-positive neurons in the injury site after infection with retrovirus construct pCAG-NeuroD1-IRES-GFP.

Figure 1C:
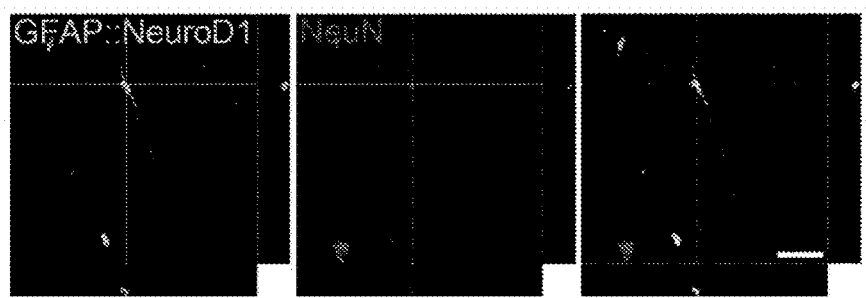
FIG. 1C shows representative images illustrating GFAP promoter-driven NeuroD1-GFP fluorescence in the left panel, NeuN immunofluorescence in the same field, shown in the middle panel, and the overlap of GFAP promoter-driven NeuroD1-GFP fluorescence and NeuN immunofluorescence in the same field, shown in the right panel.

Following injection of a retrovirus encoding NeuroD1 under the control of human GFAP promoter, called hGFAP::NeuroD1-IRES-GFP, into adult mouse cortex, which typically has no adult neural stem cells, NeuroD1-infected cells with clear neuronal morphology and immunopositive for NeuN were found, see FIG. 1C; n=3 animals. Cells infected with hGFAP::NeuroD1-IRES-GFP in which GFAP promoter-driven NeuroD1 and GFP were produced were immunopositive for NeuN and extended long neurites at 7 DPI. FIG. 1C shows representative images illustrating GFAP promoter-driven NeuroD1-GFP fluorescence in the left panel, NeuN immunofluorescence in the same field, shown in the middle panel, and the overlap of GFAP promoter-driven NeuroD1-GFP fluorescence and NeuN immunofluorescence in the same field, shown in the right panel, scale bar, 40 μm. In contrast, injecting control retrovirus hGFAP::GFP which encodes GFP and not NeuroD1 did not result in any neuronal conversion, see FIG. 5E; n=3 animals.

Figure 1D:
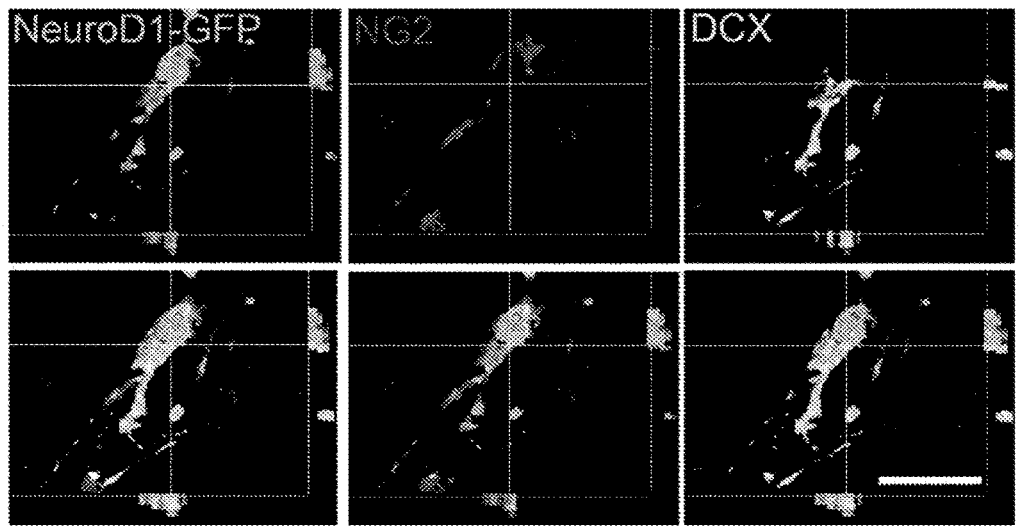
FIG. 1D shows representative images at 2 DPI illustrating NeuroD1-GFP fluorescence in the left panel, NG2 immunofluorescence in the same field, shown in the middle panel, and DCX immunofluorescence shown in the right panel.

Besides reactive astrocytes, brain injury also activates other two types of reactive glial cells, NG2 cells and microglia. Both astrocytes and NG2 cells are originated from neural stem cell lineage, while microglia is generated by hematopoietic stem cells and infiltrated into the brain through blood vessels. A small percentage (4.7±2%, n=7 animals) of cells newly infected by retroviral vector pCAG-NeuroD1-IRES-GFP, i.e. at 2 DPI, were found to be immunopositive for both NG2 and Doublecortin (DCX, an immature neuronal marker). FIG. 1D shows representative images at 2 DPI illustrating NeuroD1-GFP fluorescence in the left panel, NG2 immunofluorescence in the same field, shown in the middle panel, and DCX immunofluorescence shown in the right panel, scale bar, 20 μm.

Figure 1E:
FIG. 1E shows representative images illustrating NeuroD1-GFP fluorescence in the left panel, NeuN immunofluorescence in the same field, shown in the middle panel, and the overlap of NeuroD1-GFP fluorescence and NeuN immunofluorescence in the same field, shown in the right panel.

After 21 DPI, the in-vivo NeuroD1-converted neurons after brain injury were NeuN-positive and showed robust dendrites and potential axons. FIG. 1E shows representative images illustrating NeuroD1-GFP fluorescence in the left panel, NeuN immunofluorescence in the same field, shown in the middle panel, and the overlap of NeuroD1-GFP fluorescence and NeuN immunofluorescence in the same field, shown in the right panel. NeuroD1-converted neurons are shown to be NeuN-positive, arrowhead, having robust dendrites and a potential axon is shown at the arrow, scale bar, 20 μm.

Figure 1F:
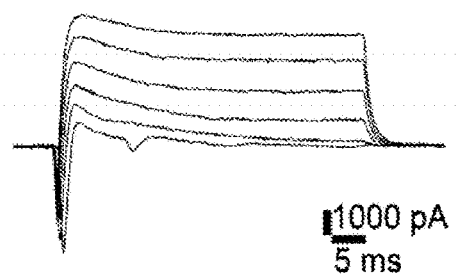
FIG. 1F shows a representative trace from cortical slice recordings showing $Na^+$ and $K^+$ currents in NeuroD1-converted neurons at 30 DPI. The NeuroD1-converted neurons were found to be capable of firing repetitive action potentials as well, n=4.
Figure 1G:
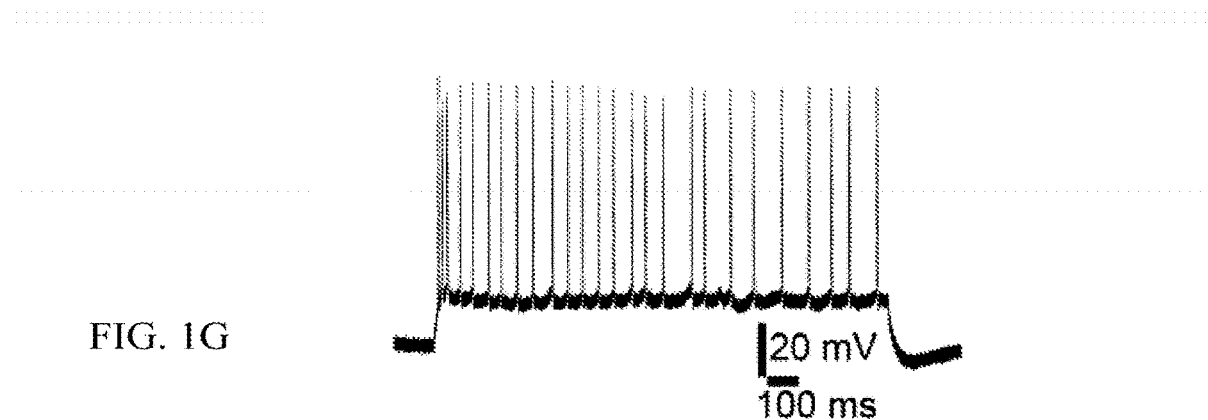
FIG. 1G shows a representative trace from cortical slice recordings showing repetitive action potentials in NeuroD1-converted neurons at 30 DPI.
Figure 1H:
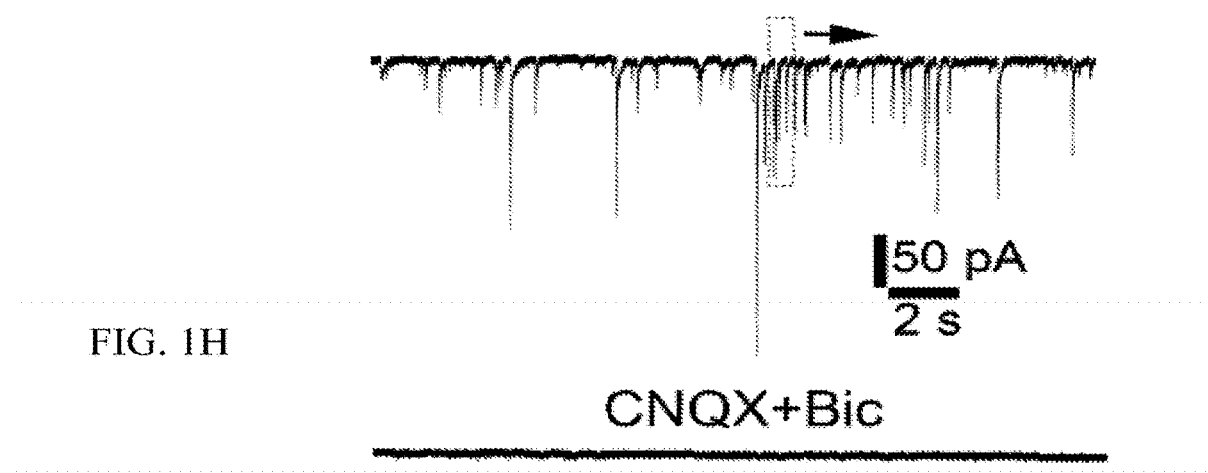
FIG. 1H shows representative traces showing spontaneous synaptic events in a NeuroD1-converted neuron in cortical slice recording at 26 DPI, CNQX, 10 µM; Bic, 20 µM.
Figure 1I:
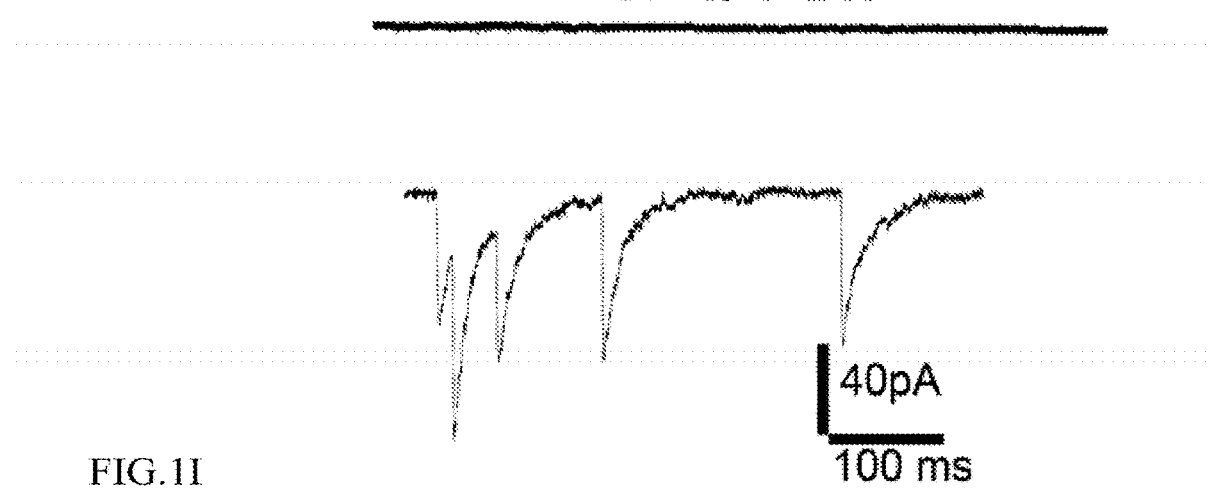
FIG. 1I shows an enlarged view of the synaptic events from FIG. 1H.

NeuroD1-converted neurons were found to be functional. Cortical slice recordings were performed on cells infected with retroviral vector pCAG-NeuroD1-IRES-GFP, which were identified as green under fluorescent microscope. The NeuroD1-converted neurons showed large sodium currents (3840±302 pA, n=5) and potassium currents (4672±602 pA, n=5). FIG. 1F shows a representative trace from cortical slice recordings showing Na$^+$ and K$^+$ currents in NeuroD1-converted neurons at 30 DPI. The NeuroD1-converted neurons were found to be capable of firing repetitive action potentials as well, n=4. FIG. 1G shows a representative trace from cortical slice recordings showing repetitive action potentials in NeuroD1-converted neurons at 30 DPI. Moreover, robust spontaneous synaptic events in NeuroD1-converted neurons were recorded in cortical slice recordings; frequency, 1.96±0.43 Hz; amplitude, 23.7±2.0 pA; n=8; 25-31 DPI, suggesting that they have been functionally incorporated into existing neural circuits. FIG. 1H shows representative traces showing spontaneous synaptic events in a NeuroD1-converted neuron in cortical slice recording at 26 DPI, CNQX, 10 µM; Bic, 20 µM. FIG. 1I shows an enlarged view of the synaptic events from FIG. 1H.

Example 15

Figure 2A:
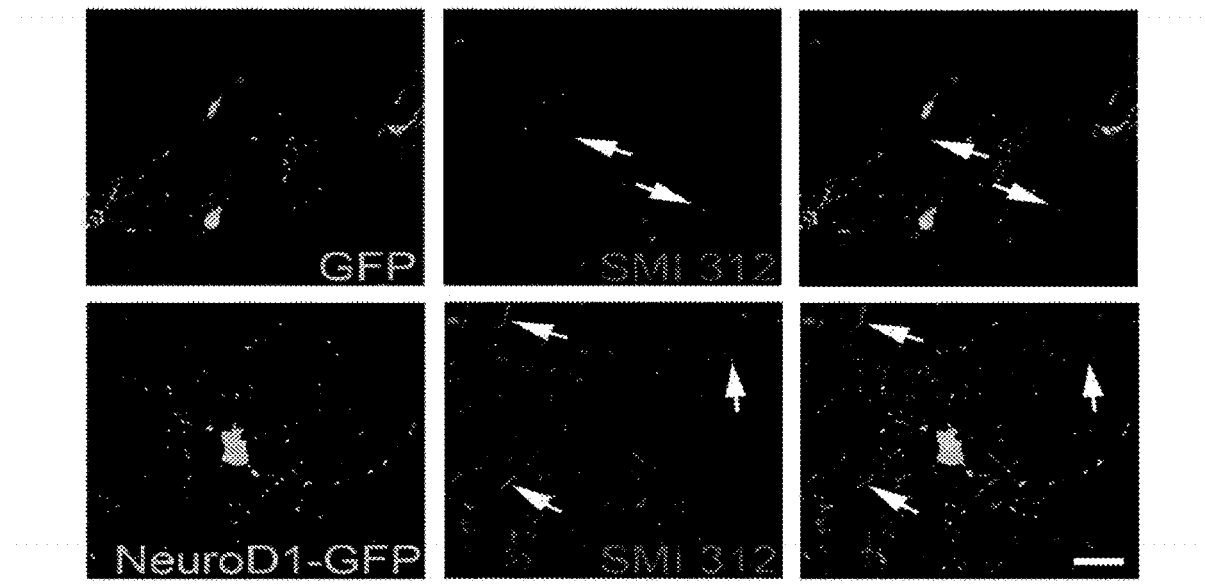
FIG. 2A shows representative images illustrating GFP fluorescence in cells infected with a retrovirus construct encoding GFP alone, top left or in cells infected with a retrovirus construct encoding NeuroD1-GFP, bottom left, immunofluorescence labels axons in the same fields, shown in the corresponding middle panels top and bottom.
Figure 2B:
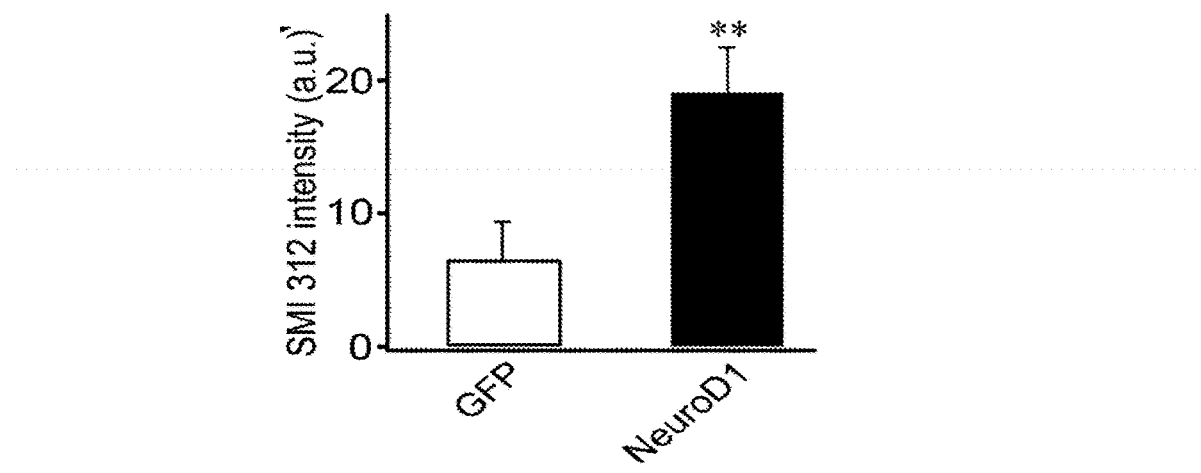
FIG. 2B is a graph showing results of quantitation of axon fibers in the injured region infected with retrovirus construct encoding NeuroD1-GFP showing NeuroD1-induced conversion.

Beneficial Effects of Converting Reactive Astrocytes and NG2 Cells into Functional Neurons after Brain Injury The effects of reactive glia-neuron conversion on the injury areas were examined. Axon fibers increased significantly in the injured region with infected with retrovirus construct pCAG-NeuroD1-IRES-GFP, compared to control areas infected with retrovirus construct pCAG-GFP. Consistent with the generation of new neurons in the injury site, axon fibers labeled by SMI312 increased significantly in the region infected with retroviral vector pCAG-NeuroD1-IRES-GFP compared to the region infected with the GFP control vector, n=9 animals. FIG. 2A shows representative images illustrating GFP fluorescence in cells infected with a retrovirus construct encoding GFP alone, pCAG-GFP, top left or in cells infected with retroviral vector pCAG-NeuroD1-IRES-GFP, bottom left, at 12-16 DPI. SMI 312 immunofluorescence labels axons in the same fields, shown in the corresponding middle panels top and bottom. The overlap of GFP fluorescence and SMI 312 immunofluorescence in the same field is shown in the corresponding right panels, scale bar, 20 µm. FIG. 2B is a graph showing results of quantitation of axon fibers in the injured region infected with retrovirus vector pCAG-NeuroD1-IRES-GFP showing NeuroD1-induced conversion, compared to the control injured region infected with pCAG-GFP, showing a significant increase in axon fibers in the injured region infected with retrovirus construct encoding NeuroD1-GFP (n=9).

Figure 2C:
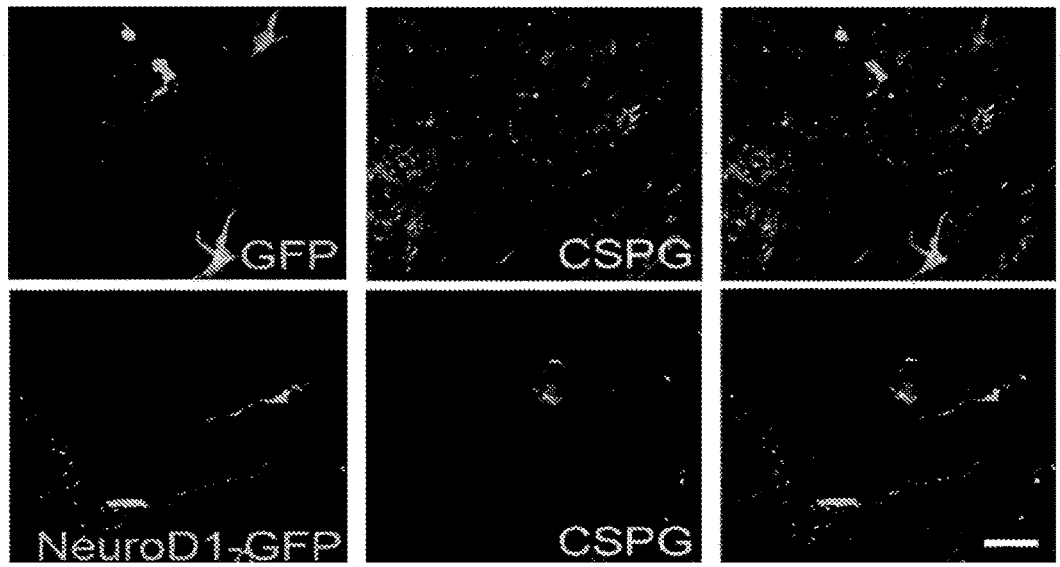
FIG. 2C shows representative images illustrating GFP fluorescence in cells infected with a retrovirus construct encoding GFP alone, top left or in cells infected with a retrovirus construct encoding NeuroD1-GFP, bottom left, CSPG immunofluorescence in the same fields is shown in the corresponding middle panels top and bottom.
Figure 2D:
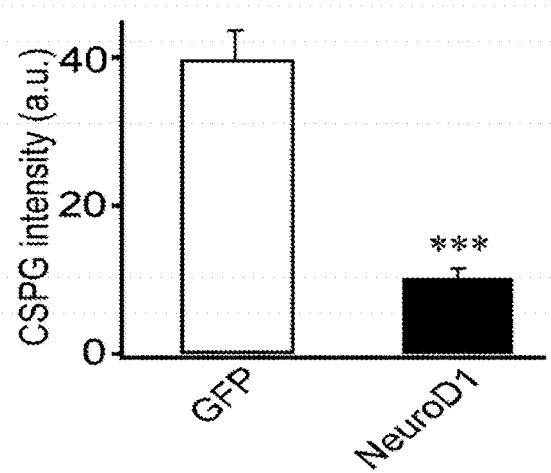
FIG. 2D is a graph showing results of quantitation of CSPG in the injured region infected with retrovirus construct encoding NeuroD1-GFP showing NeuroD1-induced conversion.

Glial cell secreted CSPG significantly decreased after NeuroD1-induced conversion, n=9 animals. FIG. 2C shows representative images illustrating GFP fluorescence in cells infected with a retrovirus construct encoding GFP alone, top left or in cells infected with retrovirus vector pCAG-NeuroD1-IRES-GFP, bottom left, at 12-16 DPI. CSPG immunofluorescence in the same fields is shown in the corresponding middle panels top and bottom. The overlap of GFP fluorescence and CSPG immunofluorescence in the same field is shown in the corresponding right panels, scale bar, 20 µm. FIG. 2D is a graph showing results of quantitation of CSPG in the injured region infected with retrovirus vector pCAG-NeuroD1-IRES-GFP showing NeuroD1-induced conversion, compared to the control injured region infected with retrovirus construct encoding GFP alone, showing a significant decrease in CSPG in the injured region infected with retrovirus vector pCAG-NeuroD1-IRES-GFP (n=9).

Figure 2E:
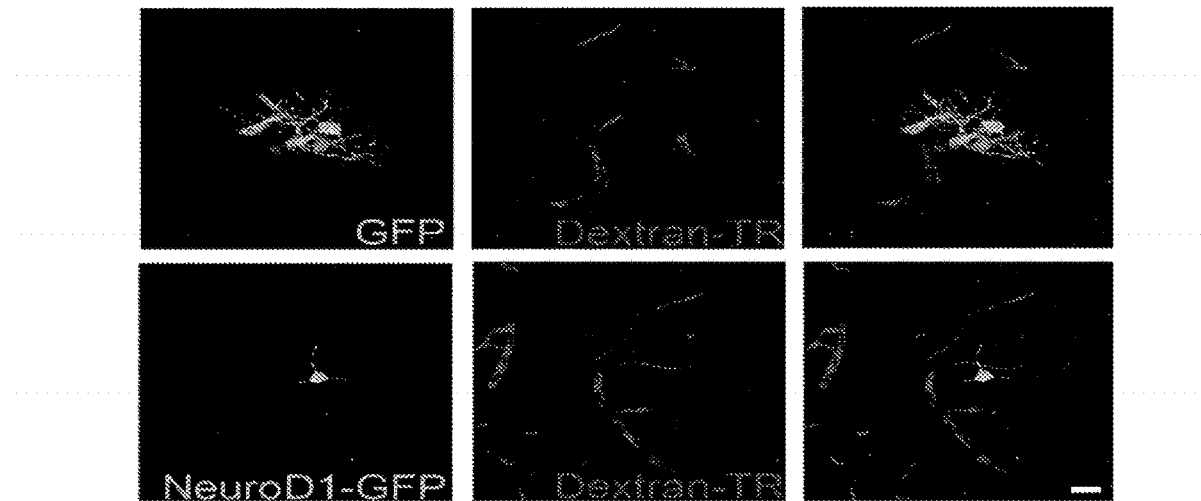
FIG. 2E shows representative images illustrating GFP fluorescence in cells infected with a retrovirus construct encoding GFP alone, top left or in cells infected with a retrovirus construct encoding NeuroD1-GFP, bottom left, Dextran-Texas Red (Dextran-TR) fluorescence labels blood vessels in the same fields, shown in the corresponding middle panels top and bottom.
Figure 2F:
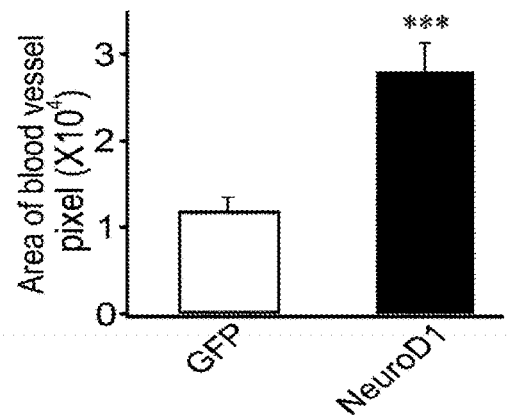
FIG. 2F is a graph showing results of quantitation of area of blood vessels in the injured region infected with retrovirus construct encoding NeuroD1-GFP showing NeuroD1-induced conversion.

In contrast, the blood vessels, labeled by dextran-Texas Red, significantly increased in the region infected with retrovirus vector pCAG-NeuroD1-IRES-GFP compared to the GFP control, n=6 animals. FIG. 2E shows representative images illustrating GFP fluorescence in cells infected with a retrovirus construct encoding GFP alone, top left or in cells infected with retrovirus construct pCAG-NeuroD1-IRES-GFP, bottom left, at 12-16 DPI. Dextran-Texas Red (Dextran-TR) fluorescence labels blood vessels in the same fields, shown in the corresponding middle panels top and bottom. The overlap of GFP fluorescence and Dextran-TR fluorescence in the same field is shown in the corresponding right panels, scale bar, 20 µm. FIG. 2F is a graph showing results of quantitation of area of blood vessels in the injured region infected with retrovirus construct pCAG-NeuroD1-IRES-GFP showing NeuroD1-induced conversion, compared to the control injured region infected with retrovirus construct encoding GFP alone, showing a significant increase in area of blood vessels in the injured region infected with retrovirus construct pCAG-NeuroD1-IRES-GFP (n=6).

Figure 2G:
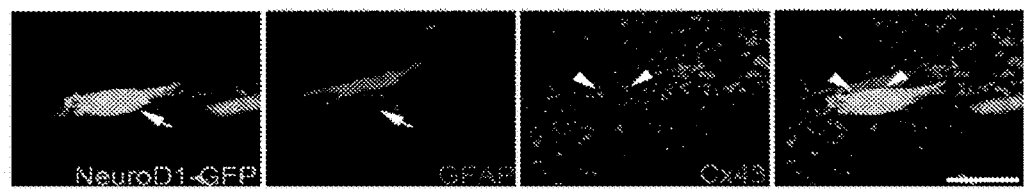
FIG. 2G shows representative images illustrating NeuroD1-GFP fluorescence in the left panel, GFAP immunofluorescence in the same field, shown in the middle left panel, arrow, Cx43 immunofluorescence in the same field shown in the middle right panel, arrowheads, and the overlap of NeuroD1-GFP fluorescence, GFAP immunofluorescence and Cx43 immunofluorescence in the same field, shown in the right panel.

At early stage of conversion, at 2 DPI, some cells infected with retrovirus construct pCAG-NeuroD1-IRES-GFP showed weak but clear GFAP expression (arrow). Gap junctions were detected at 2 DPI between astrocytes and newly converted neurons. FIG. 2G shows representative images illustrating NeuroD1-GFP fluorescence in the left panel, GFAP immunofluorescence in the same field, shown in the middle left panel, arrow, Cx43 immunofluorescence in the same field shown in the middle right panel, arrowheads, and the overlap of NeuroD1-GFP fluorescence, GFAP immunofluorescence and Cx43 immunofluorescence in the same field, shown in the right panel, scale bar, 10 µm.

Example 16

Figure 3A:
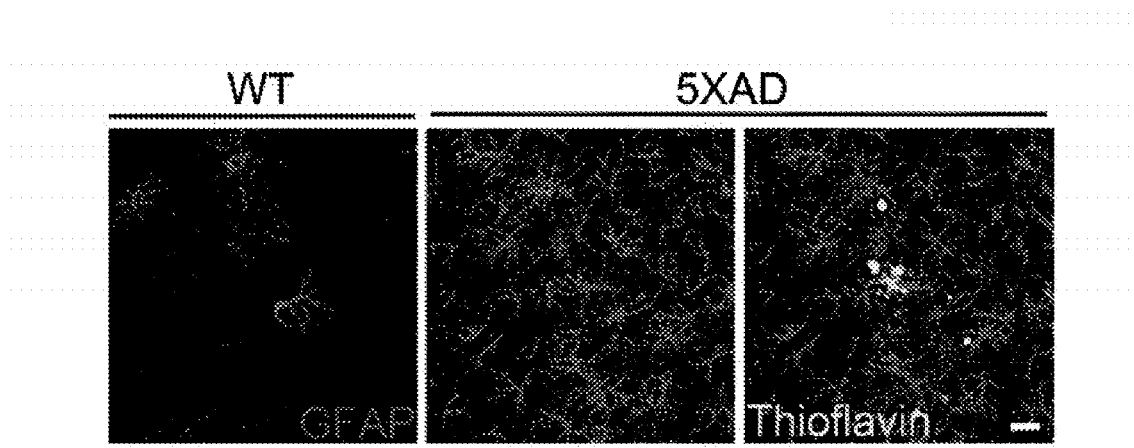
FIG. 3A shows representative images illustrating GFAP immunofluorescence in wild-type mouse cortex in the left panel, GFAP immunofluorescence in 5xFAD mouse cortex, shown in the middle panel, and the overlap of GFAP immunofluorescence in 5xFAD mouse cortex and thioflavin-S immunofluorescence in the same field, shown in the right panel.

NeuroD1 Converts Reactive Astrocytes and NG2 Cells into Functional Neurons (NeuroD1-Converted Neurons) in AD Mouse Brain In Vivo Reactive astrocytes have been widely reported in the cortex of Alzheimer's disease patients or animal models, see Steele, M. L. et al., Neurobiol. Aging, 33(2):423 e421-413, 2010; and Rodriguez, J. J. et al., Cell Death Differ., 16(3): 378-385, 2009. A transgenic mouse model with AD, 5xFAD, described in Oakley, H. et al., J. Neurosci., 26(40):10129-10140, 2006, was used in this example to test whether reactive astrocytes in the AD brain can be converted into functional neurons. Confirmation that there were indeed many reactive astrocytes in the cortex of 5xFAD mice (5 month old) compared to the WT was obtained. FIG. 3A shows representative images illustrating GFAP immunofluorescence in wild-type mouse cortex in the left panel, GFAP immunofluorescence in 5xFAD mouse cortex, shown in the middle panel, and the overlap of GFAP immunofluorescence in 5xFAD mouse cortex and thioflavin-S immunofluorescence in the same field, shown in the right panel, scale bar, 20 µm. Thioflavin-S labels Aβ plaques. Reactive astrocytes (labeled by GFAP) in 5xFAD mouse cortex were significantly increased compared to wild-type mouse cortex.

Figure 3B:
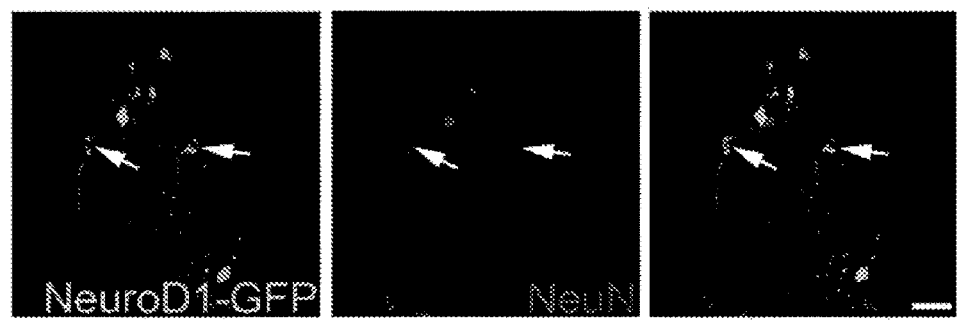
FIG. 3B shows representative images illustrating NeuroD1-GFP fluorescence in 7-month old 5xFAD mouse cortex in the left panel, NeuN immunofluorescence in the same field, shown in the middle panel, and the overlap of NeuroD1-GFP fluorescence and NeuN immunofluorescence in the same field, shown in the right panel.

Retrovirus pCAG-NeuroD1-IRES-GFP was injected into the cortex of 5xFAD mice and NeuN-positive neuron-like cells were subsequently found in the AD brain. Cells infected with retrovirus construct pCAG-NeuroD1-IRES-GFP at 14 DPI in AD mouse cortex (7-month old 5xFAD mouse cortex) showed clear neuron-like morphology and NeuN staining. FIG. 3B shows representative images at 14 DPI illustrating NeuroD1-GFP fluorescence in 7-month old 5xFAD mouse cortex in the left panel, NeuN immunofluorescence in the same field, shown in the middle panel, and the overlap of NeuroD1-GFP fluorescence and NeuN immunofluorescence in the same field, shown in the right panel, scale bar, 40 µm.

Figure 3C:
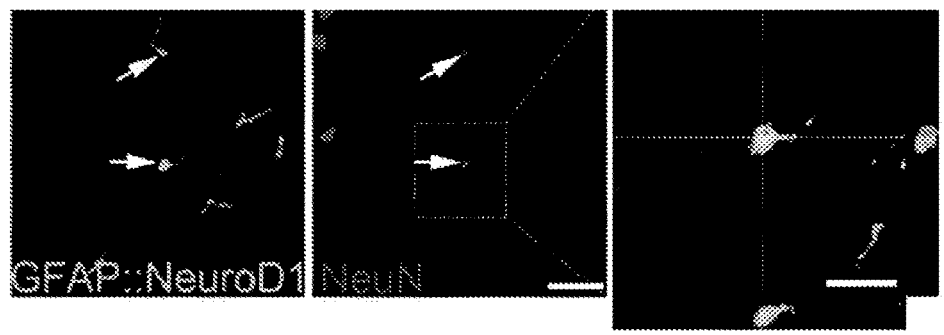
FIG. 3C shows representative images illustrating GFAP promoter-driven NeuroD1-GFP fluorescence in 5xFAD mouse cortex in the left panel, NeuN immunofluorescence in the same field, shown in the middle panel, and the overlap of GFAP promoter-driven NeuroD1-GFP fluorescence and NeuN immunofluorescence in the same field, shown in the right panel.

A retrovirus construct encoding NeuroD1-GFP driven by the human GFAP promoter, hGFAP::NeuroD1-GFP, was used to infect astrocytes specifically. NeuroD1-converted neurons labeled by NeuN in the AD brain were subsequently observed. AD cortex (5xFAD mouse cortex) infected by retrovirus encoding GFAP promoter-driven NeuroD1-GFP showed neuronal morphology and NeuN labeling at 7 DPI. FIG. 3C shows representative images illustrating GFAP promoter-driven NeuroD1-GFP fluorescence in 5xFAD mouse cortex in the left panel, NeuN immunofluorescence in the same field, shown in the middle panel, and the overlap of GFAP promoter-driven NeuroD1-GFP fluorescence and NeuN immunofluorescence in the same field, shown in the right panel, scale bar, 20 µm.

NeuroD1-converted neurons in the AD brain were innervated by glutamatergic (VGluT1 immunopositive) and GABAergic (GAD65 immunopositive) terminals. FIG. 3D shows representative images illustrating NeuroD1-GFP fluorescence in 5xFAD mouse cortex in the top panel and VGlut1 immunofluorescence, arrowhead, in the same field shown in the bottom panel, scale bar, 5 µm. FIG. 3E shows representative images illustrating GAD65 immunofluorescence, arrow, in 5xFAD mouse cortex in the same field as in FIG. 3D in the top panel and the overlap of NeuroD1-GFP fluorescence, VGlut1 immunofluorescence and GAD65 immunofluorescence in the same field, shown in the bottom panel, scale bar, 5 µm.

Cortical slice recording demonstrated that the NeuroD1-converted neurons in the AD brain were functional, with the peak amplitude of $I_{Na}$ at 2270±282 pA (n=5) and $I_K$ at 5498±706 pA (n=5). FIG. 3F shows representative traces of sodium and potassium currents of NeuroD1-converted neurons at 28 DPI with retrovirus construct encoding NeuroD1-GFP in AD cortical slices (5xFAD mouse cortex).

Spontaneous synaptic events in NeuroD1-converted neurons were recorded; frequency, 2.80±0.95 Hz; amplitude, 20.5±2.7 pA; n=7, suggesting that these newly converted neurons have been integrated into the neural circuits. FIG. 3G shows representative traces of spontaneous synaptic events recorded from NeuroD1-converted neurons at 28 DPI with retrovirus construct encoding NeuroD1-GFP in the AD cortical slices (5xFAD mouse cortex). All synaptic events were blocked by the mixture of AMPA/kainate receptor blocker CNQX (10 µM) and $GABA_A$ receptor blocker BIC (20 µM). FIG. 3H shows an enlarged view of two synaptic events shown in FIG. 3G.

Beneficial effects of the conversion of reactive glial cells to neurons by NeuroD1 on the AD brain were examined.

Figure 3I:
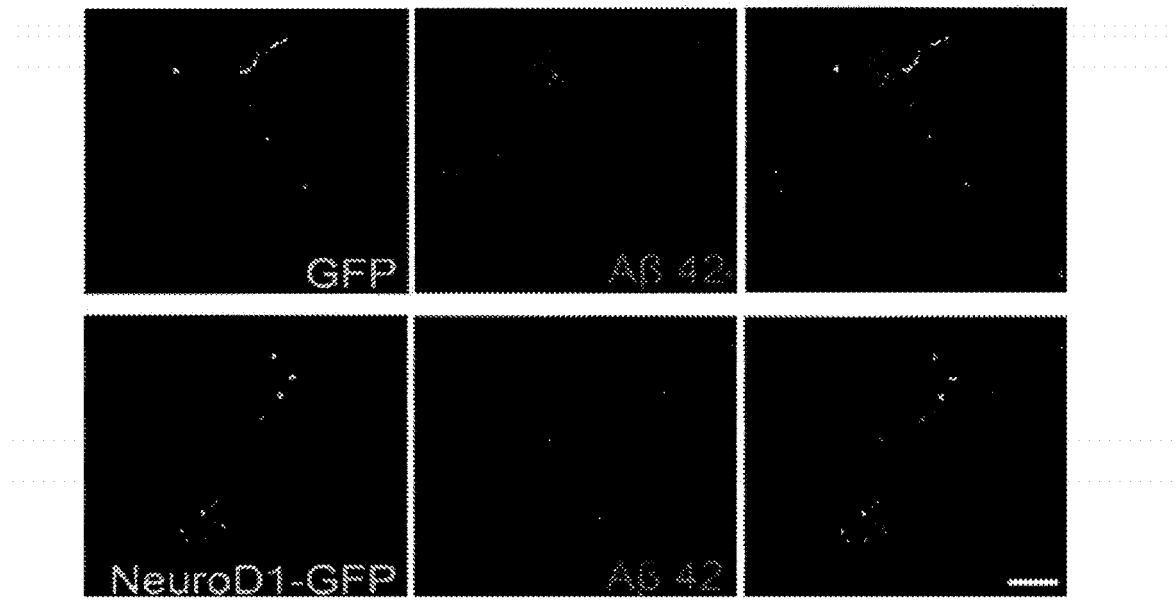
FIG. 3I shows representative images illustrating GFP fluorescence in cells infected with a retrovirus construct encoding GFP alone, top left or NeuroD1-GFP fluorescence in cells infected with a retrovirus construct encoding NeuroD1-GFP, bottom left, at 15-17 DPI.

Immunostaining with Aβ1-42 showed a significant decrease of Aβ deposit in NeuroD1-converted region compared to GFP control. Aβ deposit decreased in region of 5xFAD mouse cortex infected with a retrovirus construct pCAG-NeuroD1-IRES-GFP, n=8. FIG. 3I shows representative images illustrating GFP fluorescence in cells infected with a retrovirus construct encoding GFP alone, top left or NeuroD1-GFP fluorescence in cells infected with a retrovirus construct pCAG-NeuroD1-IRES-GFP, bottom left, at 15-17 DPI. Aβ42 immunofluorescence in the same fields is shown in the corresponding middle panels top and bottom. The overlap of GFP fluorescence or NeuroD1-GFP fluorescence and Aβ42 immunofluorescence in the same field is shown in the corresponding right panels, scale bar, 100 µm.

Figure 3J:
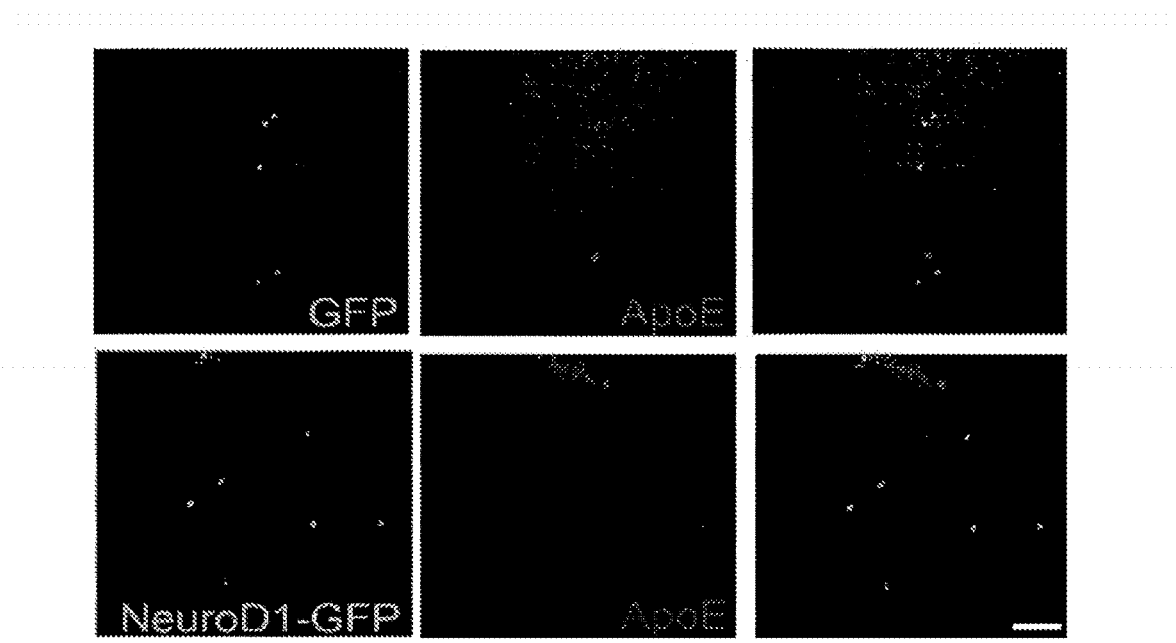
FIG. 3J shows representative images illustrating GFP fluorescence in cells infected with a retrovirus construct encoding GFP alone, top left or NeuroD1-GFP fluorescence in cells infected with a retrovirus construct encoding NeuroD1-GFP, bottom left, at 15-17 DPI.
Figure 3K:
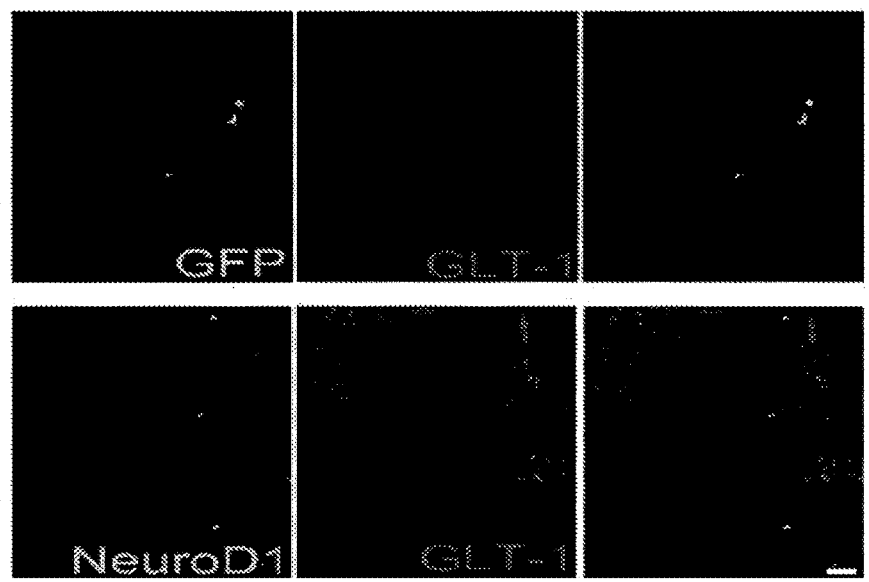
FIG. 3K shows representative images illustrating GFP fluorescence in cells infected with a retrovirus construct encoding GFP alone, top left or NeuroD1-GFP fluorescence in cells infected with a retrovirus construct encoding NeuroD1-GFP, bottom left, at 15-17 DPI.
Figures 3L, 3M, 3N:
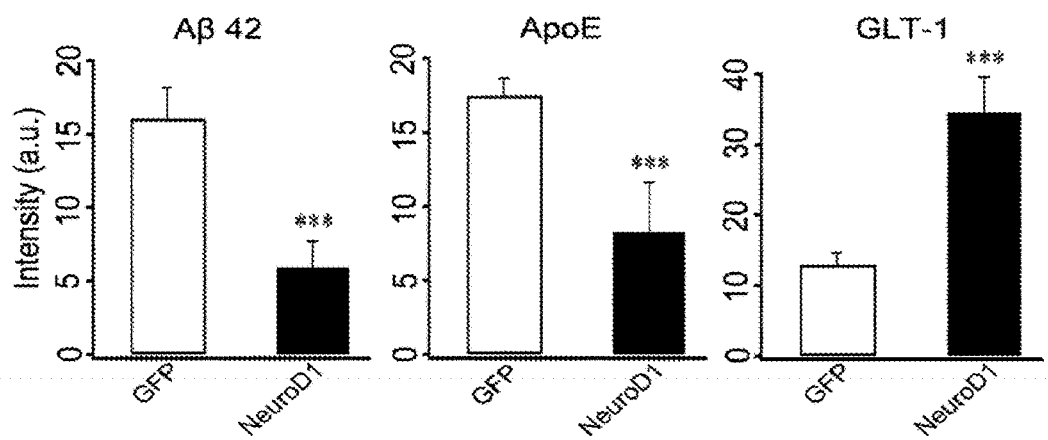
FIG. 3L is a graph showing results of quantitation of Aβ in the region of 5xFAD mouse cortex infected with retrovirus construct encoding NeuroD1-GFP at 15-17 DPI.
FIG. 3M is a graph showing results of quantitation of ApoE in the region of 5xFAD mouse cortex region infected with retrovirus construct encoding NeuroD1-GFP at 15-17 DPI.
FIG. 3N is a graph showing results of quantitation of Glt1 in the region of 5xFAD mouse cortex injured region infected with retrovirus construct encoding NeuroD1-GFP at 15-17 DPI.

The ApoE signal was also significantly decreased in the AD cortex after NeuroD1 infection, see FIG. 3J, quantified in FIG. 3M. ApoE signal decreased in region of 5xFAD mouse cortex infected with retrovirus construct pCAG-NeuroD1-IRES-GFP, n=8. FIG. 3J shows representative images illustrating GFP fluorescence in cells infected with a retrovirus construct encoding GFP alone, top left or NeuroD1-GFP fluorescence in cells infected with retrovirus construct pCAG-NeuroD1-IRES-GFP, bottom left, at 15-17 DPI. ApoE immunofluorescence in the same fields is shown in the corresponding middle panels top and bottom. The overlap of GFP fluorescence or NeuroD1-GFP fluorescence and ApoE immunofluorescence in the same field is shown in the corresponding right panels, scale bar, 100 µm.

Interestingly, the astrocytic glutamate transporter Glt1, which typically decreases after injury or disease, was significantly increased in the NeuroD1-converted region, see FIG. 3K, quantified in FIG. 3N. Astrocytic glutamate transporter Glt1 increased in region of 5xFAD mouse cortex infected with a retrovirus construct encoding NeuroD1-GFP, n=7. FIG. 3K shows representative images illustrating GFP fluorescence in cells infected with a retrovirus construct encoding GFP alone, top left or NeuroD1-GFP fluorescence in cells infected with a retrovirus construct encoding NeuroD1-GFP, bottom left, at 15-17 DPI. Glt1 immunofluorescence in the same fields is shown in the corresponding middle panels top and bottom. The overlap of GFP fluorescence or NeuroD1-GFP fluorescence and Glt1 immunofluorescence in the same field is shown in the corresponding right panels, scale bar, 40 µm.

FIG. 3L is a graph showing results of quantitation of Aβ in the region of 5xFAD mouse cortex infected with retrovirus construct pCAG-NeuroD1-IRES-GFP at 15-17 DPI, showing NeuroD1-induced conversion, compared to the control injured region infected with retrovirus construct encoding GFP alone, showing a significant decrease in Aβ in the injured region infected with retrovirus construct encoding NeuroD1-GFP, n=8.

FIG. 3M is a graph showing results of quantitation of ApoE in the region of 5xFAD mouse cortex region infected with retrovirus construct pCAG-NeuroD1-IRES-GFP at 15-17 DPI, showing NeuroD1-induced conversion, compared to the control injured region infected with retrovirus construct encoding GFP alone, showing a significant decrease in ApoE in the injured region infected with retrovirus construct encoding NeuroD1-GFP, n=8.

FIG. 3N is a graph showing results of quantitation of Glt1 in the region of 5xFAD mouse cortex injured region infected with retrovirus construct encoding NeuroD1-GFP at 15-17 DPI, showing NeuroD1-induced conversion, compared to the control injured region infected with retrovirus construct encoding GFP alone, showing a significant increase in Glt1 in the injured region infected with retrovirus construct encoding NeuroD1-GFP, n=7.

Example 17

Direct Conversion of Cultured Human Astrocytes into Functional Neurons

Figure 4A:
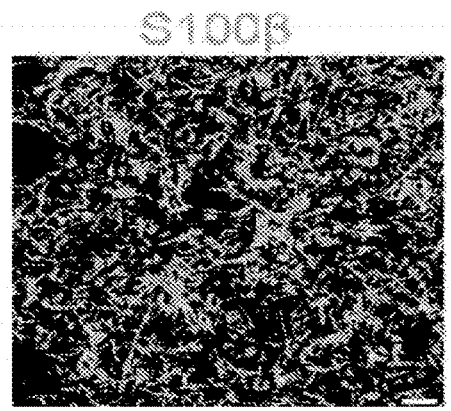
FIG. 4A is a representative immunofluorescence image showing that the majority of cultured human astrocytes were immunolabeled by S100β antibodies, scale bar, 50 μm.

Human cortical astrocytes (ScienCell, Calif.) in vitro culture were infected with retrovirus construct pCAG-NeuroD1-IRES-GFP. The cultured human astrocytes were mostly immunopositive for S100β, 94.3±0.7%, n=12, and rarely stained for NG2. FIG. 4A is a representative immunofluorescence image showing that the majority of cultured human astrocytes were immunolabeled by S100β antibodies, scale bar, 50 µm.

Figure 4G:
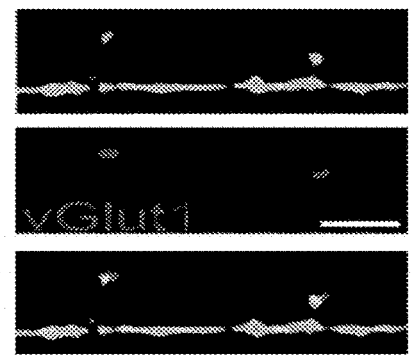
FIG. 4G is a high magnification image showing vesicular glutamate transporter 1 (VGlut1) immunostained puncta co-localized with dendritic spines on NeuroD1-converted neurons.
Figure 4B:
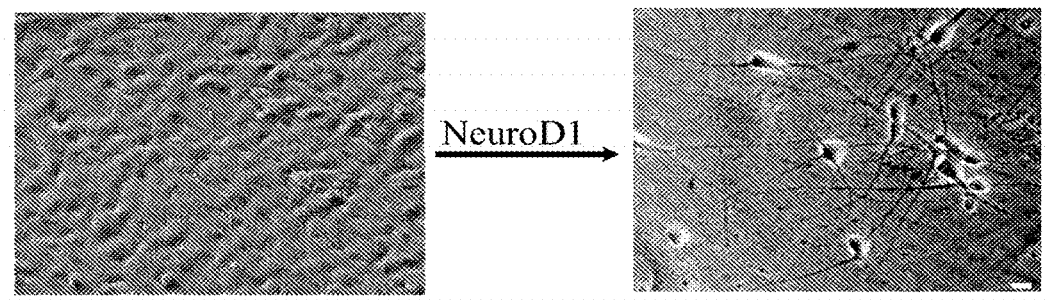
FIG. 4B is a representative pair of phase contrast images showing NeuroD1-induced morphological change from astrocytes (left) to neurons at 45 DPI with a retrovirus encoding NeuroD1 (right)

Infection by retrovirus construct pCAG-NeuroD1-IRES-GFP significantly changed the cell morphology from astrocytes to neurons. FIG. 4B is a representative pair of phase contrast images showing NeuroD1-induced morphological change from astrocytes (left) to neurons at 45 DPI with a retrovirus construct pCAG-NeuroD1-IRES-GFP (right), scale bar, 20 μm.

Figure 4C:
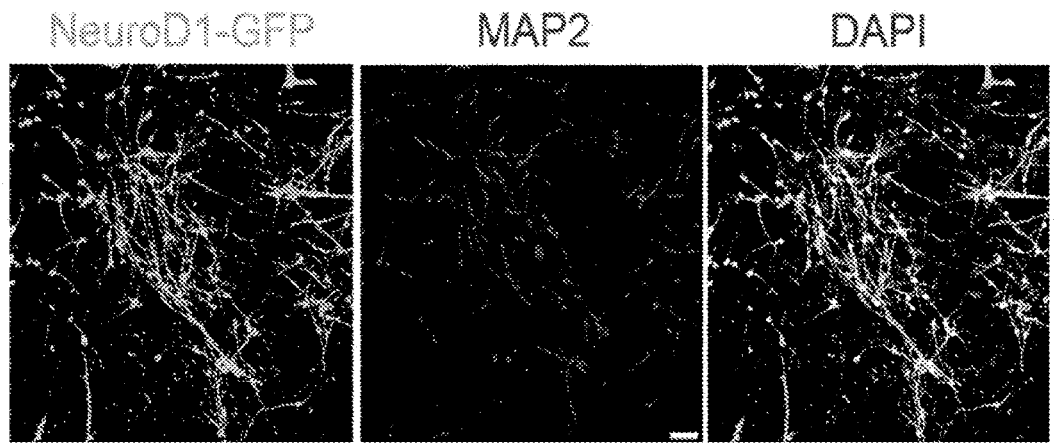
FIG. 4C shows representative images illustrating GFP fluorescence in human astrocytes infected with a retrovirus construct encoding NeuroD1-GFP.

After NeuroD1-infection, the majority of cells became immunopositive for a neuronal marker MAP2. FIG. 4C shows representative images illustrating GFP fluorescence in human astrocytes infected with retrovirus construct pCAG-NeuroD1-IRES-GFP, left, at 30 DPI, converted into MAP2-positive neurons, same field, middle and overlap of the left and middle images further showing DAPI fluorescence, scale bar, 50 μm.

Figure 4D:
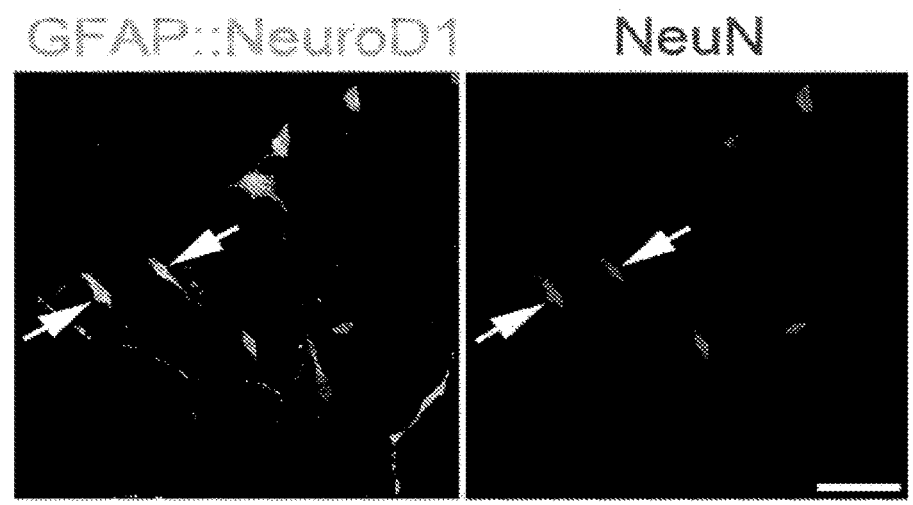
FIG. 4D shows representative images illustrating GFP fluorescence in human astrocytes infected with a retrovirus construct encoding GFAP promoter-driven NeuroD1-GFP.

Cultured human astrocytes were infected with a retrovirus encoding NeuroD1 under control of the human GFAP promoter, GFAP::NeuroD1-IRES-GFP, resulting in conversion of the majority of NeuroD1-infected cells to NeuN-positive neurons. FIG. 4D shows representative images illustrating GFP fluorescence in human astrocytes infected with a retrovirus construct encoding GFAP promoter-driven NeuroD1-GFP, left, at 12 DPI and showing that infected human astrocytes were also immunopositive for NeuN, same field, right, scale bar, 40 μm.

Quantitatively, among all human astrocytes infected with GFAP::NeuroD1-IRES-GFP (n=976 with 4 independent repeats), about 95.4±1% cells were converted into neurons (NeuN positive).

Figure 4E:
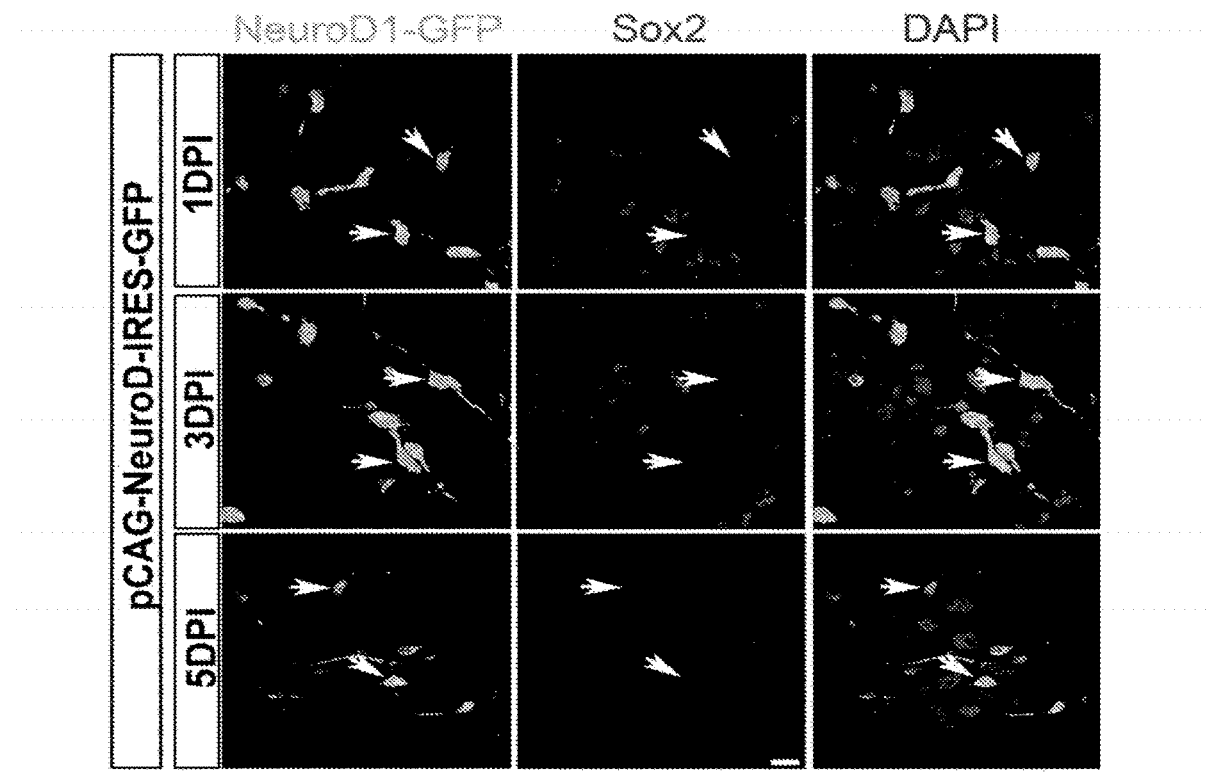
FIG. 4E shows representative images illustrating direct conversion of human astrocytes into neurons.

The trans-differentiation process of conversion of human astrocytes to neurons following expression of exogenous NeuroD1 was examined from 24 hours until 5 days after infection of the human astrocytes with a retrovirus encoding NeuroD1. No transient increase in the expression level of neural stem cell marker Sox2 or Musashi occurred during the early conversion period. FIG. 4E shows representative images illustrating direct conversion of human astrocytes into neurons by introduction of exogenous NeuroD1 into the astrocytes by expression of a retrovirus construct encoding NeuroD1, without transition through the Sox2-positive neuroprogenitor stage. After only 1-3 days of infection by NeuroD1, some astrocytes already became neuron-like cells with clearly extended neurites (FIG. 4E, arrows). Astrocytes usually had low level of Sox2 expression but astrocytes infected with GFAP::NeuroD1-IRES-GFP (arrows) were devoid of Sox2 signal. DAPI staining of the cell nucleus shows the total number of cells in the imaging field. Images at left show NeuroD1-GFP fluorescence, images in middle panels show Sox2 immunofluorescence and images at right show overlap of NeuroD1-GFP fluorescence, Sox2 immunofluorescence and DAPI fluorescence in the same field, scale bar, 20 μm.

Figure 18G:
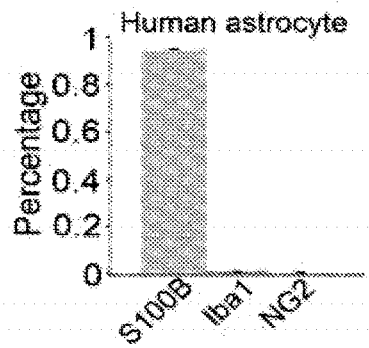
FIG. 18G is a graph showing quantitation of cultured human astrocytes immunopositive for S100β.
Figure 18H:
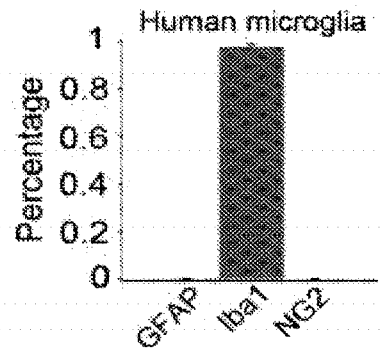
FIG. 18H is a graph showing quantitation of cultured human microglia immunopositive for GFAP, Iba1.

Human astrocytes converted into neurons by expression of exogenous NeuroD1 by infection with GFAP::NeuroD1-IRES-GFP were immunopositive for glutamate but not for GABA (FIG. 17). Cultured human microglia were infected with retrovirus encoding NeuroD1-GFP, but no DCX-positive neurons were detected (FIGS. 18D-18F). Therefore, human astrocytes, but not microglia, can be directly converted into neurons by induced NeuroD1 expression.

Figure 4F:
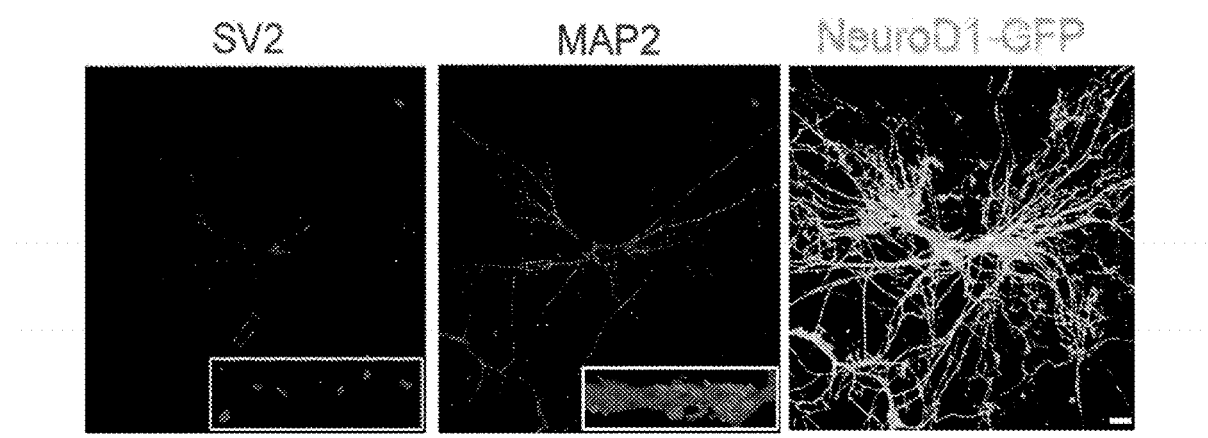
FIG. 4F shows representative images of immunostained synaptic puncta (SV2, left) on the dendrites (MAP2, middle) of NeuroD1-converted human neurons at 45 DPI, NeuroD1-GFP fluorescence.

Immunostaining with synaptic marker SV2 and glutamatergic synapse marker VGluT1 was performed to determine whether NeuroD1-converted human neurons are functionally connected. Numerous SV2 puncta were observed on MAP2-labeled neuronal dendrites following infection of astrocytes with retrovirus encoding NeuroD1. FIG. 4F shows representative images of immunostained synaptic puncta (SV2, left) on the dendrites (MAP2, middle) of NeuroD1-converted human neurons at 45 DPI, NeuroD1-GFP fluorescence, right, scale bar, 20 μm.

Some neurons showed mushroom-like mature spines, which were co-localized with VGluT1 puncta. FIG. 4G is a high magnification image showing vesicular glutamate transporter 1 (VGlut1) immunostained puncta co-localized with dendritic spines on NeuroD1-converted neurons, scale bar, 10 μm.

Figure 4H:
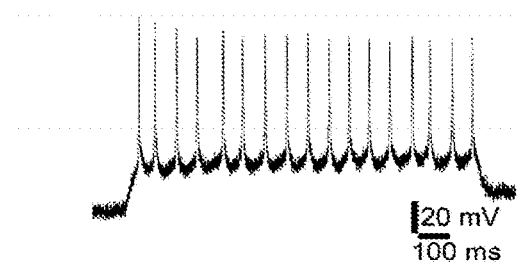
FIG. 4H is a representative trace of repetitive action potentials in NeuroD1-converted neurons at 20 DPI.
Figure 4I:
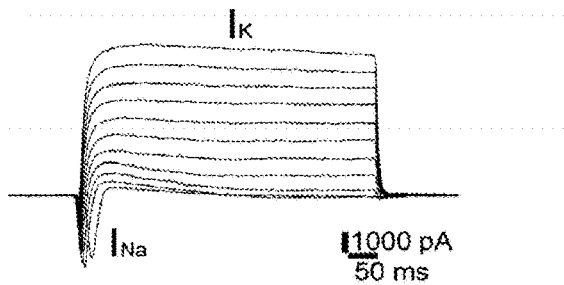
FIG. 4I shows a representative trace showing the Na$^+$ and K$^+$ currents recorded from NeuroD1-converted neurons at 30 DPI.

Patch clamp recordings were used to test the function of human astrocytes converted to human neurons. After 20 DPI, repetitive action potential firing, n=15, and large sodium ($I_{Na}$) and potassium currents ($I_K$), n=12, were recorded. FIG. 4H is a representative trace of repetitive action potentials in NeuroD1-converted neurons at 20 DPI. FIG. 4I shows a representative trace showing the $Na^+$ and $K^+$ currents recorded from NeuroD1-converted neurons at 30 DPI.

Figure 4J:
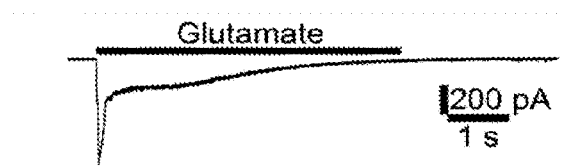
FIG. 4J shows a representative trace showing receptor currents induced by bath application of 100 μM glutamate.
Figure 4K:
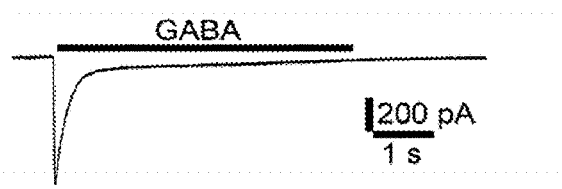
FIG. 4K shows a representative trace showing receptor currents induced by bath application of 100 μM GABA.
Figure 4L:
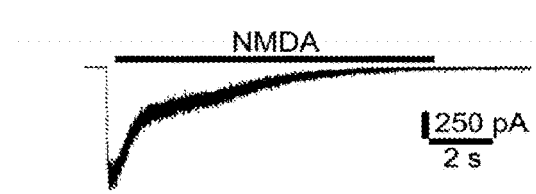
FIG. 4L shows a representative trace showing receptor currents induced by bath application of 100 μM NMDA.

Large glutamate receptor currents (31-35 DPI, 548±138 pA, n=7), $GABA_A$ receptor currents (31-35 DPI, 599±114 pA, n=8), and NMDA-evoked currents (40 DPI, 966±101 pA, n=8) were also detected. FIG. 4J shows a representative trace showing receptor currents induced by bath application of 100 μM glutamate. FIG. 4K shows a representative trace showing receptor currents induced by bath application of 100 μM GABA. FIG. 4L shows a representative trace showing receptor currents induced by bath application of 100 μM NMDA.

Figure 4M:
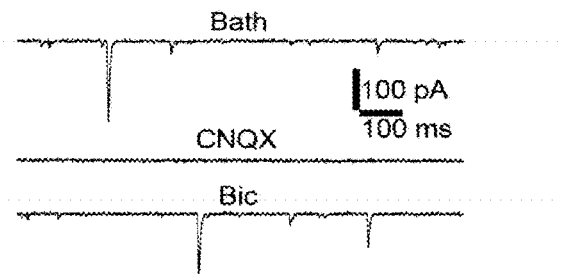
FIG. 4M shows representative traces of spontaneous synaptic events in NeuroD1-converted neurons at 40 DPI.

Furthermore, functional synaptic events in NeuroD1-converted neurons (frequency, 1.6±0.3 Hz; and amplitude, 23.2±0.8 pA; n=13), which were completely blocked by AMPA/kainate receptor antagonist CNQX (10 μM) but not by $GABA_A$ receptor antagonist bicuculline (20 μM) were detected. FIG. 4M shows representative traces of spontaneous synaptic events in NeuroD1-converted neurons at 40 DPI. Note that all synaptic events were blocked by CNQX (10 μM) but not by Bic (20 μM), suggesting that the human astrocytes converted to human neurons by expression of exogenous NeuroD1 were glutamatergic.

Example 18

Cells Infected with a Retrovirus Encoding NeuroD1 are Doublecortin (DCX)-Positive Neurons.

FIG. 5A is a set of low power images showing reactive glial cells infected with a retrovirus encoding only GFP in the vicinity of injury core shown at *, 14 DPI. GFP fluorescence is shown at left, along with GFAP immunostaining of the same field, middle and overlap of GFP fluorescence, GFAP immunostaining and DAPI fluorescence of the same field, right, scale bar, 40 μm.

At 4 DPI, cells infected with a retrovirus encoding NeuroD1 and GFP were mostly positive for DCX, an immature neuronal marker. In FIG. 5B, NeuroD1-GFP fluorescence is shown at left, along with DCX immunostaining of the same field, middle and overlap of GFP fluorescence and DCX immunostaining of the same field, right, scale bar, 40 μm. Note a significant number of DCX-positive neurons after NeuroD1 infection.

FIG. 5C are low power images showing DCX-positive cells infected with a retrovirus encoding NeuroD1 and GFP along the injection site at 14 DPI. NeuroD1-GFP fluorescence is shown at left, along with DCX immunostaining of the same field, middle and overlap of NeuroD1-GFP fluorescence, DCX immunostaining and DAPI fluorescence in the same field, right, scale bar, 100 μm. Note that the injury site was in the cortical areas above the hippocampus delineated by DAPI staining. FIG. 5D are high power images showing DCX-positive cells infected with a retrovirus encoding NeuroD1 and GFP along the injection site at 14 DPI. NeuroD1-GFP fluorescence is shown at left, along with DCX immunostaining of the same field, middle and overlap of NeuroD1-GFP fluorescence, DCX immunostaining and DAPI fluorescence in the same field, right. Note that the injury site was in the cortical areas above the hippocampus delineated by DAPI staining, scale bar, 20 μm.

Figure 5E:
FIG. 5E shows images illustrating that GFAP::GFP retrovirus-infected astrocytes were DCX-negative.

FIG. 5E show images illustrating that GFAP::GFP retrovirus-infected astrocytes were DCX-negative, scale bar, 40 μm.

Example 19

NeuroD1 Converts Cultured Mouse Astrocytes into Neurons

Figure 6A:
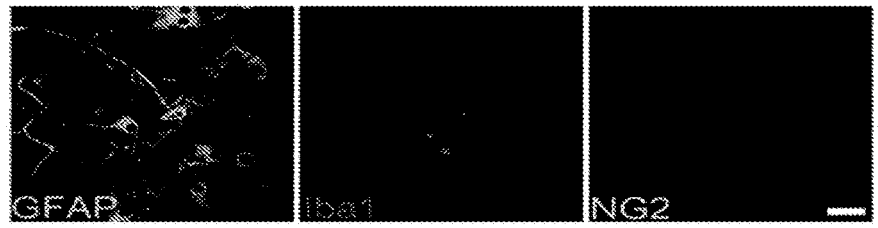
FIG. 6A shows representative images illustrating that cultured mouse astrocytes were mostly immunopositive for astrocyte marker GFAP.

A retrovirus encoding NeuroD1 was used to infect cultured mouse astrocytes and NG2 cells. NeuroD1 efficiently converted cultured mouse astrocytes into neurons. FIG. 6A shows representative images illustrating that cultured mouse astrocytes were mostly immunopositive for astrocyte marker GFAP (left, 87.8±1.4%), with a few positive for Iba1 (middle) but rarely NG2 (right).

Figure 6B:
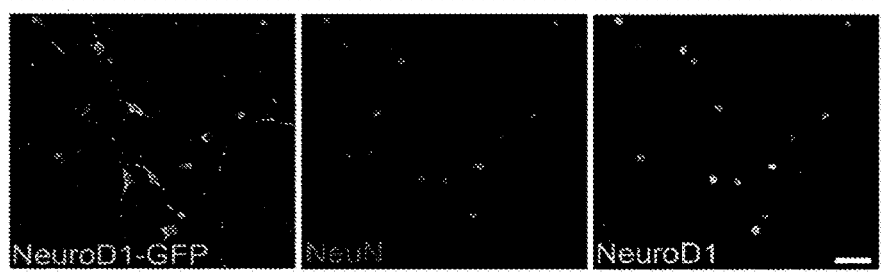
FIG. 6B shows representative images illustrating that NeuroD1-GFP retrovirus infected cells were immunopositive for NeuN; NeuroD1-GFP fluorescence is shown at left, NeuN immunostaining of the same field is shown in the middle panel and NeuroD1 immunostaining of the same field is shown in the panel at right.

FIG. 6B shows representative images illustrating that NeuroD1-GFP retrovirus infected cells were immunopositive for NeuN. NeuroD1 expression was confirmed by NeuroD1 staining (8 DPI). In FIG. 6B NeuroD1-GFP fluorescence is shown at left, NeuN immunostaining of the same field is shown in the middle panel and NeuroD1 immunostaining of the same field is shown in the panel at right, scale bar, 40 μm.

Figure 6C:
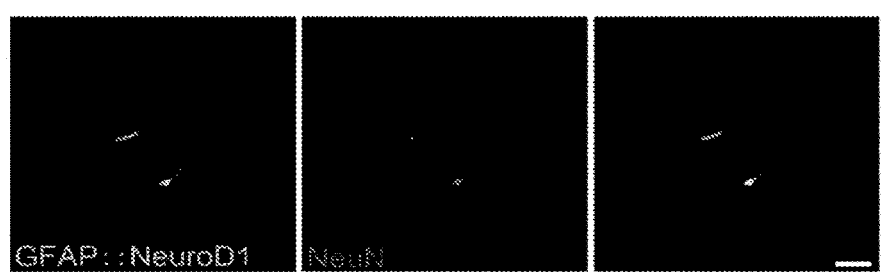
FIG. 6C shows representative images illustrating that GFAP::NeuroD1 retrovirus-infected cells were also positive for NeuN (8 DPI); NeuroD1-GFP fluorescence is shown at left, NeuN immunostaining of the same field is shown in the middle panel and overlap of the NeuroD1-GFP fluorescence and NeuN immunostaining of the same field is shown in the panel at right.

FIG. 6C shows representative images illustrating that GFAP::NeuroD1 retrovirus-infected cells were also positive for NeuN (8 DPI). In FIG. 6C NeuroD1-GFP fluorescence is shown at left, NeuN immunostaining of the same field is shown in the middle panel and overlap of the NeuroD1-GFP fluorescence and NeuN immunostaining of the same field is shown in the panel at right, scale bar, 40 μm.

Figure 6D:
FIG. 6D shows representative images illustrating that NeuroD1-GFP infected cells were mostly positive for cortical neuron marker Tbr1; NeuroD1-GFP fluorescence is shown at left, Tbr1 immunostaining of the same field is shown in the middle panel and overlap of the NeuroD1-GFP fluorescence and Tbr1 immunostaining of the same field is shown in the panel at right.

FIG. 6D shows representative images illustrating that cells infected with a retrovirus construct encoding NeuroD1 were mostly positive for cortical neuron marker Tbr1. In FIG. 6D NeuroD1-GFP fluorescence is shown at left, Tbr1 immunostaining of the same field is shown in the middle panel and overlap of the NeuroD1-GFP fluorescence and Tbr1 immunostaining of the same field is shown in the panel at right, scale bar, 40 μm.

Figure 6E:
FIG. 6E shows representative images illustrating that some NeuroD1-infected cells were also positive for dentate granule cell marker Prox1; NeuroD1-GFP fluorescence is shown at left, Prox1 immunostaining of the same field is shown in the middle panel and overlap of the NeuroD1-GFP fluorescence and Prox1 immunostaining of the same field is shown in the panel at right.
Figure 6F:
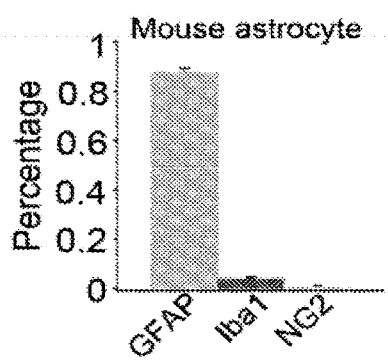
FIG. 6F is a graph showing quantitation of cultured mouse astrocytes immunopositive for GFAP, Iba1 and NG2.

FIG. 6E shows representative images illustrating that some cells infected with a retrovirus construct encoding NeuroD1 were also positive for dentate granule cell marker Prox1 (8 DPI). In FIG. 6E NeuroD1-GFP fluorescence is shown at left, Prox1 immunostaining of the same field is shown in the middle panel and overlap of the NeuroD1-GFP fluorescence and Prox1 immunostaining of the same field is shown in the panel at right, scale bar, 40 μm. FIG. 6F is a graph showing quantitation of cultured mouse astrocytes immunopositive for GFAP, Iba1 and NG2.

Example 20

Functional Characterization of NeuroD1-Converted Neurons Generated by Infection of Mouse Astrocytes with a Retrovirus Encoding NeuroD1

NeuroD1-converted neurons generated by infection of mouse astrocytes with a retrovirus encoding NeuroD1 showed large GABA, glutamate and NMDA currents, as well as spontaneous synaptic events which were blocked by CNQX but not BIC, suggesting that they were glutamatergic neurons. FIG. 7A shows large receptor currents induced by bath application of GABA (100 μM) in mouse astrocyte-converted neurons, 7 DPI: 405±97 pA; 14 DPI: 861±55 pA; n=8.

FIG. 7B shows glutamate (100 μM) evoked currents (7 DPI: 517±145 pA; 14 DPI: 1061±159 pA; n=8). FIG. 7C shows NMDA (100 μM) evoked currents (7 DPI: 676±118 pA; 14 DPI: 1315±95; n=9). FIG. 7D shows spontaneous synaptic currents recorded from NeuroD1-converted neurons (14 DPI; frequency, 1.15±0.24 Hz, amplitude, 21.5±0.7 pA, n=13). Note that synaptic events were blocked by CNQX (10 μM), glutamate receptor blocker, but not by $GABA_A$ receptor blocker bicuculline (Bic, 20 μM), suggesting that astrocyte-converted neurons by NeuroD1 were glutamatergic.

Example 21

NeuroD1 Converts NG2 Cells into Neurons

Figure 8G:
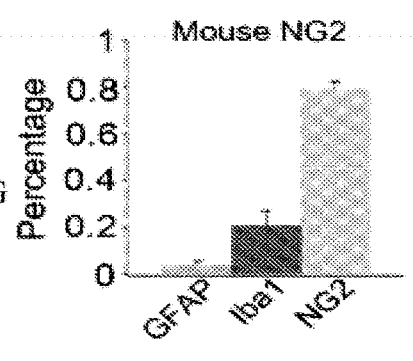
FIG. 8G is a graph showing quantitation of cultured mouse NG2 cells immunopositive for GFAP, Iba1 and NG2.
Figure 8A:
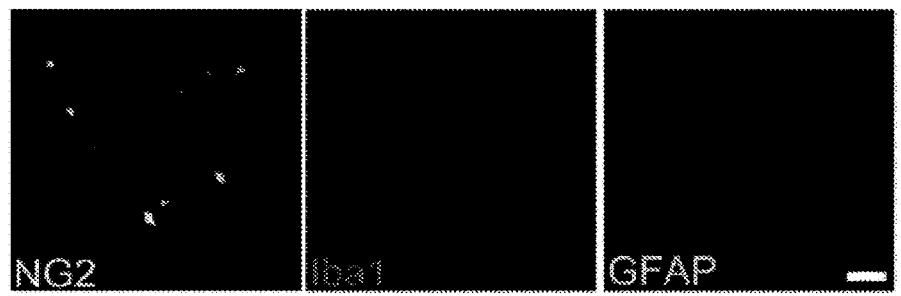
FIG. 8A shows representative images of cultured mouse NG2 cells showing NG2 immunostaining, left, Iba1 immunostaining, middle, and GFAP immunostaining, right.
Figure 8B:
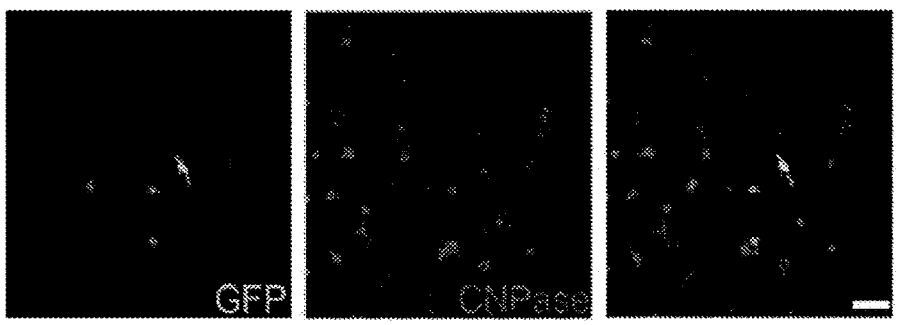
FIG. 8B shows GFP fluorescence at left, CNPase immunostaining at middle panel and the overlap of GFP fluorescence and CNPase immunostaining of the same field at right panel.
Figure 8C:
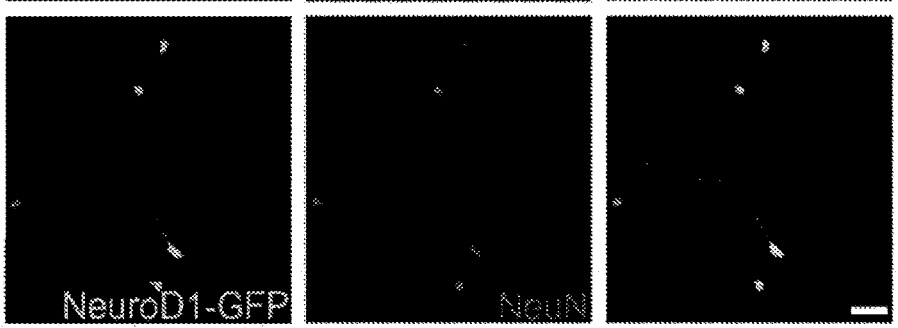
FIG. 8C shows representative images illustrating that NG2 cells infected with a retrovirus encoding NeuroD1-GFP became NeuN-positive neurons; NeuroD1-GFP fluorescence is shown at left, NeuN immunostaining is shown at the middle panel and the overlap of GFP fluorescence and NeuN immunostaining of the same field is shown at right panel.
Figure 8D:
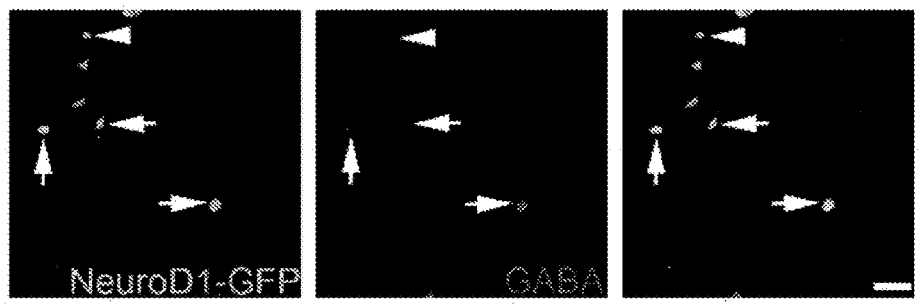
FIG. 8D shows representative images illustrating that many NeuroD1-infected NG2 cells became GABAergic neurons.
Figure 8E:
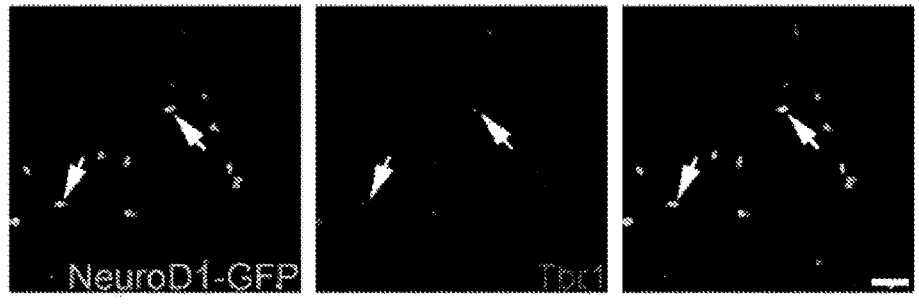
FIG. 8E shows representative images illustrating that NeuroD1-infected NG2 cells were mostly immunopositive for cortical neuron marker Tbr1.
Figure 8F:
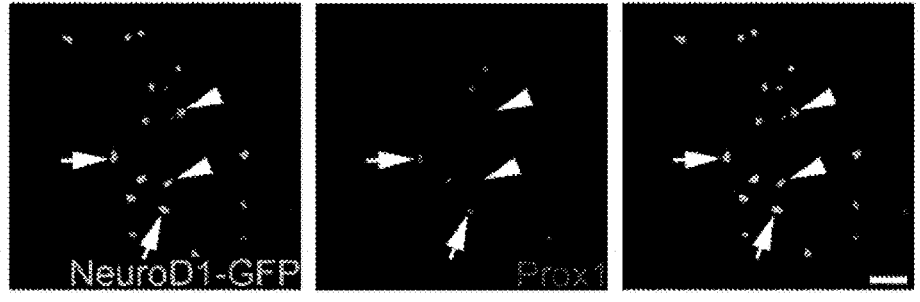
FIG. 8F shows representative images illustrating that NeuroD1-infected NG2 cells were either positive (arrow) or negative for Prox1 (arrowhead)

NeuroD1 also converted NG2 cells into NeuN-positive neurons, confirming the in vivo observation described herein. However, different from astrocyte conversion, many NG2-converted neurons were immunopositive for GABA. FIG. 8A shows representative images of cultured mouse NG2 cells showing NG2 immunostaining, left, Iba1 immunostaining, middle, and GFAP immunostaining, right, indicating that the majority of cells in the mouse NG2 cultures were immunopositive for NG2 (79.2±3.2%), scale bar, 40 μm. Cultured mouse NG2 cells had many oligodendrocytes as identified immunopositive for CNPase at 5 DPI with a retrovirus construct encoding GFP without NeuroD1. In FIG. 8B GFP fluorescence is shown at left, CNPase immunostaining is shown in the middle panel and the overlap of GFP fluorescence and CNPase immunostaining of the same field is shown in the right panel, scale bar, 40 μm. NG2 cells are oligodendrocyte precursor cells. FIG. 8C shows representative images illustrating that NG2 cells infected with a retrovirus encoding NeuroD1-GFP became NeuN-positive neurons, shown at 5 DPI. In FIG. 8C NeuroD1-GFP fluorescence is shown at left, NeuN immunostaining is shown in the middle panel and the overlap of GFP fluorescence and NeuN immunostaining of the same field is shown in the right panel, scale bar, 40 μm. FIG. 8D shows representative images illustrating that, different from astrocytes, many NG2 cells infected with a retrovirus construct encoding NeuroD1 became GABAergic neurons, 7 DPI; 72.7±9.2%, n=7. In FIG. 8D NeuroD1-GFP fluorescence is shown at left, GABA immunostaining is shown in the middle panel and the overlap of GFP fluorescence and GABA immunostaining of the same field is shown in the right panel, scale bar, 40 μm. Arrows in FIG. 8D point to GABAergic neurons, arrowhead points to a non-GABAergic neuron. FIG. 8E shows representative images illustrating that NG2 cells infected with a retrovirus construct encoding NeuroD1 were mostly immunopositive for cortical neuron marker Tbr1, 5 DPI. In FIG. 8E NeuroD1-GFP fluorescence is shown at left, Tbr1 immunostaining is shown in the middle panel and the overlap of GFP fluorescence and Tbr1 immunostaining of the same field is shown in the right panel, scale bar, 40 μm. FIG. 8F shows representative images illustrating that NG2 cells infected with a retrovirus construct encoding NeuroD1 were either positive (arrow) or negative for Prox1 (arrowhead, 5 DPI). In FIG. 8F NeuroD1-GFP fluorescence is shown at left. Prox1 immunostaining is shown in the middle panel and the overlap of GFP fluorescence and Prox1 immunostaining of the same field is shown in the right panel, scale bar, 40

μm. FIG. 8G is a graph showing quantitation of cultured mouse NG2 cells immunopositive for GFAP, Iba1 and NG2.

Example 22

Functional Characterization of NG2 Cells Converted to Neurons by NeuroD1

Figure 9A:
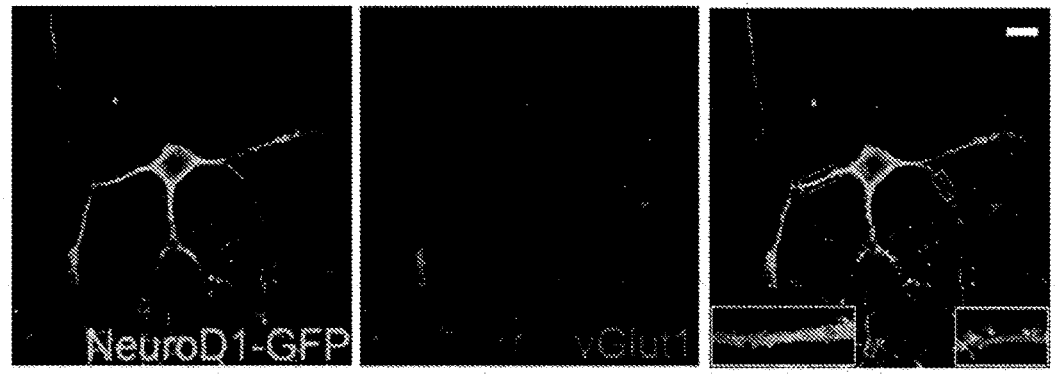
FIG. 9A shows representative images illustrating that numerous VGluT1 puncta were detected on NG2 cells converted to neurons by NeuroD1 after infecting mouse NG2 cultures with NeuroD1-GFP retrovirus.
Figure 9B:
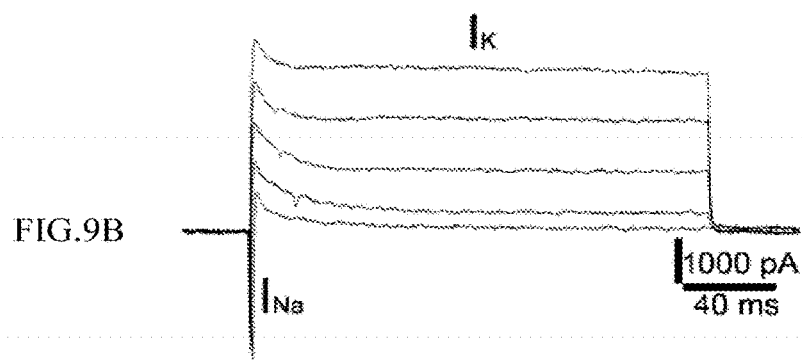
FIG. 9B is a representative trace showing that NG2 cells converted to neurons by NeuroD1 showed large sodium and potassium currents.
Figure 9C:
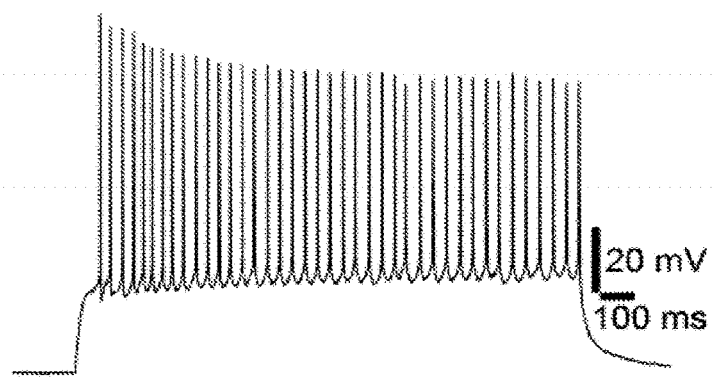
FIG. 9C is a representative trace showing that NG2 cells converted to neurons by NeuroD1 showed repetitive action potentials.
Figure 9D:
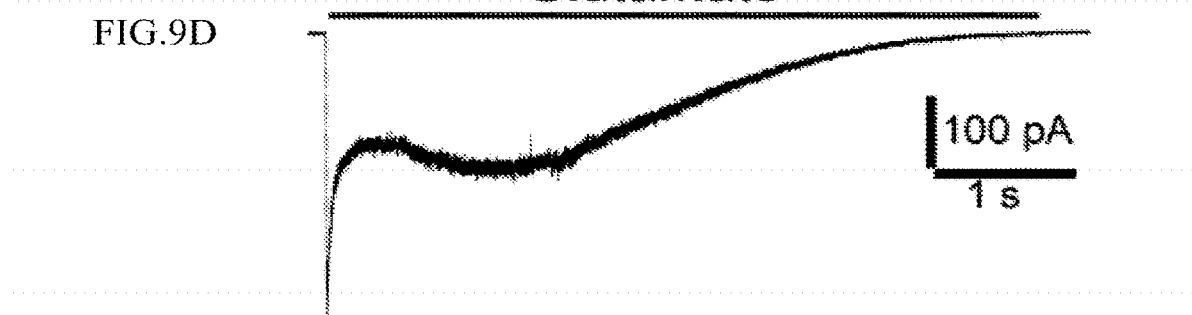
FIG. 9D is a representative trace showing that NG2 cells converted to neurons by NeuroD1 showed large glutamate-evoked current.
Figure 9E:
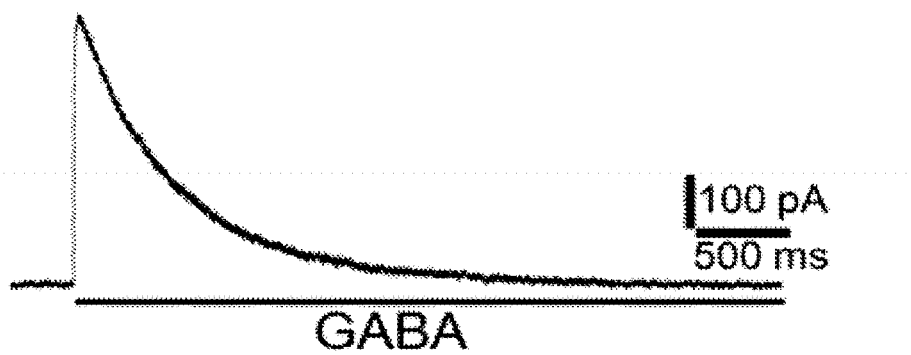
FIG. 9E is a representative trace showing that NG2 cells converted to neurons by NeuroD1 showed large GABA-evoked current.
Figure 9F:
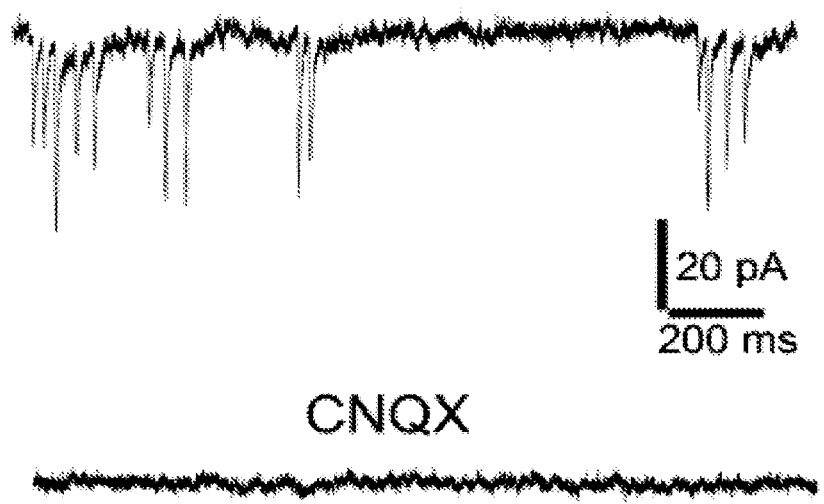
FIG. 9F is a representative trace showing that spontaneous synaptic events recorded from NG2 cells converted to neurons by NeuroD1 showed glutamatergic components.
Figure 9G:
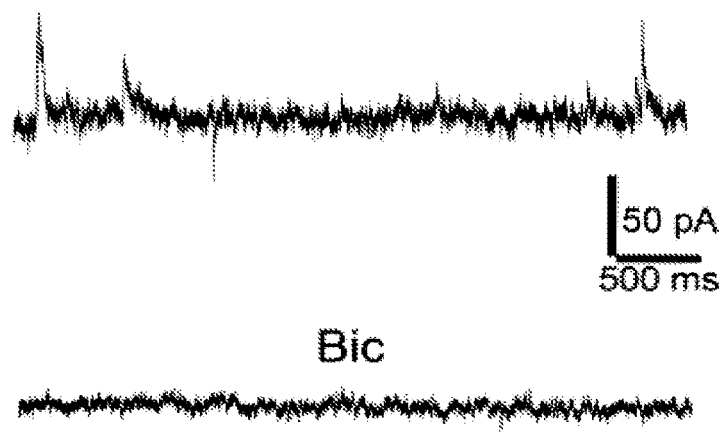
FIG. 9G is a representative trace showing that spontaneous synaptic events recorded from NG2 cells converted to neurons by NeuroD1 showed GABAergic components.

Patch-clamp recordings also revealed both glutamatergic and GABAergic events in NeuroD1-converted neurons generated by infection of NG2 cells with a retrovirus encoding NeuroD1. FIG. 9A shows representative images illustrating that numerous VGluT1 puncta were detected on NG2 cells converted to neurons by NeuroD1 after infecting mouse NG2 cultures with NeuroD1-GFP retrovirus. In FIG. 9A, NeuroD1-GFP fluorescence is shown in the left panel, vGlut1 immunostaining is shown in the middle panel and the overlap of NeuroD1-GFP fluorescence and vGlut1 immunostaining in the same field is shown in the right panel, scale bar, 20 μm. FIG. 9B is a representative trace showing that NG2 cells converted to neurons by NeuroD1 showed large sodium and potassium currents (n=10). FIG. 9C is a representative trace showing that NG2 cells converted to neurons by NeuroD1 showed repetitive action potentials (n=9). FIG. 9D is a representative trace showing that NG2 cells converted to neurons by NeuroD1 showed large glutamate-evoked current (n=7). FIG. 9E is a representative trace showing that NG2 cells converted to neurons by NeuroD1 showed large GABA-evoked current (n=9). Spontaneous synaptic events recorded from NG2 cells converted to neurons by NeuroD1 showed both glutamatergic and GABAergic components, confirming that NeuroD1 can convert NG2 cells into both excitatory and inhibitory neurons. FIG. 9F is a representative trace showing that spontaneous synaptic events recorded from NG2 cells converted to neurons by NeuroD1 showed glutamatergic components (n=8). FIG. 9G is a representative trace showing that spontaneous synaptic events recorded from NG2 cells converted to neurons by NeuroD1 showed GABAergic components (n=7).

Example 23

Long Survival of NeuroD1-Converted Neurons in Mouse Brain In Vivo

Figure 10A:
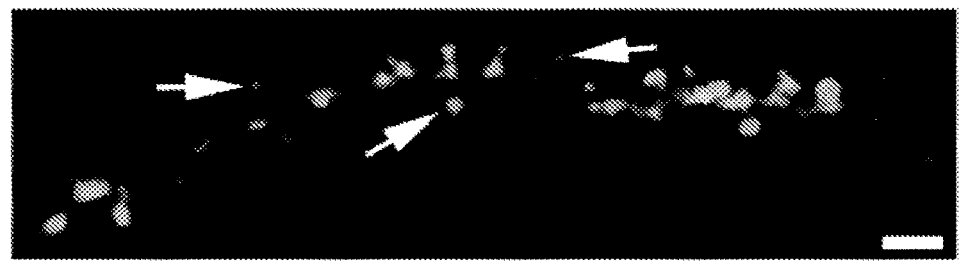
FIG. 10A is an image of NeuroD1-GFP fluorescence in clear dendritic spines (arrows) observed in 2-month old NeuroD1-converted neurons after viral injection.
Figure 10B:
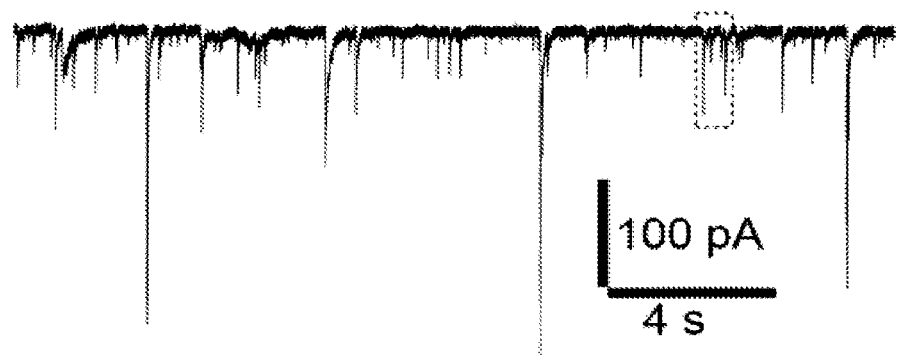
FIG. 10B is a representative trace showing large spontaneous synaptic events recorded from 2-month old NeuroD1-converted neurons in cortical slice recordings.
Figure 10C:
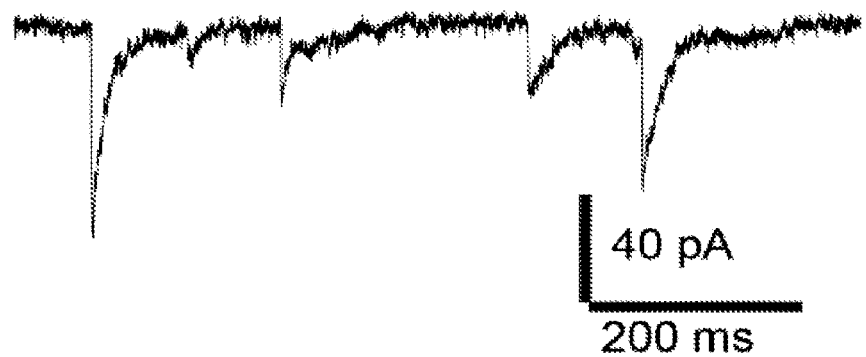
FIG. 10C is a representative trace showing an expanded view of the synaptic events shown in FIG. 10B.

It was found that NeuroD1-converted neurons can survive very long in the mouse brain, at least 2 months after retroviral injection, and these converted neurons showed many dendritic spines and large spontaneous synaptic events, n=3 animals. FIG. 10A is an image of NeuroD1-GFP fluorescence in clear dendritic spines (arrows) observed in 2-month old NeuroD1-converted neurons after viral injection, scale bar, 4 μm. FIG. 10B is a representative trace showing large spontaneous synaptic events recorded from 2-month old NeuroD1-converted neurons in cortical slice recordings. FIG. 10C is a representative trace showing an expanded view of the synaptic events shown in FIG. 10B.

Example 24

Lack of Endogenous Newborn Neurons in Mouse Cortex after Stab Injury

Figure 11A:
FIG. 11A shows representative images of BrdU immunostaining at 4 days post-injury, left panel, along with DCX immunostaining of the same field, middle panel, and the overlap of BrdU immunostaining and DCX immunostaining of the same field, right panel.
Figure 11B:
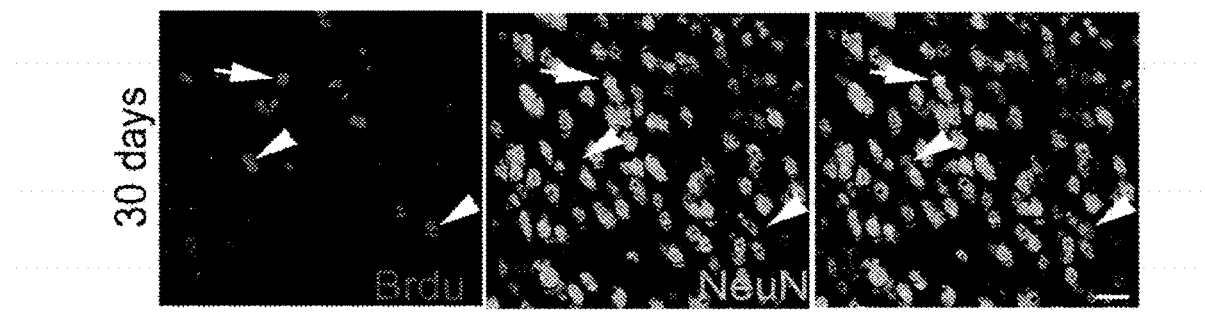
FIG. 11B shows representative images of BrdU immunostaining at 1 month post-injury, left panel, along with NeuN immunostaining of the same field, middle panel, and the overlap of BrdU immunostaining and NeuN immunostaining of the same field, right panel.

The number of NeuroD1-converted neurons in the injury areas was far more than the few newborn neurons found in the injury site without NeuroD1 infection. Immunostaining of BrdU was performed at 4 days and 1 month post injury. FIG. 11A shows representative images of BrdU immunostaining at 4 days post-injury, left panel, along with DCX immunostaining of the same field, middle panel, and the overlap of BrdU immunostaining and DCX immunostaining of the same field, right panel, scale bar, 20 μM. FIG. 11B shows representative images of BrdU immunostaining at 1 month post-injury, left panel, along with NeuN immunostaining of the same field, middle panel, and the overlap of BrdU immunostaining and NeuN immunostaining of the same field, right panel, scale bar, 20 μM. The majority of BrdU-positive cells were not neurons (arrowhead), with only a few exceptions (arrow). n=3 animals. Quantitatively, BrdU-labeled endogenous NeuN-positive neurons induced by stab injury were only 26±4 per mm$^2$ (n=3 animals), whereas our NeuroD1-GFP infected NeuN-positive neurons after stab injury were 294±22 per mm$^2$ (n=6 animals). These results demonstrate that NeuroD1 can convert a significant number of reactive glial cells, including both reactive astrocytes and NG2 cells, into functional neurons in vivo after brain injury. BrdU (100 mg/kg) was administered daily from 2-4 days post injury to label the injury-activated proliferative cells.

Example 25

Figure 12A:
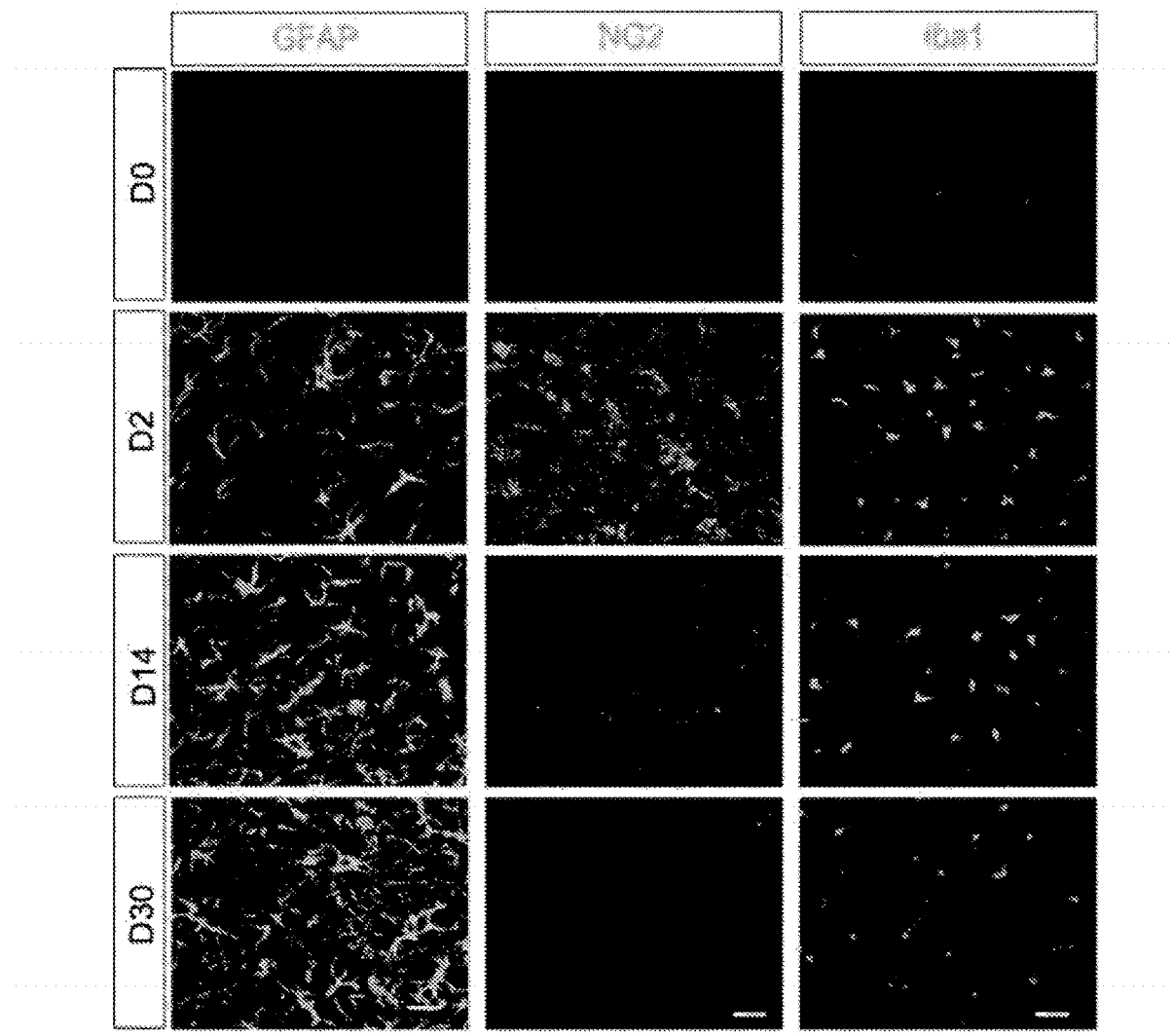
FIG. 12A shows representative images of immunostaining showing changes of GFAP (astrocyte), NG2 (NG2 cell), and Iba1 (microglia) signal before (D0) and up to one month after brain stab injury.
Figure 12B:
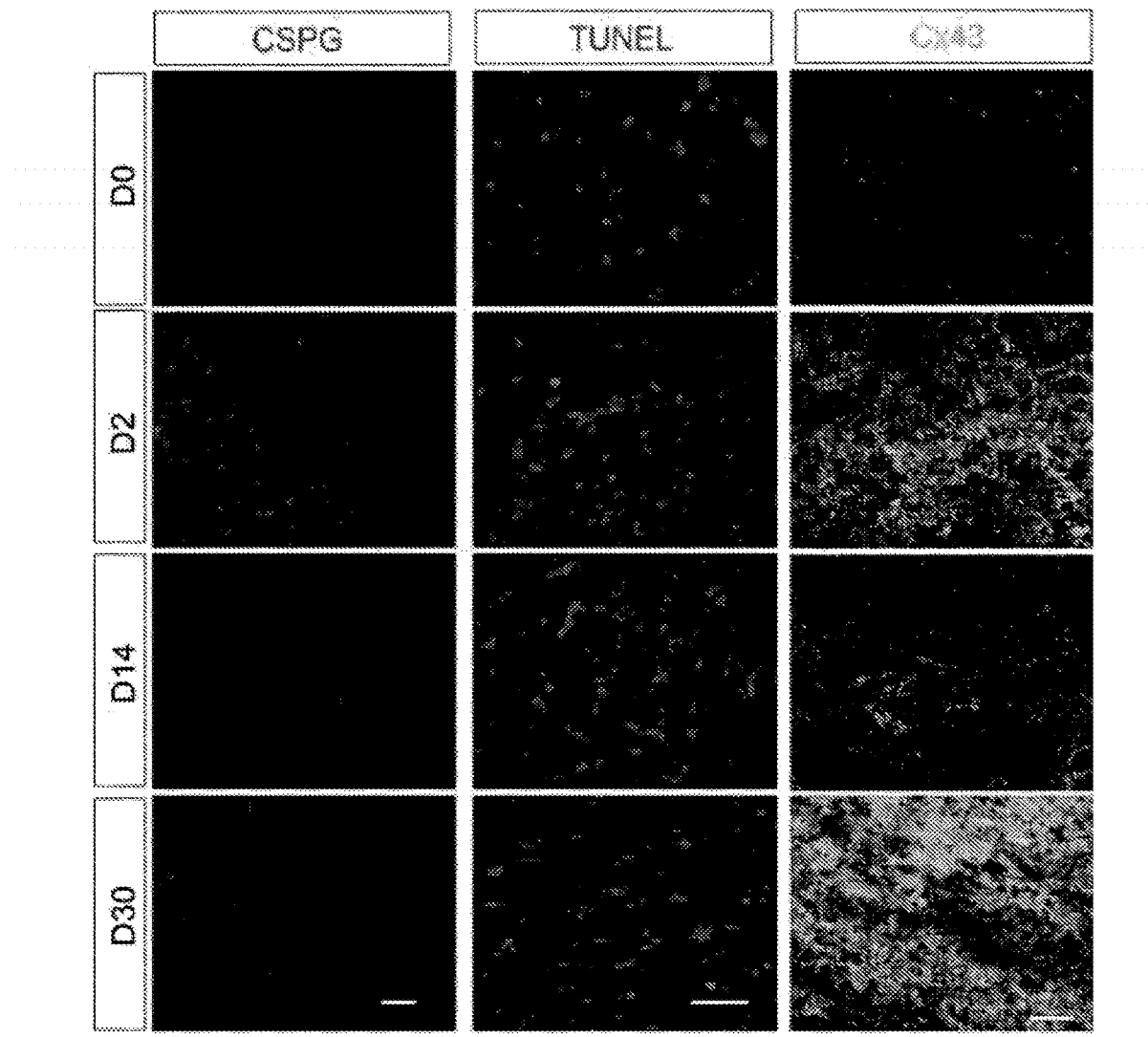
FIG. 12B shows representative images of TUNEL staining.

The Time Course of Glial Cell Response and the Detrimental Changes Induced by Brain Stab Injury The benefits of NeuroD1-converted neurons at the injury site were examined. After brain injury, neuroinhibitory proteoglycans typically increase whereas axon fibers and blood vessels usually decrease in the injury areas. A number of biomarkers were assayed after brain injury and followed their time course of changes from 2 days to one month after injury. It was found that 2 days after stab injury, the immunostaining signal of GFAP (reactive astrocytes), NG2 (NG2 cells), and Iba1 (microglia) all increased significantly. Interestingly, the GFAP and Iba1 signal remained very high in 30 days after injury, whereas the NG2 signal decreased significantly after two weeks of injury. FIG. 12A shows representative images of immunostaining showing changes of GFAP (astrocyte), NG2 (NG2 cell), and Iba1 (microglia) signal before (D0) and up to one month after brain stab injury. Scale bar, 20 μm. n=3-4 animals for each quantification. A substantial increase of cell death (TUNEL), chondroitin sulfate proteoglycan (CSPG), and astrocytic gap junctions (Cx43) was also observed after stab injury. FIG. 12B shows representative images of TUNEL staining which showed significant cell death at day 2 and day 30 after stab injury, which was accompanied by increase in chondroitin sulfate proteoglycan (CSPG) and astrocytic gap junctions (labeled by Cx43). Scale bar, 20 μm. n=3-4 animals for each quantification.

Figure 12C:
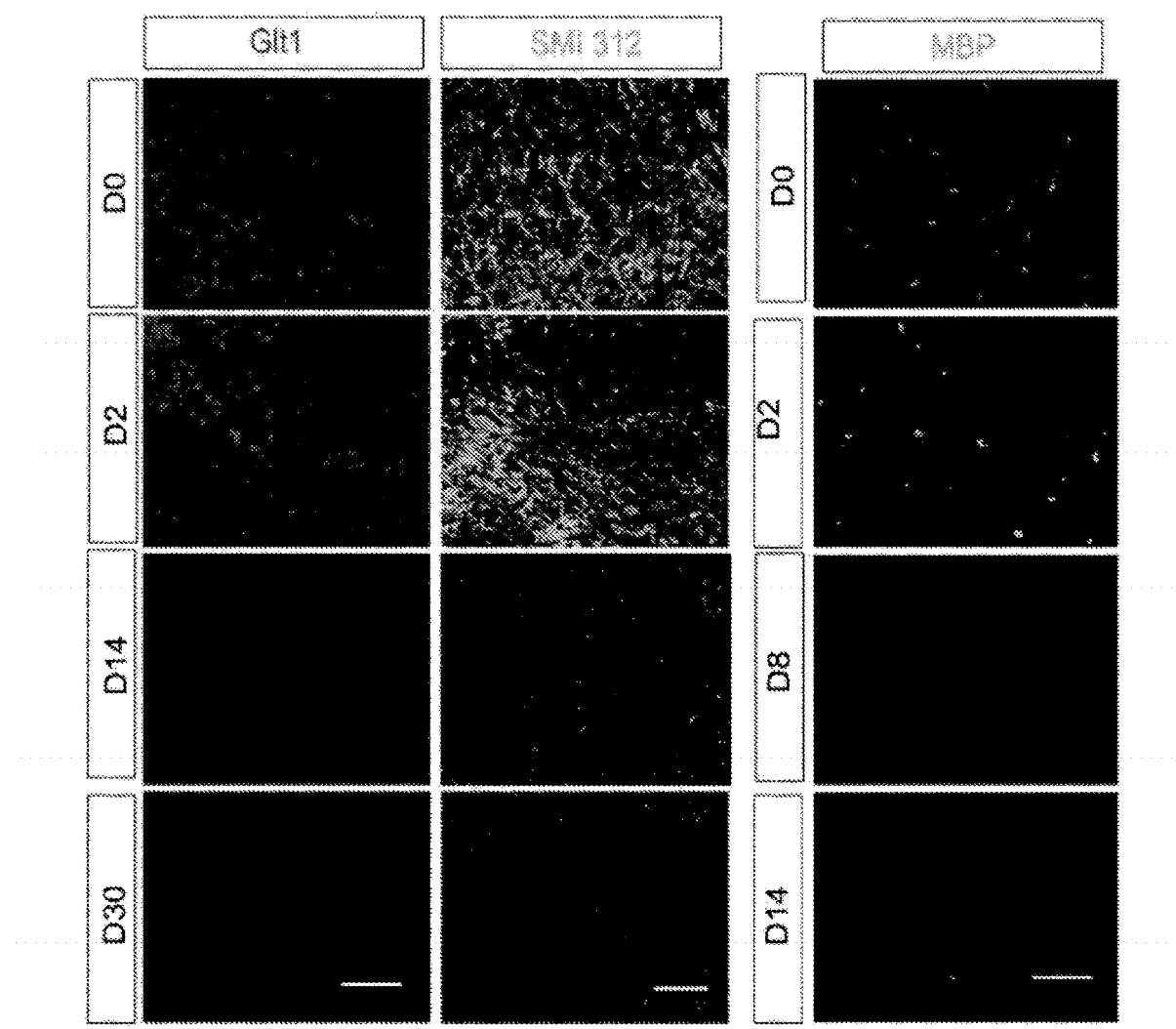
FIG. 12C shows representative images indicating a significant decrease of astrocytic glutamate transporter Glt1 and axon fibers.
Figure 12D:
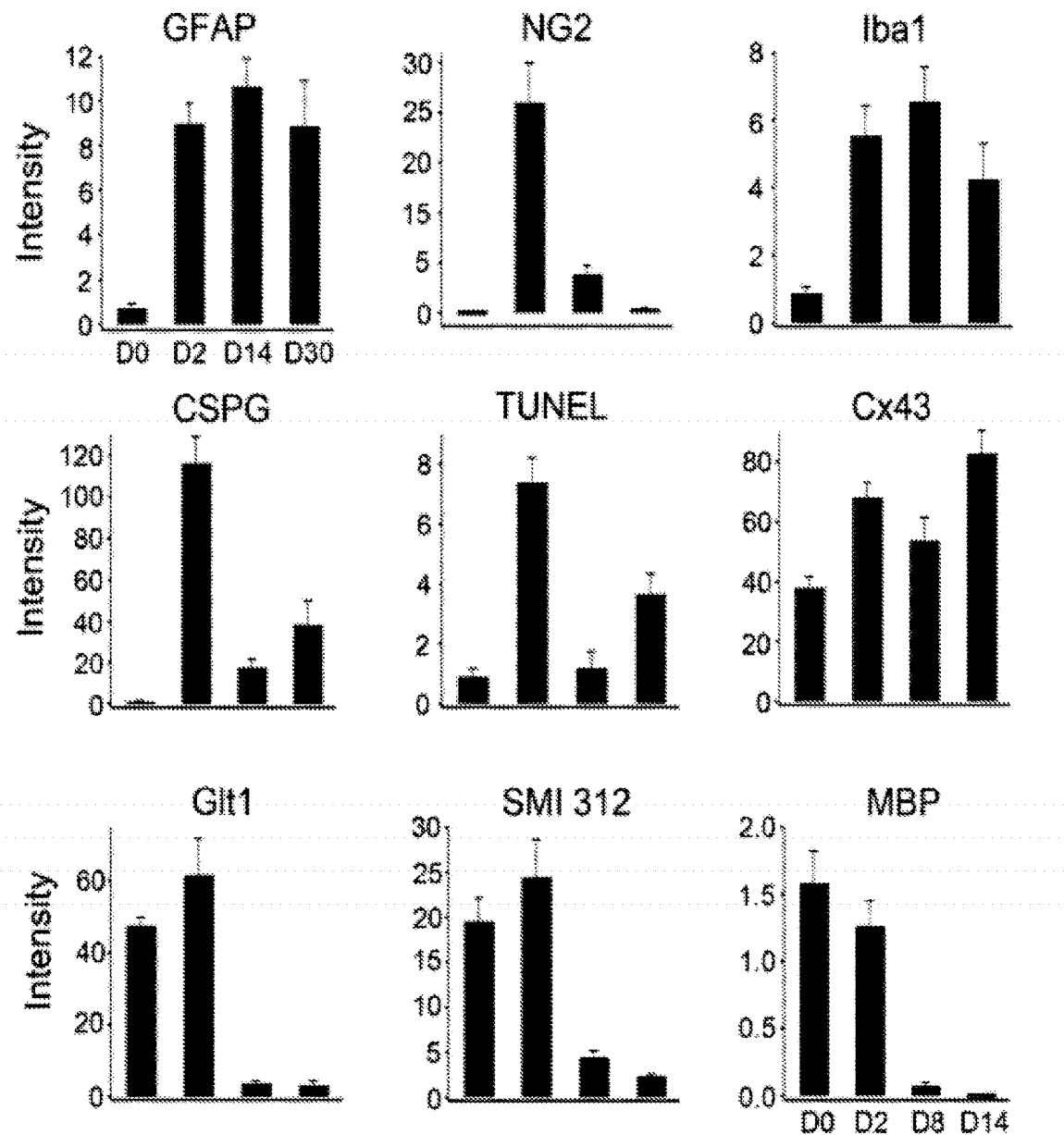
FIG. 12D shows bar graphs showing the quantified data of the immunostaining signal before and after brain injury.

TUNEL, CSPG, and Cx43 signals decreased at 2 weeks after injury, but increased again at 30 days after injury. Furthermore, the astrocytic glutamate transporter (Glt1), axon fibers (SMI312), and oligodendrocyte myelin proteins (MBP) all decreased after injury. FIG. 12C shows representative images indicating a significant decrease of astrocytic glutamate transporter Glt1 and axon fibers (labeled by SMI312) as well as myelin protein (MBP) after brain stab injury. Scale bar, 20 μm. n=3-4 animals for each quantification. FIG. 12D shows bar graphs showing the quantified data of the immunostaining signal before and after brain injury (D0-D30, except MBP). n=3-4 animals for each quantification.

Example 26

Figure 13A:
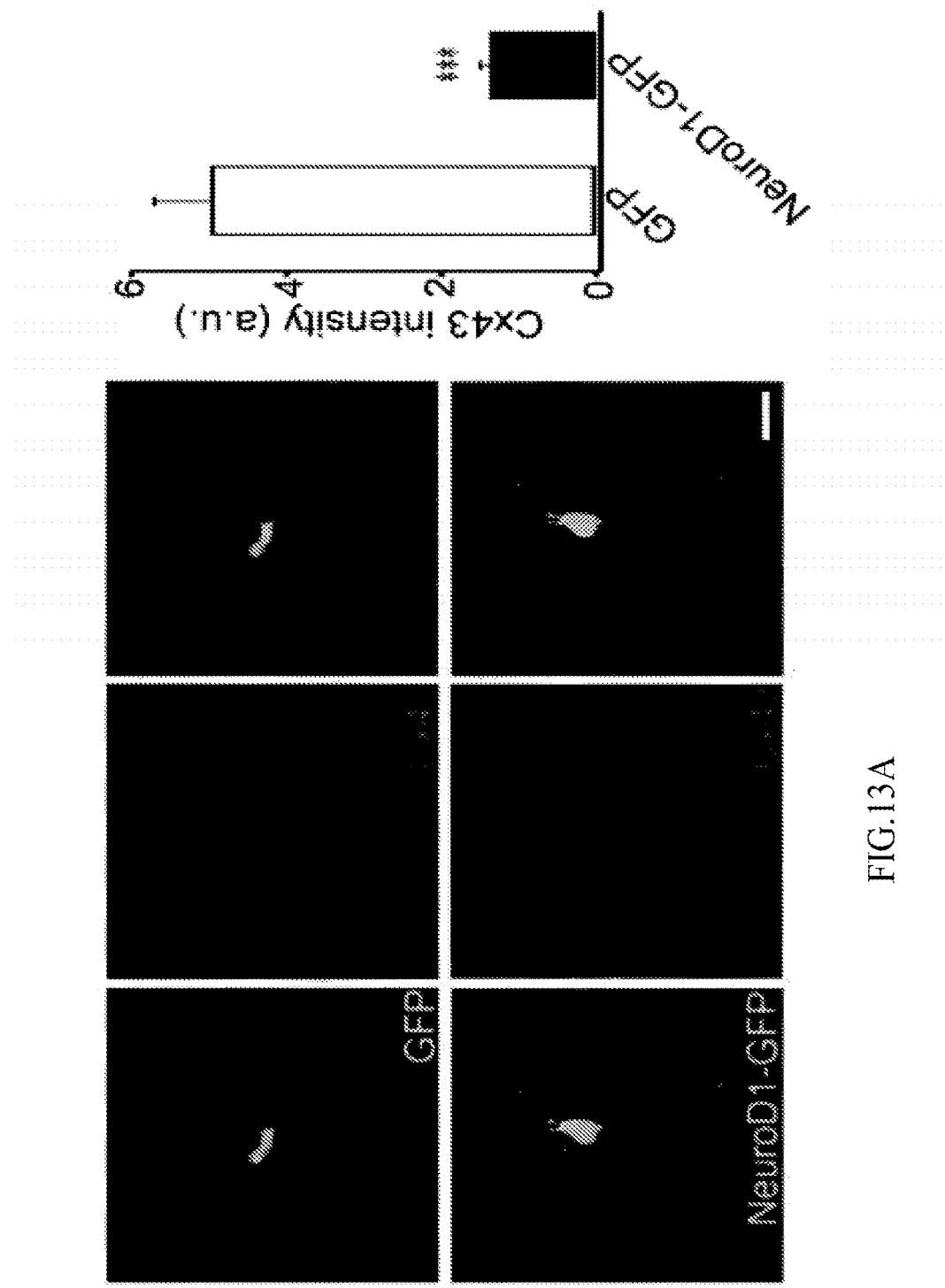
FIG. 13A includes images of GFP fluorescence, NeuroD1-GFP fluorescence, Cx43 immunostaining, and the overlap of GFP or NeuroD1-GFP and Cx43 immunostaining; and a graph showing that astrocytic gap junctions (Cx43) decreased in NeuroD1-infected regions compared to the control GFP retrovirus-infected areas.
Figure 13B:
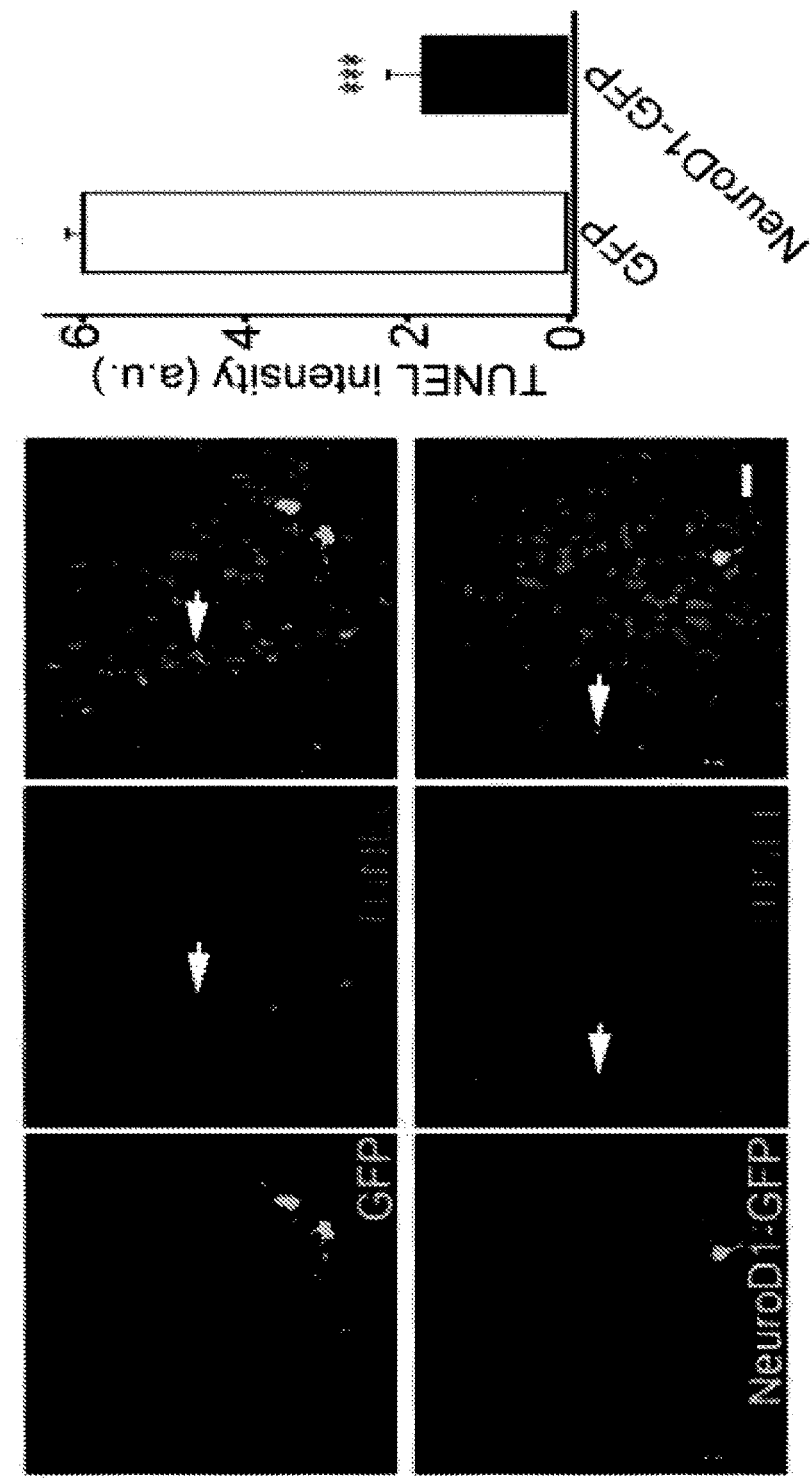
FIG. 13B includes images of GFP fluorescence, NeuroD1-GFP fluorescence, TUNEL staining, and the overlap of GFP or NeuroD1-GFP and TUNEL staining; and a graph showing that TUNEL staining showed reduced cell death in the regions containing NeuroD1-converted neurons.
Figure 13C:
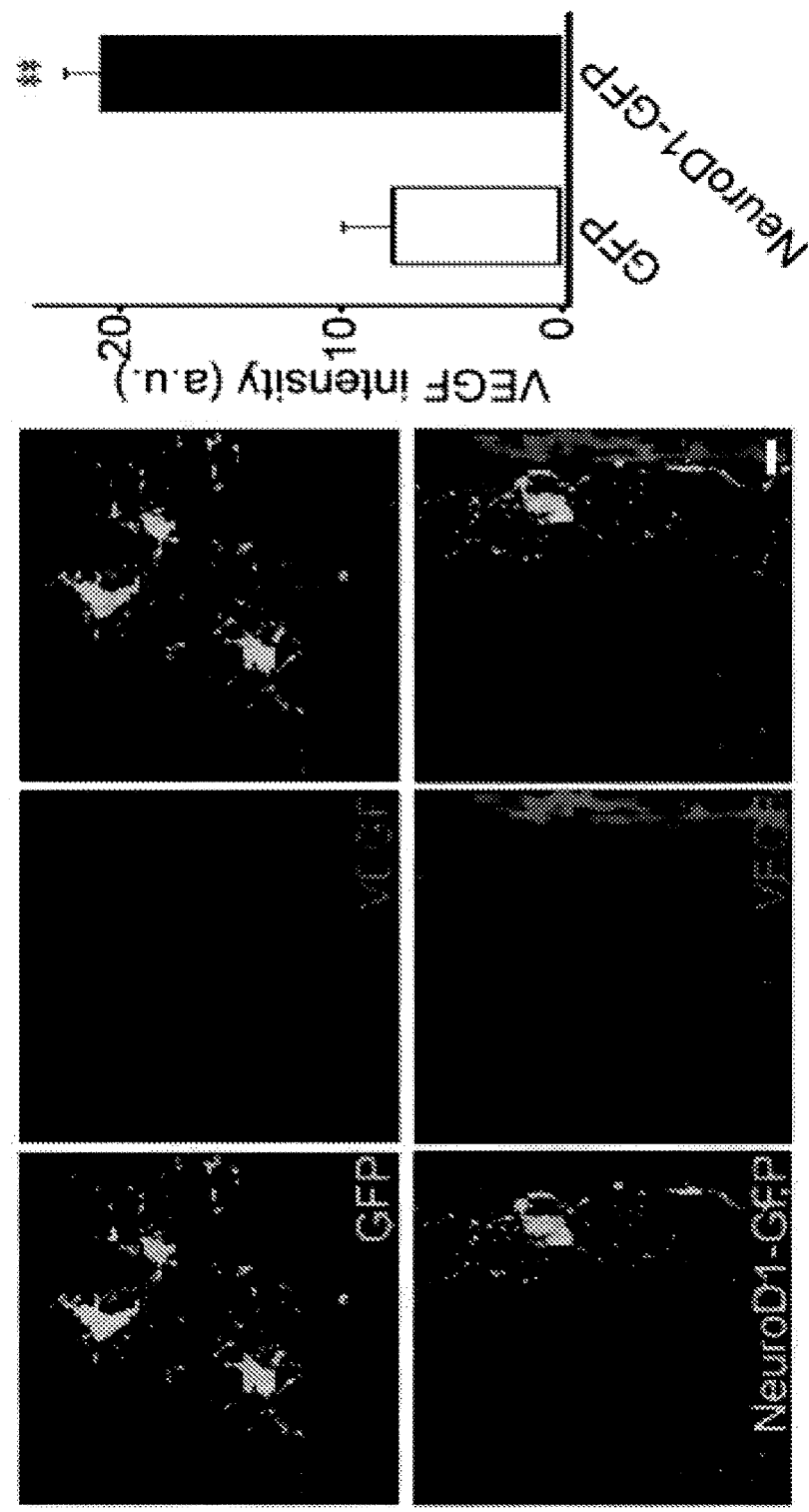
FIG. 13C includes images of GFP fluorescence, NeuroD1-GFP fluorescence, VEGF immunostaining, and the overlap of GFP or NeuroD1-GFP and VEGF immunostaining; and a graph showing that angiogenesis marker VEGF was significantly increased in the regions containing NeuroD1-converted neurons.
Figure 13D:
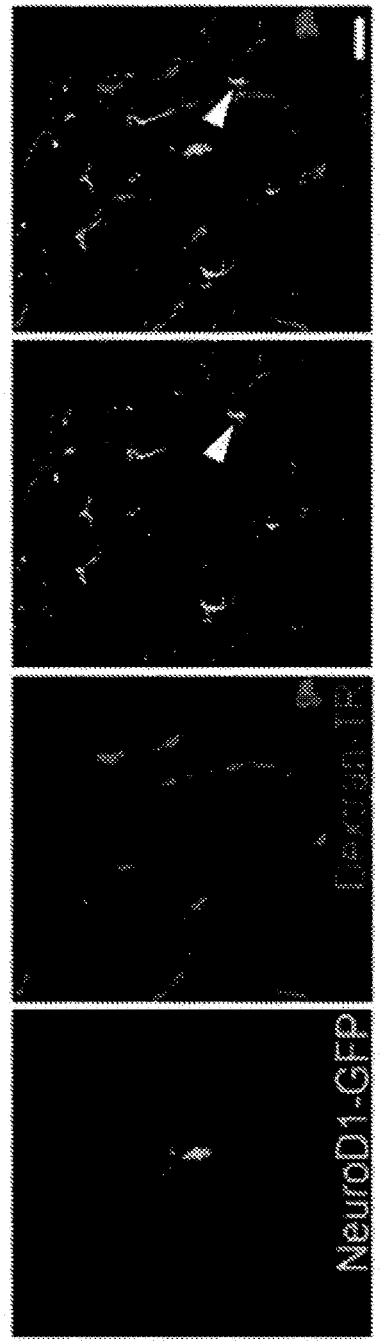
FIG. 13D shows representative images illustrating that in regions containing NeuroD1-converted neurons, astrocytes were closely contacting blood vessels.
Figure 13E:
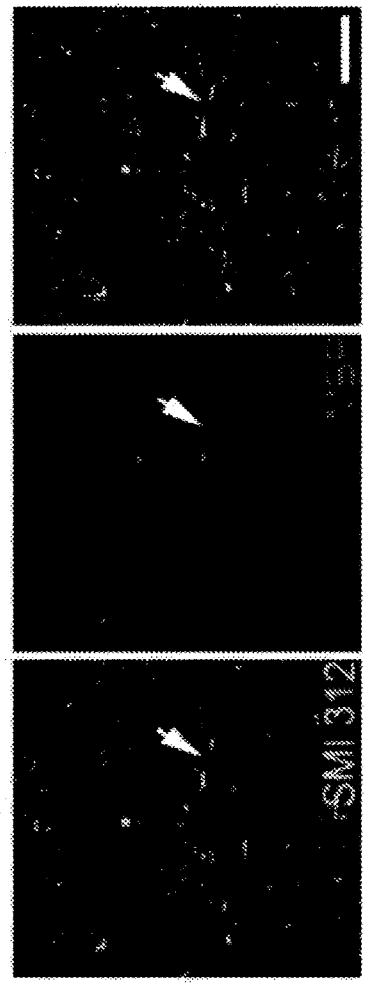
FIG. 13E shows representative images illustrating regions containing NeuroD1-converted neurons; and shows SMI312 immunostaining, MBP immunostaining and the overlap of SMI312 immunostaining and MBP immunostaining.

More Beneficial Effects after Conversion of Reactive Astrocytes and NG2 Cells into Functional Neurons by Expression of Exogenous NeuroD1 in the Injury Sites Additional beneficial effects including decreased gap junctions, decreased cell death, and increased VEGF in regions containing NeuroD1-converted neurons. FIG. 13A includes images of GFP fluorescence, top left or NeuroD1-GFP fluorescence, bottom left, Cx43 immunostaining, middle panels and the overlap of GFP or NeuroD1-GFP fluorescence and Cx43 immunostaining, right panels, top and bottom respectively, scale bar, 20 µm. FIG. 13A further includes a graph showing that astrocytic gap junctions (Cx43) decreased in regions infected with a retrovirus construct encoding NeuroD1 compared to the control areas infected with a retrovirus construct encoding GFP only (n=7). FIG. 13B includes images of GFP fluorescence, top left or NeuroD1-GFP fluorescence, bottom left, TUNEL staining, middle panels and the overlap of GFP or NeuroD1-GFP and TUNEL staining, right panels, top and bottom respectively, scale bar, 20 µm. FIG. 13B further includes a graph showing that TUNEL staining showed reduced cell death in the regions containing NeuroD1-converted neurons (n=5). FIG. 13C includes images of GFP fluorescence, top left or NeuroD1-GFP fluorescence, bottom left. VEGF immunostaining, middle panels and the overlap of GFP or NeuroD1-GFP and VEGF immunostaining, right panels, top and bottom respectively, scale bar, 10 µm. FIG. 13C further includes a graph showing that angiogenesis marker VEGF was significantly increased in the regions containing NeuroD1-converted neurons (n=6). FIG. 13D shows representative images illustrating that in regions containing NeuroD1-converted neurons, astrocytes were closely contacting blood vessels (n=6), scale bar, 40 µm. FIG. 13E shows representative images illustrating that in regions containing NeuroD1-converted neurons, SMI312-labeled axon fibers were co-localizing with myelin protein MBP (n=4), scale bar, 20 µm. In FIG. 13E SMI312 immunostaining is shown in the left panel, MBP immunostaining in the middle left panel and the overlap of SMI312 immunostaining and MBP immunostaining is shown in the panel on the right.

Example 27

Figure 14A:
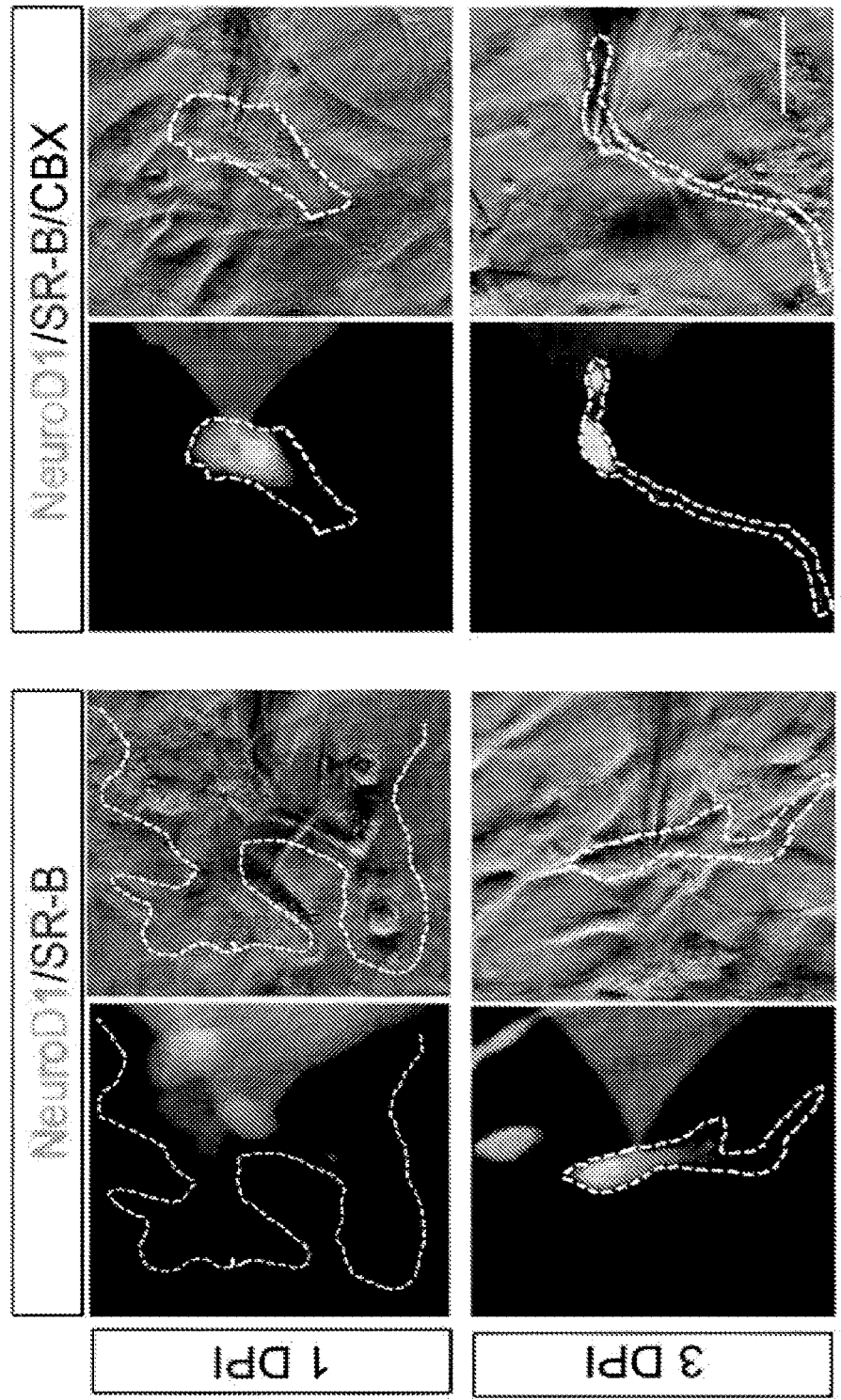
FIG. 14A shows representative images of dialysis of sulforhodamine B into 1 day old NeuroD1-converted neuron.
Figure 14B:
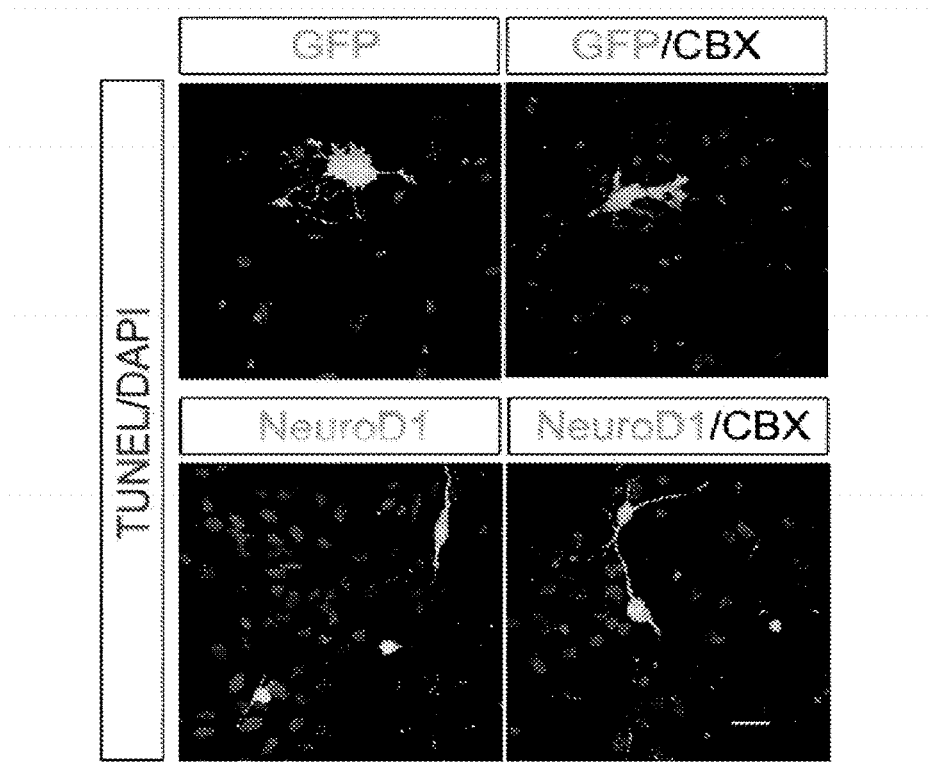
FIG. 14B shows representative images of NeuroD1-induced conversion of astrocytes into neurons.
Figure 14C:
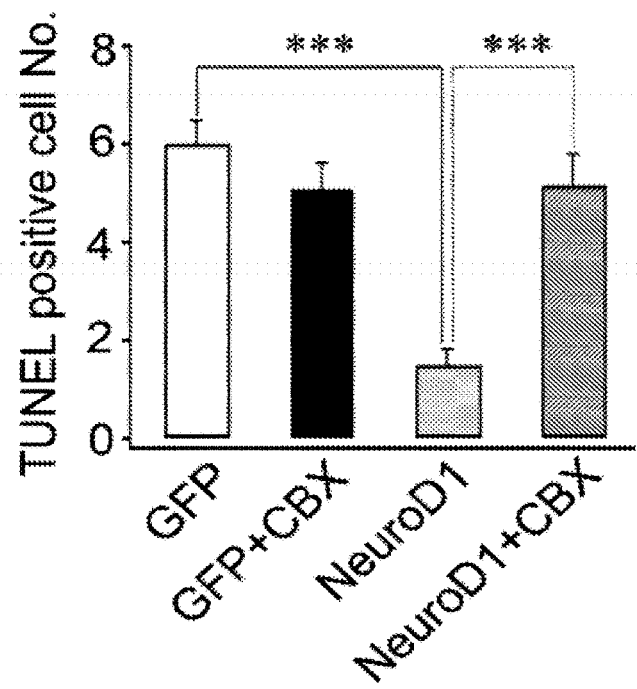
FIG. 14C is a graph showing quantitation of these results.

Gap Junction Coupling Between Newly Converted Neurons and Surrounding Astrocytes Gap junction-mediated trans-cellular signaling may mediate beneficial effects of conversion of astrocytes to neurons by expression of exogenous NeuroD1. Astrocytes are coupled with gap junctions and brain injury increases astrocytic gap junctions, see FIG. 12B. The studies described herein showed that during the early stage of astrocyte-neuron conversion, gap junctions might remain between astrocytes and new NeuroD1-converted neurons, see FIG. 2G. Further results showed that injecting dye (sulforhodamine B) into 1-day old NeuroD1-converted neurons resulted in the spreading of the dye into neighboring astrocytes (FIG. 14A). The dye coupling was blocked by gap junction inhibitor carbenoxolone (CBX), see FIG. 14A. Interestingly, injecting dye into 3-day old NeuroD1-converted neurons did not have dye coupling anymore, suggesting that gap junctions only remained for a short period after the conversion, see FIG. 14A. To investigate whether such neuron-astrocyte gap junction had any functional significance, we used LPS (100 µM) to induce cell death in our cell cultures. Compared to the GFP control retrovirus, infection with a retrovirus encoding NeuroD1 significantly decreased the number of cell deaths, and such beneficial effect was blocked by gap junction inhibitor. Thus, converting reactive glial cells into functional neurons by expression of exogenous NeuroD1 significantly improves injured areas by increasing axon fibers and blood vessels while decreasing cell death. FIG. 14A shows representative images showing that dialysis of sulforhodamine B into 1 day old NeuroD1-converted neuron labeled surrounding astrocytes as outlined by dashed line and that such dye coupling was not seen in 3-day old converted neurons or after blocking gap junctions with carbenoxolone (CBX, 100 µM). Scale bar, 20 µm. n=3 cultures. FIG. 14B shows representative images showing that NeuroD1-induced conversion of astrocytes into neurons significantly reduced cell death (labeled by TUNEL staining). Blocking gap junction with CBX increased cell death. Scale bar, 20 µm. n=4 cultures. TUNEL cell number was counted per 60× image (area=0.044 mm$^2$). FIG. 14C is a graph showing quantitation of these results.

Example 28

Figure 15A:
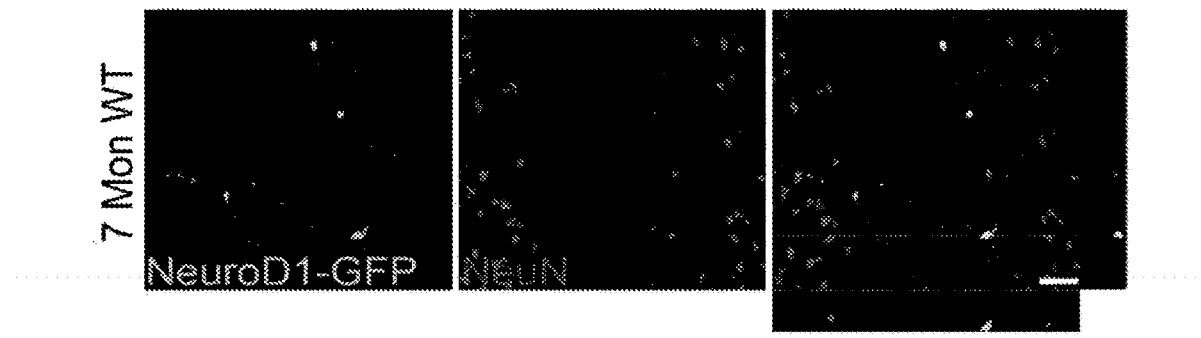
FIG. 15A shows representative images indicating that cells infected with a retrovirus encoding NeuroD1 and GFP (14 DPI) were positive for NeuN in 7-month old WT mice; and shows NeuroD1-GFP fluorescence, NeuN immunostaining and the overlap of NeuroD1-GFP fluorescence and NeuN immunostaining in the same field.

NeuroD1 can Convert Reactive Astrocytes and NG2 Cells into NeuroD1-Converted Neurons in Aging Animals Injection of a retrovirus encoding NeuroD1 into very old brain, 14 month old WT or AD brain, was found to convert reactive glial cells into neurons. FIG. 15A shows representative images indicating that cells infected with a retrovirus encoding NeuroD1 and GFP (14 DPI) were positive for NeuN in 7-month old WT mice (n=4), scale bar, 40 µm. In FIG. 15A, NeuroD1-GFP fluorescence is shown in the left panel, NeuN immunostaining is shown in the middle panel and the overlap of NeuroD1-GFP fluorescence and NeuN immunostaining in the same field is shown in the right panel.

Figure 15B:
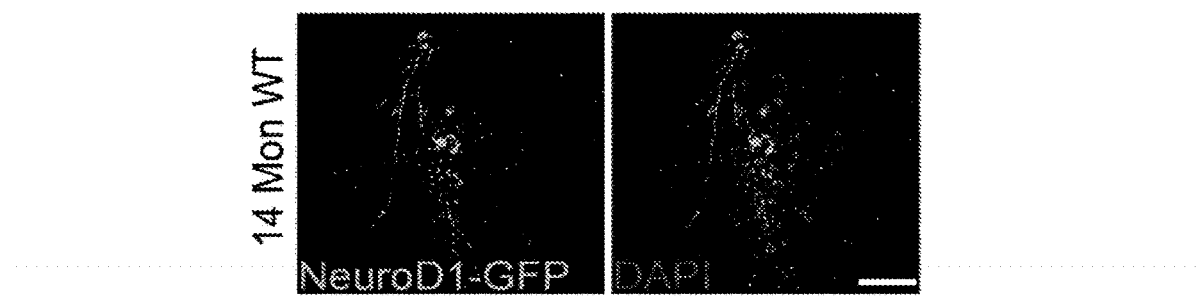
FIG. 15B shows representative images indicating that NeuroD1-converted neurons (16 DPI) showed robust dendrites in 14 month old animals.
Figure 15C:
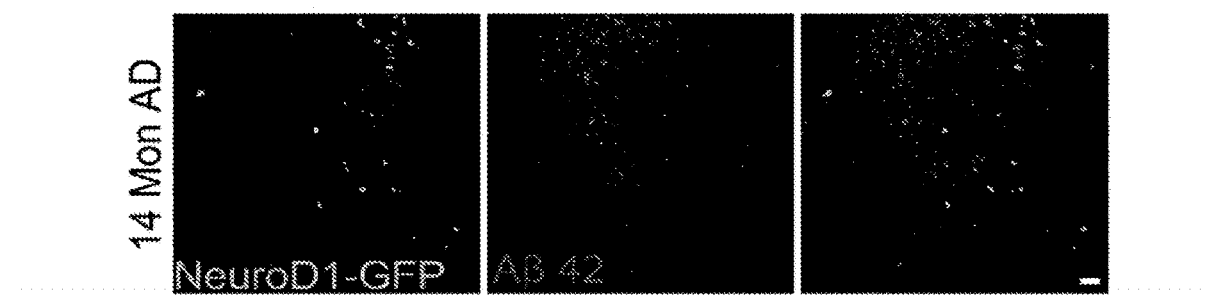
FIG. 15C shows NeuroD1-GFP fluorescencel, Aβ42 immunostaining and the overlap of NeuroD1-GFP fluorescence and Aβ42 immunostaining in the same field.

FIG. 15B shows representative images indicating that NeuroD1-converted neurons (16 DPI) showed robust dendrites in 14 month old animals (n=3), scale bar, 40 µm. In FIG. 15B, NeuroD1-GFP fluorescence is shown in the left panel and the overlap of NeuroD1-GFP fluorescence and DAPI fluorescence in the same field is shown in the right panel. FIG. 15C shows representative images indicating that even in 14 month old 5xFAD mice, there were many NeuroD1-converted neurons (14 DPI) in the vicinity of Aβ deposits (n=6), scale bar, 40 µm. This result suggests that NeuroD1 conversion method may be used in aging brains to restore lost neuronal functions. In FIG. 15C, NeuroD1-GFP fluorescence is shown in the left panel, Aβ42 immunostaining is shown in the middle panel and the overlap of NeuroD1-GFP fluorescence and Aβ42 immunostaining in the same field is shown in the right panel.

Example 29

No Intermediate Neuroprogenitor Stage During Human Astrocyte-Neuron Conversion

Figure 16:
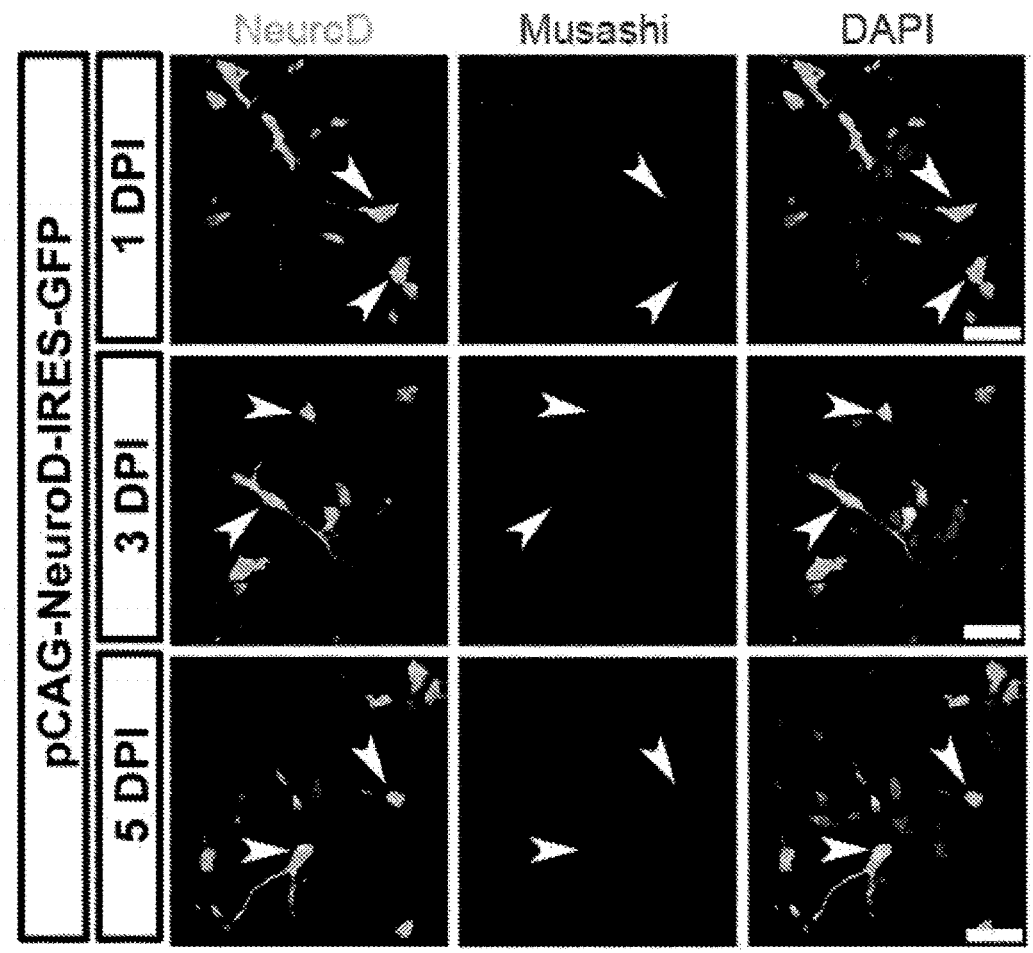
FIG. 16 shows NeuroD1-GFP fluorescence, Musashi immunostaining and the overlap of NeuroD1-GFP fluorescence and Musashi immunostaining in the same field.

FIG. 16 shows representative images indicating that cells infected with a retrovirus encoding NeuroD1 (arrowheads) did not show any increase in the expression of neural stem cell marker Musashi over 1, 3 and 5 days post infection (DPI). Scale bar, 40 µm. n=3 cultures. In FIG. 16, NeuroD1-GFP fluorescence is shown in the left panel, Musashi immunostaining is shown in the middle panel and the overlap of NeuroD1-GFP fluorescence and Musashi immunostaining in the same field is shown in the right panel, along with DAPI fluorescence.

Example 30

Properties of Human Astrocyte-Converted Neurons after NeuroD1 Infection

Figure 17A:
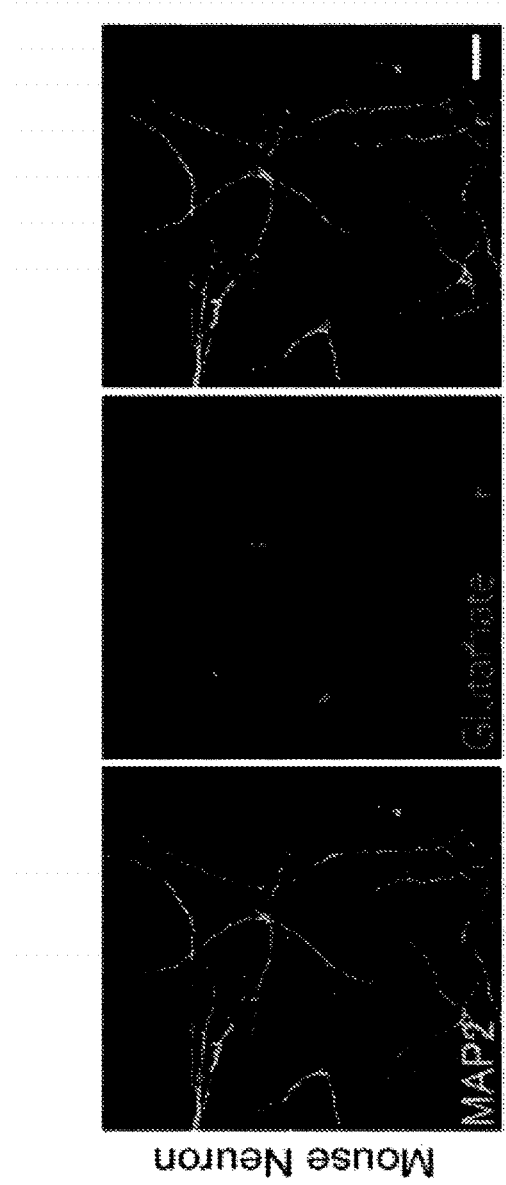
FIGS. 17A and 17B are representative images showing glutamate immunostaining in mouse cultured neurons.
Figure 17B:
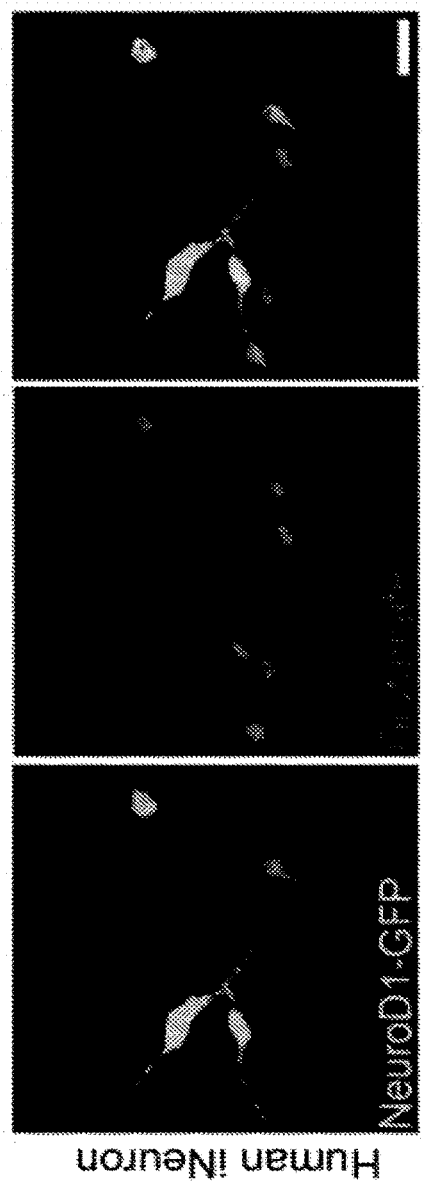

FIG. 17A and FIG. 17B are representative images showing glutamate immunostaining in mouse cultured neurons (7

DIV) and NeuroD1-converted neurons generated by infection of human astrocytes with a retrovirus encoding NeuroD1 (21 DPI, 98.4±0.9% positive for glutamate), respectively, scale bars, 40 for FIG. 17A, 20 μm for FIG. 17B. n=3 cultures.

FIG. 17C and FIG. 17D are representative images showing GABA immunostaining in mouse cultured neurons (7 DIV) and NeuroD1-converted neurons generated by infection of human astrocytes with a retrovirus encoding NeuroD1 (21 DPI, 1.4±0.1% positive for GABA), respectively, scale bars, 40 μm. n=3 cultures.

Figure 17E:
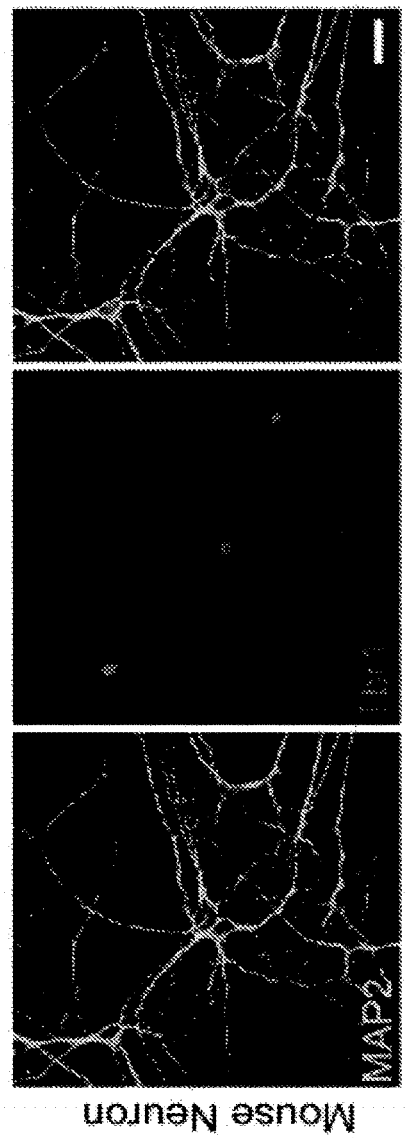
FIGS. 17E and 17F are representative images showing Tbr1 immunostaining in mouse cultured neurons.
Figure 17F:
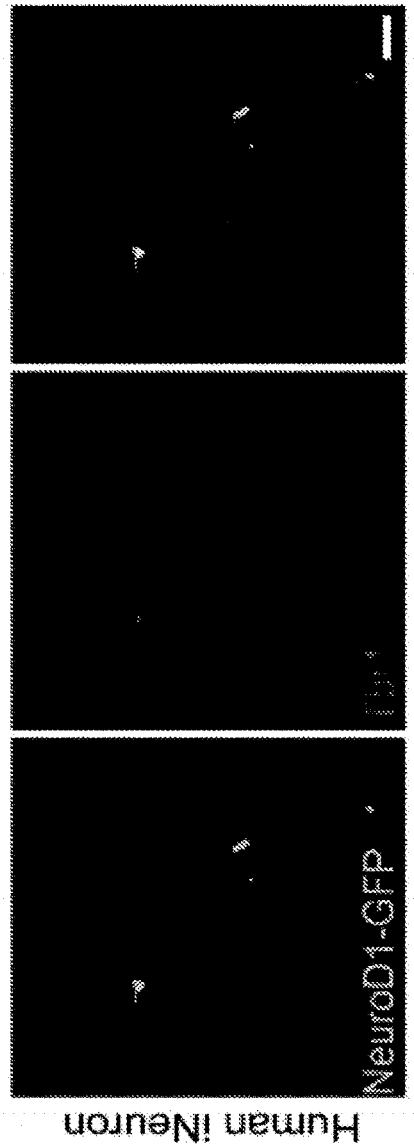

FIG. 17E and FIG. 17F are representative images showing Tbr1 immunostaining in mouse cultured neurons (7 DIV) and NeuroD1-converted neurons generated by infection of human astrocytes with a retrovirus encoding NeuroD1 (21 DPI), respectively, scale bars, 40 μm.

Example 31

Human Astrocytes can be Converted into Neurons Whereas Human Microglia Cannot

Figure 18A:
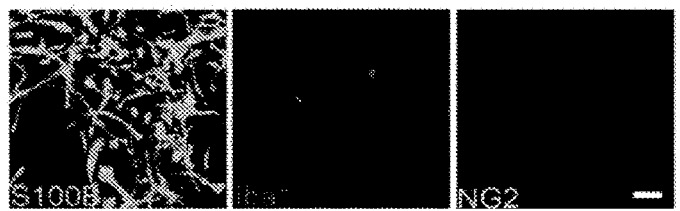
FIG. 18A shows representative images indicating that the majority of cells in human astrocyte cultures were immunopositive for astrocyte marker S100β.
Figure 18B:
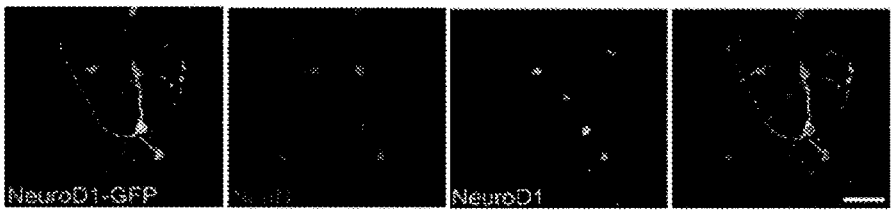
FIG. 18B shows representative images indicating that NeuroD1-GFP infected human astrocytes became immunopositive for NeuN.
Figure 18C:
FIG. 18C shows representative images indicating that NeuroD1-converted neurons generated by infection of human astrocytes with a retrovirus encoding NeuroD1 were positive for Prox1.
Figure 18D:
FIG. 18D shows representative images indicating that the majority of cells in human microglia cultures were positive for Iba1.
Figure 18E:
FIGS. 18E and 18F are representative images showing that human microglia could not be converted into neurons by NeuroD1.
Figure 18F:

FIG. 18A shows representative images indicating that the majority of cells in human astrocyte cultures were immunopositive for astrocyte marker S100β (94.3±0.7%), n=3-5 cultures, scale bar, 40 μm. FIG. 18B shows representative images indicating that NeuroD1-GFP infected human astrocytes became immunopositive for NeuN (21 DPI), n=3-5 cultures, scale bar, 40 μm. The NeuroD1 expression was confirmed by NeuroD1 immunostaining. FIG. 18C shows representative images indicating that NeuroD1-converted neurons generated by infection of human astrocytes with a retrovirus encoding NeuroD1 were positive for Prox1 (8 DPI), n=3-5 cultures, scale bar, 40 μm. FIG. 18D shows representative images indicating that the majority of cells in human microglia cultures were positive for Iba1 (97.1±1.1%), n=3-5 cultures, scale bar, 40 μm. FIG. 18E and FIG. 18F are representative images showing that human microglia could not be converted into neurons by NeuroD1 (20 DPI), n=3-5 cultures, scale bar, 40 μm. FIG. 18G is a graph showing quantitation of cultured human astrocytes immunopositive for S100β (94.3±0.7%), Iba1 and NG2. FIG. 18H is a graph showing quantitation of cultured human microglia immunopositive for GFAP, Iba1 (97.1±1.1%) and NG2.

Example 32

NG2 Promoter-Driven NeuroD1 Expression In Vivo and In Vitro

Figure 19A:
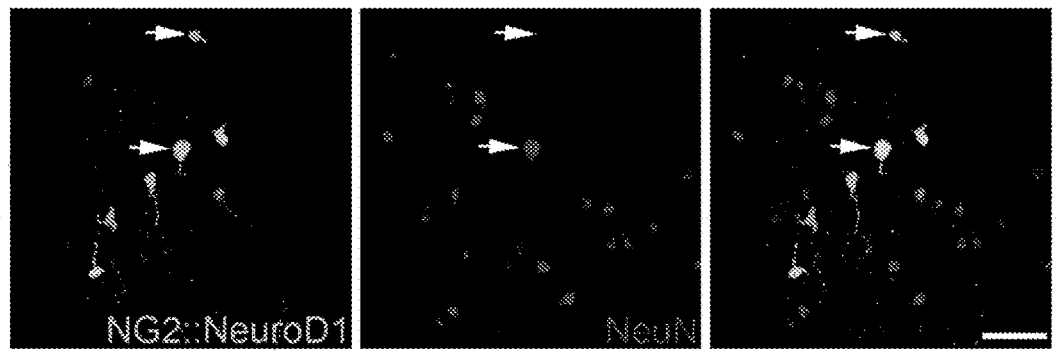
FIG. 19A shows representative images obtained after injecting hNG2::NeuroD1-IRES-GFP retrovirus into one month old mouse cortex.

A retrovirus encoding NeuroD1 and GFP under the control of human NG2 promoter, hNG2::NeuroD1-IRES-GFP, was generated and used to infect cells in adult mouse cortex. After injecting hNG2::NeuroD1-IRES-GFP retrovirus into adult mouse cortex, NeuroD1-infected NG2 cells, identified by GFP fluorescence, were immunopositive for NeuN, indicating that NG2 cells were indeed converted into neurons in vivo; 7 DPI. FIG. 19A shows representative images obtained after injecting hNG2::NeuroD1-IRES-GFP retrovirus into one month old mouse cortex. GFP fluorescence is shown in the left panel, NeuN immunofluorescence is shown in the middle panel, identifying NeuN-positive neurons in vivo, arrows, 7 DPI. n=4 animals. The overlap of GFP fluorescence and NeuN immunofluorescence is shown in the same field in the right panel. Scale bar: 40 μm.

Figure 19B:
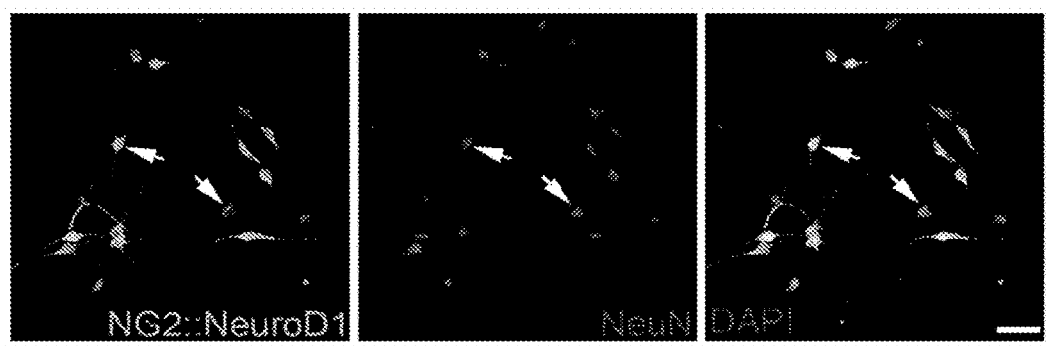
FIG. 19B shows representative images obtained after infecting cultured NG2 cells with hNG2::NeuroD1-IRES-GFP retrovirus.

Cultured NG2 cells were infected with hNG2::NeuroD1-IRES-GFP and many NeuN-positive neurons with clear neuronal morphology in NeuroD1-infected NG2 cultures were found; 7 DPI. Thus, NG2 cells can be converted into neurons by NeuroD1. FIG. 19B shows representative images obtained after infecting cultured NG2 cells with hNG2::NeuroD1-IRES-GFP retrovirus. GFP fluorescence is shown in the left panel, NeuN immunofluorescence is shown in the middle panel, identifying NeuN-positive neurons in vivo, arrows, 7 DPI. The overlap of GFP fluorescence and NeuN immunofluorescence, along with DAPI staining, is shown in the same field in the right panel. Scale bar: 40 μm.

Example 33—Animal Model of Focal Ischemic Stroke I

In this example, a mouse model for endothelin-1 induced focal ischemic stroke is used to determine the effects of expression of exogenous NeuroD1 in glial cells in the stroke injured brain.

Animals: 3-5 month old C57BL/6 male mice (20-30 gram) are housed in standard cage of animal facility of Penn State University on a 12:12 light/dark cycle. Mice are maintained on a restricted feeding schedule (3 g/day) to prevent satiation and motivate reaching performance. One group of mice receives intracortical infusions of endothelin-1 (ET-1); one group of mice receives intracortical infusions of 0.9% sterile saline; one group of mice receives sham procedures.

Surgery procedure: Mice are anesthetized by using 0.25% Avertin (dissolved in sterile saline, 20 ml/kg, i.p.). Tail/foot pinch and corneal response is tested to verify full anesthetization. Temperature is maintained at 37° C. through a thermal pad during surgery. The scalp is shaved and cleaned with iodine, then injected with bupivacaine (1 ml/20 g, s.c.). Each mouse is then placed in a stereotaxic apparatus; a midline incision is made along the length of shaved area. A small burr hole is drilled through the skull over the center of the forelimb region of the sensorimotor cortex at coordinates of 2.25 mm lateral to midline and +0.6 mm anterior to Bregma. The dura mater is punctured and a 1 ml syringe with a 26 gauge needle is lowered into the cortex to a depth of 700 μm. 4 μl of ET-1 (320 pmol, 0.2 μg/μl in sterile saline) is injected into the cortex for 10 min, and the syringe is left in place for 5 min post-injection to prevent backflow before slowly removed. The burr hole is then filled with gelfoam and covered with UV curing dental cement, and the wound is sutured and covered in antibiotic ointment. After surgery the animal is placed on the thermal pad till fully awaken before returning to its home cage. Of the two sham groups, one group receives all surgical procedures up to the skull opening and the other receives a skull opening and infusion of vehicle (0.9% sterile saline) into the forelimb area of the sensorimotor cortex. Mice are checked in the following days (4-5 days) after surgery to ensure the normal recovery of mice.

A behavioral test, the bilateral tactile stimulation test, can be used to assess the induced stroke. For this test, each mouse is placed into a shallow transparent plastic container (8.5 cm tall, 18 cm in diameter) with an open top and allowed to habituate for 1 min. The mouse is picked up and lightly restrained by the scruff while a 1.27 cm long piece of 3 mm wide tape is placed onto the ventral side of each paw. The mouse is then placed back into the container and allowed to remove each piece of tape using its teeth. The latency to contact and remove each piece of tape is recorded for five trials, allowing 30 s of rest between each trial.

NeuroD1 retrovirus including SEQ ID NO: 2 or SEQ ID NO: 4 is generated as described in Example 3 and injected into the cortex of mice as described in Example 7. After about two weeks following the injection of NeuroD1, the brains will be examined to confirm an increase in neurons in the vicinity of the NeuroD1 retrovirus injection. The bilateral tactile stimulation test can be used to assess improvement of stroke-related behavioral effects.

Example 34—Animal Model of Focal Ischemic Stroke II

In this example, a mouse model for photothrombosis-induced focal ischemic stroke is used to determine the effects of expression of exogenous NeuroD1 in glial cells in the stroke injured brain.

Animals: 3-5 month old C57BL/6 male mice (20-30 gram) are housed in standard cage of animal facility of Penn State University on a 12:12 light/dark cycle. Mice are maintained on a restricted feeding schedule (3 g/day) to prevent satiation and motivate reaching performance. Surgery procedure: Mice are anesthetized by using 0.25% Avertin (dissolved in sterile saline, 20 ml/kg body weight, i.p.). Tail/foot pinch and corneal response is tested to verify full anesthetization. Temperature is maintained at 37° C. through a thermal pad during surgery. The skin above the skull is incised, and a fiber-optic bundle mounted on a cold light source (diameter 5 1.5 mm, wavelength 560 nm, aperture B2, 1750K, KL 1500 LCD) is placed over the right hemisphere with a focus at 2.25 mm lateral to midline and +0.6 mm anterior to Bregma. The photosensitive dye rose Bengal (dissolved in artificial cerebral spinal fluid) is injected into the lateral tail vein (30 mg/kg body weight). Focal illumination of the skull starts immediately after the injection, which lasts for 20 min. After the induction of thrombosis, the incision is sutured and the animal is placed on the thermal pad till fully awaken before returning to its home cage. The placement of the light beam, the light intensity, and the light aperture are the same for all animals. Of the sham group, mice receive all surgical procedures except for light irradiation. Mice are checked in the following days (4-5 days) after surgery to ensure the normal recovery of mice.

A behavioral test, the bilateral tactile stimulation test, can be used to assess the induced stroke. For this test, each mouse is placed into a shallow transparent plastic container (8.5 cm tall, 18 cm in diameter) with an open top and allowed to habituate for 1 min. The mouse is picked up and lightly restrained by the scruff while a 1.27 cm long piece of 3 mm wide tape is placed onto the ventral side of each paw. The mouse is then placed back into the container and allowed to remove each piece of tape using its teeth. The latency to contact and remove each piece of tape is recorded for five trials, allowing 30 s of rest between each trial.

NeuroD1 retrovirus including SEQ ID NO: 2 or SEQ ID NO: 4 is generated as described in Example 3 and injected into the cortex of mice as described in Example 7. After about two weeks following the injection of NeuroD1, the brains will be examined to confirm an increase in neurons in the vicinity of the NeuroD1 retrovirus injection. The bilateral tactile stimulation test can be used to assess improvement of stroke-related behavioral effects.

Example 35—Animal Model of Spinal Cord Injury

In this example, a mouse model for spinal cord injury is used to determine the effects of expression of exogenous NeuroD1 in glial cells in the injured spinal cord.

Animals to be used in this example are female C57B/6 mice (22-29 g) Prior to surgery a heating pad is pre-heated to maintain a temperature range of 36.6-37.1° C. throughout the whole surgery process. Mice are anesthetized by injecting 15 ml/kg 0.25% Avertin into the peritoneum. After mouse is immobilized shave the skin of back. Cover eyes with ointment. Place the mouse on the heating pad with back up, disinfecting the back twice with 70% alcohol. Before proceeding the mouse is checked to insure that there is no reflex to a toe pinch. Then, a 1.3 cm dorsal median incision is to be made over the thoracic vertebral column incision on the back. The caudal part of the nuchal ligament and the underlying trapezius muscle from its origin of the spinal processes is cut to expose the spinous processes of T8-T10. A fine pair of rongeurs is used to make a laminectomy of vertebra T9-T10, being careful not to damage the dura. Once the spinal cord is exposed, either of two methods will be used for injury: 1) using a pair of forceps, the spinal process of T9 is held and lifted to open the intervertebral space. A pair of modified forceps is used to laterally compress the spinal cord to the thickness of 0.3 mm and is held with the forceps for 15 sec or 2) a pair of forceps is used to hold and slightly lift the spinal process of T9 to open the intervertebral space. The cord is transected with a microscalpel (5 mm blade depth, 15°; Roboz Surgical Instruments) in one movement from the right to the left. The cut is redone a second time from the left to the right taking great care to slide with the tip of the scalpel over the osseous surface of the spinal canal to ensure complete transection. A sham injury control group will receive identical treatment, including exposure, laminectomy and placement of the forceps around the spinal cord, but no crush or transaction injury would be inflicted. The breath and heartbeat of each animal is monitored throughout the whole surgery procedure. Then, the autochtone muscles and the trapezius muscles of both sides are repositioned and gently opposed muscles by closed three single sutures using 10-0 Ethilon (7718G, Ethicon). The skin is closed with the same suture.

Post-surgery care: each mouse is kept on a heating pad until it wakes up after which it is transferred to its cage with bedding, enough water and soft food.

Immediately following the surgery and for an additional day, 1 ml Ringer's solution for hydration and buprenorphine (0.01 mg/kg) will be subcutaneously injected twice daily for 3 days to alleviate pain. Each mouse is checked every day post-surgery and the bladder manually evacuated twice daily until the mouse can spontaneously micturate. Each mouse will be intraperitoneally injected with 0.01 ml antibiotics Baytril to prevent bladder infection.

NeuroD1 retrovirus including SEQ ID NO: 2 or SEQ ID NO: 4 is generated as described in Example 3 and will be injected into the spinal cord of mice at the site of the spinal cord injury. After about two weeks following the injection of NeuroD1, the spinal cords will be examined to confirm an increase in neurons in the vicinity of the NeuroD1 retrovirus injection.

Example 36—Effect of Expression of Exogenous Dlx2 Converted Human Astrocytes into GABAergic and Glutamatergic Neurons in Cell Culture Expression of exogenous Dlx2 in cultured human astrocytes changed astrocytes into GAD-positive GABAergic neurons, which showed repetitive action potentials and GABAergic events. Occasionally, some glutamatergic events were also detected, suggesting that Dlx2 can convert human astrocytes into both GABAergic and glutamatergic neurons.

Example 37—Converting Reactive Astrocytes into Neurons in Non-Human Primates Conversion of reactive astrocytes into neurons will be performed using non-human primates, such as marmoset or macaque monkeys, to introduce human NeuroD1 into reactive astrocytes after stroke (similar to that described in Example 33 and 34) or spinal cord injury (similar to that described in Example 35) to convert them into functional neurons. NeuroD1 can be introduced into animals through retrovirus or adeno-associated virus that contain astroglial specific promoter GFAP to allow expression of NeuroD1 only in astrocytes. Nanoparticles that can bind with plasmids or viral particles can also be used to introduce NeuroD1 into glial cells for neuronal conversion.

Sequences

```
SEQ ID NO: 1-Human NeuroD1 nucleic acid sequence encoding human NeuroD1
protein-1071 nucleotides, including stop codon
ATGACCAAATCGTACAGCGAGAGTGGGCTGATGGGCGAGCCTCAGCCCCAAGGTCCTCCAAGCT

GGACAGACGAGTGTCTCAGTTCTCAGGACGAGGAGCACGAGGCAGACAAGAAGGAGGACGACCT

CGAAGCCATGAACGCAGAGGAGGACTCACTGAGGAACGGGGGAGAGGAGGAGGACGAAGATGAG

GACCTGGAAGAGGAGGAAGAAGAGGAAGAGGAGGATGACGATCAAAAGCCCAAGAGACGCGGCC

CCAAAAAGAAGAAGATGACTAAGGCTCGCCTGGAGCGTTTTAAATTGAGACGCATGAAGGCTAA

CGCCCGGGAGCGGAACCGCATGCACGGACTGAACGCGCGCTAGACAACCTGCGCAAGGTGGTG

CCTTGCTATTCTAAGACGCAGAAGCTGTCCAAAATCGAGACTCTGCGCTTGGCCAAGAACTACA

TCTGGGCTCTGTCGGAGATCCTGCGCTCAGGCAAAAGCCCAGACCTGGTCTCCTTCGTTCAGAC

GCTTTGCAAGGGCTTATCCCAACCCACCACCAACCTGGTTGCGGGCTGCCTGCAACTCAATCCT

CGGACTTTTCTGCCTGAGCAGAACCAGGACATGCCCCCCACCTGCCGACGGCCAGCGCTTCCT

TCCCTGTACACCCCTACTCCTACCAGTCGCCTGGGCTGCCCAGTCCGCCTTACGGTACCATGGA

CAGCTCCCATGTCTTCCACGTTAAGCCTCCGCCGCACGCCTACAGCGCAGCGCTGGAGCCCTTC

TTTGAAAGCCCTCTGACTGATTGCACCAGCCCTTCCTTTGATGGACCCCTCAGCCCGCCGCTCA

GCATCAATGGCAACTTCTCTTTCAAACACGAACCGTCCGCCGAGTTTGAGAAAAATTATGCCTT

TACCATGCACTATCCTGCAGCGACACTGGCAGGGCCCAAAGCCACGGATCAATCTTCTCAGGC

ACCGCTGCCCCTCGCTGCGAGATCCCCATAGACAATATTATGTCCTTCGATAGCCATTCACATC

ATGAGCGAGTCATGAGTGCCCAGCTCAATGCCATATTTCATGATTAG

SEQ ID NO: 2-Human NeuroD1 amino acid sequence-356 amino acids-encoded
by SEQ ID NO: 1
MTKSYSESGLMGEPQPQGPPSWTDECLSSQDEEHEADKKEDDLEAMNAEEDSLRNGGEEEDEDE

DLEEEEEEEEDDDQKPKRRGPKKKKMTKARLERFKLRRMKANARERNRMHGLNAALDNLRKVV

PCYSKTQKLSKIETLRLAKNYIWALSEILRSGKSPDLVSFVQTLCKGLSQPTTNLVAGCLQLNP

RTFLPEQNQDMPPHLPTASASFPVHPYSYQSPGLPSPPYGTMDSSHVFHVKPPPHAYSAALEPF

FESPLTDCTSPSFDGPLSPPLSINGNFSFKHEPSAEFEKNYAFTMHYPAATLAGAQSHGSIFSG

TAAPRCEIPIDNIMSFDSHSHHERVMSAQLNAIFHD

SEQ ID NO: 3-Mouse NeuroD1 nucleic acid sequence encoding mouse NeuroD1
protein-1074 nucleotides, including stop codon
ATGACCAAATCATACAGCGAGAGCGGGCTGATGGGCGAGCCTCAGCCCCAAGGTCCCCCAAGCT

GGACAGATGAGTGTCTCAGTTCTCAGGACGAGGAACACGAGGCAGACAAGAAAGAGGACGAGCT

TGAAGCCATGAATGCAGAGGAGGACTCTCTGAGAAACGGGGGAGAGGAGGAGGAGGAAGATGAG

GATCTAGAGGAAGAGGAGGAAGAAGAAGAGGAGGAGGAGGATCAAAAGCCCAAGAGACGGGGTC

CCAAAAAGAAAAAGATGACCAAGGCGCGCCTAGAACGTTTTAAATTAAGGCGCATGAAGGCCAA

CGCCCGCGAGCGGAACCGCATGCACGGGCTGAACGCGCGCTGGACAACCTGCGCAAGGTGGTA

CCTTGCTACTCCAAGACCCAGAAACTGTCTAAAATAGAGACACTGCGCTTGGCCAAGAACTACA

TCTGGGCTCTGTCAGAGATCCTGCGCTCAGGCAAAAGCCCTGATCTGGTCTCCTTCGTACAGAC
```

-continued

```
GCTCTGCAAAGGTTTGTCCCAGCCCACTACCAATTTGGTCGCCGGCTGCCTGCAGCTCAACCCT

CGGACTTTCTTGCCTGAGCAGAACCCGGACATGCCCCCGCATCTGCCAACCGCCAGCGCTTCCT

TCCCGGTGCATCCCTACTCCTACCAGTCCCCTGGACTGCCCAGCCCGCCCTACGGCACCATGGA

CAGCTCCCACGTCTTCCACGTCAAGCCGCCGCCACACGCCTACAGCGCAGCTCTGGAGCCCTTC

TTTGAAAGCCCCCTAACTGACTGCACCAGCCCTTCCTTTGACGGACCCCTCAGCCCGCCGCTCA

GCATCAATGGCAACTTCTCTTTCAAACACGAACCATCCGCCGAGTTTGAAAAAAATTATGCCTT

TACCATGCACTACCCTGCAGCGACGCTGGCAGGGCCCCAAAGCCACGGATCAATCTTCTCTTCC

GGTGCCGCTGCCCCTCGCTGCGAGATCCCCATAGACAACATTATGTCTTTCGATAGCCATTCGC

ATCATGAGCGAGTCATGAGTGCCCAGCTTAATGCCATCTTTCACGATTAG
```

SEQ ID NO: 4-Mouse NeuroD1 amino acid sequence-357 amino acids-encoded
by SEQ ID NO: 3
```
MTKSYSESGLMGEPQPQGPPSWTDECLSSQDEEHEADKKEDELEAMNAEEDSLRNGGEEEEEDE

DLEEEEEEEEEEEDQKPKRRGPKKKKMTKARLERFKLRRMKANARERNRMHGLNAALDNLRKVV

PCYSKTQKLSKIETLRLAKNYIWALSEILRSGKSPDLVSFVQTLCKGLSQPTTNLVAGCLQLNP

RTFLPEQNPDMPPHLPTASASFPVHPYSYQSPGLPSPPYGTMDSSHVFHVKPPPHAYSAALEPF

FESPLTDCTSPSFDGPLSPPLSINGNFSFKHEPSAEFEKNYAFTMHYPAATLAGPQSHGSIFSS

GAAAPRCEIPTDNIMSFDSHSHHERVMSAQLNAIFHD
```

Mouse LCN2 promoter-SEQ ID NO: 5
```
GCAGTGTGGAGACACACCCACTTTCCCCAAGGGCTCCTGCTCCCCCAAGTGATCCCCTTATCCT

CCGTGCTAAGATGACACCGAGGTTGCAGTCCTTACCTTTGAAAGCAGCCACAAGGGCGTGGGGG

TGCACACCTTTAATCCCAGCACTCGGGAGGCAGAGGCAGGCAGATTTCTGAGTTCGAGACCAGC

CTGGTCTACAAAGTGAATTCCAGGACAGCCAGGGCTATACAGAGAAACCCTGTCTTGAAAAAA

AAGAGAAAGAAAATAGAAAAAAAAAAATGAAAGCAGCCACATCTAAGGACTACGTGGCACAGGA

GAGGGTGAGTCCCTGAGAGTTCAGCTGCTGCCCTGTCTGTTCCTGTAAATGGCAGTGGGGTCAT

GGGAAAGTGAAGGGGCTCAAGGTATTGGACACTTCCAGGATAATCTTTTGGACGCCTCACCCTG

TGCCAGGACCAAGGCTGAGCTTGGCAGGCTCAGAACAGGGTGTCCTGTTCTTCCCTGTCTAAAA

CATTCACTCTCAGCTTGCTCACCCTTCCCCAGACAAGGAAGCTGCACAGGGTCTGGTGTTCAGA

TGGCTTTGGCTTACAGCAGGTGTGGGTGTGGGGTAGGAGGCAGGGGTAGGGTGGGGAAGCC

TGTACTATACTCACTATCCTGTTTCTGACCCTCTAGGACTCCTACAGGGTTATGGGAGTGGACA

GGCAGTCCAGATCTGAGCTGCTGACCCACAAGCAGTGCCCTGTGCCTGCCAGAATCCAAAGCCC

TGGGAATGTCCCTCTGGTCCCCCTCTGTCCCCTGCAGCCCTTCCTGTTGCTCAACCTTGCACAG

TTCCGACCTGGGGGAGAGAGGGACAGAAATCTTGCCAAGTATTTCAACAGAATGTACTGGCAAT

TACTTCATGGCTTCCTGGACTTGGTAAAGGATGGACTACCCCGCCCAACAGGGGGCTGGCAGC

CAGGTAGGCCCATAAAAAGCCCGCTGGGGAGTCCTCCTCACTCTCTGCTCTTCCTCCTCCAGCA

CACATCAGACCTAGTAGCTGTGGAAACCA
```

Human GFAP promoter-SEQ ID NO: 6
```
GTCTGCAAGCAGAGACCTGGCAGCATTGGGCTGGCCGCCCCCCAGGGCCTCCTCTTCATGCCCAGT

GAATGACTCACCTTGGCACAGACACAATGTTCGGGGTGGGCACAGTGCCTGCTTCCCGCCGCAC

CCCAGCCCCCCTCAAATGCCTTCCGAGAAGCCCATTGAGTAGGGGGCTTGCATTGCACCCCAGC

CTGACAGCCTGGCATCTTGGGATAAAAGCAGCACAGCCCCCTAGGGGCTGCCCTTGCTGTGTGG

CGCCACCGGCGGTGGAGAACAAGGCTCTATTCAGCCTGTGCCCAGGAAAGGGGATCAGGGGATG

CCCAGGCATGGACAGTGGGTGGCAGGGGGGAGAGGAGGGCTGTCTGCTTCCCAGAAGTCCAAG

GACACAAATGGGTGAGGGGACTGGGCAGGGTTCTGACCCTGTGGGACCAGAGTGGAGGGCGTAG
```

```
ATGGACCTGAAGTCTCCAGGGACAACAGGGCCCAGGTCTCAGGCTCCTAGTTGGGCCCAGTGGC

TCCAGCGTTTCCAAACCCATCCATCCCCAGAGGTTCTTCCCATCTCTCCAGGCTGATGTGTGGG

AACTCGAGGAAATAAATCTCCAGTGGGAGACGGAGGGGTGGCCAGGGAAACGGGGCGCTGCAGG

AATAAAGACGAGCCAGCACAGCCAGCTCATGCGTAACGGCTTTGTGGAGCTGTCAAGGCCTGGT

CTCTGGGAGAGAGGCACAGGGAGGCCAGACAAGGAAGGGGTGACCTGGAGGGACAGATCCAGGG

GCTAAAGTCCTGATAAGGCAAGAGAGTGCCGGCCCCTCTTGCCCTATCAGGACCTCCACTGCC

ACATAGAGGCCATGATTGACCCTTAGACAAAGGGCTGGTGTCCAATCCCAGCCCCAGCCCCAG

AACTCCAGGGAATGAATGGGCAGAGAGCAGGAATGTGGGACATCTGTGTTCAAGGGAAGGACTC

CAGGAGTCTGCTGGGAATGAGGCCTAGTAGGAAATGAGGTGGCCCTTGAGGGTACAGAACAGGT

TCATTCTTCGCCAAATTCCCAGCACCTTGCAGGCACTTACAGCTGAGTGAGATAATGCCTGGGT

TATGAAATCAAAAAGTTGGAAAGCAGGTCAGAGGTCATCTGGTACAGCCCTTCCTTCCCTTTTT

TTTTTTTTTTTTTGTGAGACAAGGTCTCTCTCTGTTGCCCAGGCTGGAGTGGCGCAAACACAG

CTCACTGCAGCCTCAACCTACTGGGCTCAAGCAATCCTCCAGCCTCAGCCTCCCAAAGTGCTGG

GATTACAAGCATGAGCCACCCCACTCAGCCCTTTCCTTCCTTTTAATTGATGCATAATAATTG

TAAGTATTCATCATGGTCCAACCAACCCTTTCTTGACCCACCTTCCTAGAGAGAGGGTCCTCTT

GATTCAGCGGTCAGGGCCCAGACCCATGGTCTGGCTCCAGGTACCACCTGCCTCATGCAGGAG

TTGGCGTGCCCAGGAAGCTCTGCCTCTGGGCACAGTGACCTCAGTGGGGTGAGGGGAGCTCTCC

CCATAGCTGGGCTGCGGCCCAACCCCACCCCCTCAGGCTATGCCAGGGGGTGTTGCCAGGGGCA

CCCGGGCATCGCCAGTCTAGCCCACTCCTTCATAAAGCCCTCGCATCCCAGGAGCGAGCAGAGC

CAGAGCAT

Mouse Aldh1L1 promoter-SEQ ID NO: 7
AACTGAGAGTGGAGGGGCACAGAAGAGCCCAAGAGGCTCCTTAGGTTGTGTGGAGGGTACAATA

TGTTTGGGCTGAGCAACCCAGAGCCAGACTTTGTCTGGCTGGTAAGAGACAGAGGTGCCTGCTA

TCACAATCCAAGGGTCTGCTTGAGGCAGAGCCAGTGCAAAGGATGTGGTTAGAGCCAGCCTGGT

GTACTGAAGAGGGGCGAAGAGCTTGAGTAAGGAGTCTCAGCGGTGGTTTGAGAGGCAGGGTGGT

TAATGGAGTAGCTGCAGGGGAGAATCCTTGGGAGGGAGCCTGCAGGACAGAGCTTTGGTCAGGA

AGTGATGGGCATGTCACTGGACCCTGTATTGTCTCTGACTTTTCTCAAGTAGGACAATGACTCT

GCCCAGGGAGGGGTCTGTGACAAGGTGGAAGGGCCAGAGGAGAACTTCTGAGAAGAAAACCAG

AGGCCGTGAAGAGGTGGGAAGGGCATGGGATTCAGAACCTCAGGCCCACCAGGACACAACCCCA

GGTCCACAGCAGATGGGTGACCTTGCATGTCTCAGTCACCAGCATTGTGCTCCTTGCTTATCAC

GCTTGGGTGAAGGAAATGACCCAAATAGCATAAAGCCTGAAGGCCGGGACTAGGCCAGCTAGGG

CTTGCCCTTCCCTTCCCAGCTGCACTTTCCATAGGTCCCACCTTCAGCAGATTAGACCCGCCTC

CTGCTTCCTGCCTCCTTGCCTCCTCACTCATGGGTCTATGCCCACCTCCAGTCTCGGGACTGAG

GCTCACTGAAGTCCCATCGAGGTCTGGTCTGGTGAATCAGCGGCTGGCTCTGGGCCCTGGGCGA

CCAGTTAGGTTCCGGGCATGCTAGGCAATGAACTCTACCCGGAATTGGGGGTGCGGGGAGGCGG

GGAGGTCTCCAACCCAGCCTTTTGAGGACGTGCCTGTCGCTGCACGGTGCTTTTTATAGACGAT

GGTGGCCCATTTTGCAGAAGGGAAAGCCGGAGCCCTCTGGGGAGCAAGGTCCCCGCAAATGGAC

GGATGACCTGAGCTTGGTTCTGCCAGTCCACTTCCCAAATCCCTCACCCCATTCTAGGGACTAG

GGAAAGATCTCCTGATTGGTCATATCTGGGGGCCTGGCCGGAGGGCCTCCTATGATTGGAGAGA

TCTAGGCTGGGCGGCCCTAGAGCCCGCCTCTTCTCTGCCTGGAGGAGGAGCACTGACCCCTAAC

CCTCTCTGCACAAGACCCGAGCTTGTGCGCCCTTCTGGGAGCTTGCTGCCCCTGTGCTGACTGC
```

-continued

TGACAGCTGACTGACGCTCGCAGCTAGCAGGTACTTCTGGGTTGCTAGCCCAGAGCCCTGGGCC

GGTGACCCTGTTTTCCCTACTTCCCGTCTTTGACCTTGGGTAAGTTTCTTTTTCTTTTGTTTTT

GAGAGAGGCACCCAGATCCTCTCCACTACAGGCAGCCGCTGAACCTTGGATCCTCAGCTCCTGC

CCTGGGAACTACAGTTCCTGCCCTTTTTTCCCACCTTGAGGGAGGTTTTCCCTGAGTAGCTTC

GACTATCCTGGAACAAGCTTTGTAGACCAGCCTGGGTCTCCGGAGAGTTGGGATTAAAGGCGTG

CACCACCACC

Human NG2 promoter-SEQ ID NO: 8
CTCTGGTTTCAAGACCAATACTCATAACCCCCACATGGACCAGGCACCATCACACCTGAGCACT

GCACTTAGGGTCAAAGACCTGGCCCCACATCTCAGCAGCTATGTAGACTAGCTCCAGTCCCTTA

ATCTCTCTCAGCCTCAGTTTCTTCATCTGCAAAACAGGTCTCAGTTTCGTTGCAAAGTATGAAG

TGCTGGGCTGTTACTGGTCAAAGGGAAGAGCTGGGAAGAGGGTGCAAGGTGGGGTTGGGCTGGA

GATGGGCTGGAGCAGATAGATGGAGGGACCTGAATGGAGGAAGTAAACCAAGGCCCGGTAACAT

TGGGACTGGACAGAGAACACGCAGATCCTCTAGGCACCGGAAGCTAAGTAACATTGCCCTTTCT

CCTCCTGTTTGGGACTAGGCTGATGTTGCTGCCTGGAAGGGAGCCAGCAGAAGGGCCCCAGCCT

GAAGCTGTTAGGTAGAAGCCAAATCCAGGGCCAGATTTCCAGGAGGCAGCCTCGGGAAGTTGAA

ACACCCGGATTCAGGGGTCAGGAGGCCTGGGCTTCTGGCACCAAACGGCCAGGGACCTACTTTC

CACCTGGAGTCTTGTAAGAGCCACTTTCAGCTTGAGCTGCACTTTCGTCCTCCATGAAATGGGG

GAGGGGATGCTCCTCACCCACCTTGCAAGGTTATTTTGAGGCAAATGTCATGGCGGGACTGAGA

ATTCTTCTGCCCTGCGAGGAAATCCAGACATCTCTCCCTTACAGACAGGGAGACTGAGGTGAGG

CCCTTCCAGGCAGAGAAGGTCACTGTTGCAGCCATGGGCAGTGCCCCACAGGACCTCGGGTGGT

GCCTCTGGAGTCTGGAGAAGTTCCTAGGGGACCTCCGAGGCAAAGCAGCCCAAAAGCCGCCTGT

GAGGGTGGCTGGTGTCTGTCCTTCCTCCTAAGGCTGGAGTGTGCCTGTGGAGGGGTCTCCTGAA

CTCCCGCAAAGGCAGAAAGGAGGGAAGTAGGGGCTGGGACAGTTCATGCCTCCTCCCTGAGGGG

GTCTCCCGGGCTCGGCTCTTGGGGCCAGAGTTCAGGGTGTCTGGGCCTCTCTATGACTTTGTTC

TAAGTCTTTAGGGTGGGGCTGGGGTCTGGCCCAGCTGCAAGGGCCCCCTCACCCCTGCCCCAGA

GAGGAACAGCCCCGCACGGGCCCTTTAAGAAGGTTGAGGGTGGGGCAGGTGGGGGAGTCCAAG

CCTGAAACCCGAGCGGGCGCGCGGGTCTGCGCCTGCCCCGCCCCCGGAGTTAAGTGCGCGGACA

CCCGGAGCCGGCCCGCGCCCAGGAGCAGAGCCGCGCTCGCTCCACTCAGCTCCCAGCTCCCAGG

ACTCCGCTGGCTCCTCGCAAGTCCTGCCGCCCAGCCCGCCGGG

CAG::NeuroD1-IRES-GFP-SEQ ID NO: 9
GATCCGGCCATTAGCCATATTATTCATTGGTTATATAGCATAAATCAATATTGGCTATTGGCCA

TTGCATACGTTGTATCCATATCATAATATGTACATTTATATTGGCTCATGTCCAACATTACCGC

CATGTTGACATTGATTATTGACTAGTTATTAATAGTAATCAATTACGGGGTCATTAGTTCATAG

CCCATATATGGAGTTCCGCGTTACATAACTTACGGTAAATGGCCCGCCTGGCTGACCGCCCAAC

GACCCCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGTATCA

TATGCCAAGTACGCCCCCTATTGACGTCAATGACGGTAAATGGCCCGCCTGGCATTATGCCCAG

TACATGACCTTATGGGACTTTCCTACTTGGCAGTACATCTACGTATTAGTCATCGCTATTACCA

TGGTGATGCGGTTTTGGCAGTACATCAATGGGCGTGGATAGCGGTTTGACTCACGGGGATTTCC

AAGTCTCCACCCCATTGACGTCAATGGGAGTTTGTTTTGGCACCAAAATCAACGGGACTTTCCA

AAATGTCGTAACAACTCCGCCCCATTGACGCAAATGGGCGGTAGGCATGTACGGTGGGAGGTCT

-continued

```
ATATAAGCAGAGCTCAATAAAAGAGCCCACAACCCCTCACTCGGGGCGCCAGTCCTCCGATTGA

CTGAGTCGCCCGGGTACCCGTATTCCCAATAAAGCCTCTTGCTGTTTGCATCCGAATCGTGGTC

TCGCTGTTCCTTGGGAGGGTCTCCTCTGAGTGATTGACTACCCACGACGGGGGTCTTTCATTTG

GGGGCTCGTCCGGGATTTGGAGACCCCTGCCCAGGGACCACCGACCCACCACCGGGAGGTAAGC

TGGCCAGCAACTTATCTGTGTCTGTCCGATTGTCTAGTGTCTATGTTTGATGTTATGCGCCTGC

GTCTGTACTAGTTAGCTAACTAGCTCTGTATCTGGCGGACCCGTGGTGGAACTGACGAGTTCTG

AACACCCGGCCGCAACCCTGGGAGACGTCCCAGGGACTTTGGGGGCCGTTTTTGTGGCCCGACC

TGAGGAAGGGAGTCGATGTGGAATCCGACCCCGTCAGGATATGTGGTTCTGGTAGGAGACGAGA

ACCTAAAACAGTTCCCGCCTCCGTCTGAATTTTTGCTTTCGGTTTGGAACCGAAGCCGCGCGTC

TTGTCTGCTGCAGCGCTGCAGCATCGTTCTGTGTTGTCTCTGTCTGACTGTGTTTCTGTATTTG

TCTGAAAATTAGGGCCAGACTGTTACCACTCCCTTAAGTTTGACCTTAGGTCACTGGAAAGATG

TCGAGCGGATCGCTCACAACCAGTCGGTAGATGTCAAGAAGAGACGTTGGGTTACCTTCTGCTC

TGCAGAATGGCCAACCTTTAACGTCGGATGGCCGCGAGACGGCACCTTTAACCGAGACCTCATC

ACCCAGGTTAAGATCAAGGTCTTTTCACCTGGCCCGCATGGACACCCAGACCAGGTCCCCTACA

TCGTGACCTGGGAAGCCTTGGCTTTTGACCCCCCTCCCTGGGTCAAGCCCTTTGTACACCCTAA

GCCTCCGCCTCCTCTTCCTCCATCCGCCCCGTCTCTCCCCCTTGAACCTCCTCGTTCGACCCCG

CCTCGATCCTCCCTTTATCCAGCCCTCACTCCTTCTCTAGGCGCCGGAATTCGATGTCGACATT

GATTATTGACTAGTTATTAATAGTAATCAATTACGGGGTCATTAGTTCATAGCCCATATATGGA

GTTCCGCGTTACATAACTTACGGTAAATGGCCCGCCTGGCTGACCGCCCAACGACCCCCGCCCA

TTGACGTCAATAATGACGTATGTTCCCATAGTAACGCCAATAGGGACTTTCCATTGACGTCAAT

GGGTGGACTATTTACGGTAAACTGCCCACTTGGCAGTACATCAAGTGTATCATATGCCAAGTAC

GCCCCCTATTGACGTCAATGACGGTAAATGGCCCGCCTGGCATTATGCCCAGTACATGACCTTA

TGGGACTTTCCTACTTGGCAGTACATCTACGTATTAGTCATCGCTATTACCATGGGTCGAGGTG

AGCCCCACGTTCTGCTTCACTCTCCCCATCTCCCCCCCCTCCCACCCCCAATTTTGTATTTAT

TTATTTTTTAATTATTTTGTGCAGCGATGGGGGCGGGGGGGGGGGGCGCGCGCCAGGCGGGG

CGGGGCGGGGCGAGGGCGGGGCGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAAAGCGAAGC

GCGCGGCGGGCGGGAGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGGGACGGCCCTTCTCC

TCCGGGCTGTAATTAGCGCTTGGTTTAATGACGGCTCGTTTCTTTTCTGTGGCTGCGTGAAAGC

CTTAAAGGGCTCCGGGAGGGCCCTTTGTGCGGGGGGAGCGGCTCGGGGGTGCGTGCGTGTGT

GTGTGCGTGGGGAGCGCCGCGTGCGGCCCGCGCTGCCCGGCGGCTGTGAGCGCTGCGGGCGCGG

CGCGGGGCTTTGTGCGCTCCGCGTGTGCGCGAGGGGAGCGCGGCCGGGGCGGTGCCCCGCGGT

GCGGGGGGCTGCGAGGGGAACAAAGGCTGCGTGCGGGTGTGTGCGTGGGGGGTGAGCAGGG

GGTGTGGGCGCGGCGGTCGGGCTGTAACCCCCCCTGCACCCCCCTCCCCGAGTTGCTGAGCAC

GGCCCGGCTTCGGGTGCGGGGCTCCGTGCGGGGCGTGGCGCGGGGCTCGCCGTGCCGGGCGGGG

GGTGGCGGCAGGTGGGGGTGCCGGGCGGGGCGGGGCCGCCTCGGGCCGGGGAGGGCTCGGGGGA

GGGGCGCGGCGGCCCCGGAGCGCCGGCGGCTGTCGAGGCGCGGCGAGCCGCAGCCATTGCCTTT

TATGGTAATCGTGCGAGAGGGCGCAGGGACTTCCTTTGTCCCAAATCTGGCGGAGCCGAAATCT

GGGAGGCGCCGCCGCACCCCCTCTAGCGGGCGCGGGCGAAGCGGTGCGGCGCCGGCAGGAAGGA

AATGGGCGGGAGGGCCTTCGTGCGTCGCCGCGCCGCCGTCCCCTTCTCCATCTCCAGCCTCGG
```

-continued

```
GGCTGCCGCAGGGGGACGGCTGCCTTCGGGGGGGACGGGGCAGGGCGGGGTTCGGCTTCTGGCG
TGTGACCGGCGGCTCTAGAGCCTCTGCTAACCATGTTCATGCCTTCTTCTTTTTCCTACAGCTC
CTGGGCAACGTGCTGGTTGTTGTGCTGTCTCATCATTTTGGCAAAGAATTCGCTAGCGGATCCG
GCCGCCTCGGCCACCGGTCGCCACCATCGCCACCATGACCAAATCATACAGCGAGAGCGGGCTG
ATGGGCGAGCCTCAGCCCCAAGGTCCCCCAAGCTGGACAGATGAGTGTCTCAGTTCTCAGGACG
AGGAACACGAGGCAGACAAGAAAGAGGACGAGCTTGAAGCCATGAATGCAGAGGAGGACTCTCT
GAGAAACGGGGGAGAGGAGGAGGAGGAAGATGAGGATCTAGAGGAAGAGGAGGAAGAAGAAGAG
GAGGAGGAGGATCAAAAGCCCAAGAGACGGGGTCCCAAAAAGAAAAAGATGACCAAGGCGCGCC
TAGAACGTTTTAAATTAAGGCGCATGAAGGCCAACGCCCGCGAGCGGAACCGCATGCACGGGCT
GAACGCGGCGCTGGACAACCTGCGCAAGGTGGTACCTTGCTACTCCAAGACCCAGAAACTGTCT
AAAATAGAGACACTGCGCTTGGCCAAGAACTACATCTGGGCTCTGTCAGAGATCCTGCGCTCAG
GCAAAAGCCCTGATCTGGTCTCCTTCGTACAGACGCTCTGCAAAGGTTTGTCCCAGCCCACTAC
CAATTTGGTCGCCGGCTGCCTGCAGCTCAACCCTCGGACTTTCTTGCCTGAGCAGAACCCGGAC
ATGCCCCGCATCTGCCAACCGCCAGCGCTTCCTTCCCGGTGCATCCCTACTCCTACCAGTCCC
CTGGACTGCCCAGCCCGCCCTACGGCACCATGGACAGCTCCCACGTCTTCCACGTCAAGCCGCC
GCCACACGCCTACAGCGCAGCTCTGGAGCCCTTCTTTGAAAGCCCCCTAACTGACTGCACCAGC
CCTTCCTTTGACGGACCCCTCAGCCCGCCGCTCAGCATCAATGGCAACTTCTCTTTCAAACACG
AACCATCCGCCGAGTTTGAAAAAAATTATGCCTTTACCATGCACTACCCTGCAGCGACGCTGGC
AGGGCCCCAAAGCCACGGATCAATCTTCTCTTCCGGTGCCGCTGCCCCTCGCTGCGAGATCCCC
ATAGACAACATTATGTCTTTCGATAGCCATTCGCATCATGAGCGAGTCATGAGTGCCCAGCTTA
ATGCCATCTTTCACGATTAGGTTTAAACGCGGCCGCGCCCCTCTCCCTCCCCCCCCCCTAACGT
TACTGGCCGAAGCCGCTTGGAATAAGGCCGGTGTGCGTTTGTCTATATGTTATTTTCCACCATA
TTGCCGTCTTTTGGCAATGTGAGGGCCCGGAAACCTGGCCCTGTCTTCTTGACGAGCATTCCTA
GGGGTCTTTCCCCTCTCGCCAAAGGAATGCAAGGTCTGTTGAATGTCGTGAAGGAAGCAGTTCC
TCTGGAAGCTTCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCAAAGGCGGCAC
AACCCCAGTGCCACGTTGTGAGTTGGATAGTTGTGGAAAGAGTCAAATGGCTCTCCTCAAGCGT
ATTCAACAAGGGGCTGAAGGATGCCCAGAAGGTACCCCATTGTATGGGATCTGATCTGGGGCCT
CGGTGCACATGCTTTACATGTGTTTAGTCGAGGTTAAAAAAACGTCTAGGCCCCCCGAACCACG
GGGACGTGGTTTTCCTTTGAAAAACACGATGATAATATGGCCACAACCATGGTGAGCAAGGGCG
AGGAGCTGTTCACCGGGGTGGTGCCCATCCTGGTCGAGCTGGACGGCGACGTAAACGGCCACAA
GTTCAGCGTGTCCGGCGAGGGCGAGGGCGATGCCACCTACGGCAAGCTGACCCTGAAGTTCATC
TGCACCACCGGCAAGCTGCCCGTGCCCTGGCCCACCCTCGTGACCACCCTGACCTACGGCGTGC
AGTGCTTCAGCCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGACCCGCGCCGAG
GTGAAGTTCGAGGGCGACACCCTGGTGAACCGCATCGAGCTGAAGGGCATCGACTTCAAGGAGG
ACGGCAACATCCTGGGGCACAAGCTGGAGTACAACTACAACAGCCACAACGTCTATATCATGGC
CGACAAGCAGAAGAACGGCATCAAGGTGAACTTCAAGATCCGCCACAACATCGAGGACGGCAGC
GTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACAT
```

-continued

```
GGTCCTGCTGGAGTTCGTGACCGCCGCCGGGATCACTCTCGGCATGGACGAGCTGTACAAGTAA

GTCGACAATCAACCTCTGGATTACAAAATTTGTGAAAGATTGACTGGTATTCTTAACTATGTTG

CTCCTTTTACGCTATGTGGATACGCTGCTTTAATGCCTTTGTATCATGCTATTGCTTCCCGTAT

GGCTTTCATTTTCTCCTCCTTGTATAAATCCTGGTTGCTGTCTCTTTATGAGGAGTTGTGGCCC

GTTGTCAGGCAACGTGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCTATTGCCACGGCGGA

ACTCATCGCCGCCTGCCTTGCCCGCTGCTGGACAGGGGCTCGGCTGTTGGGCACTGACAATTCC

GTGGTGTTGTCGGGGAAGCTGACGTCCTTTCCATGGCTGCTCGCCTGTGTTGCCACCTGGATTC

TGCGCGGGACGTCCTTCTGCTACGTCCCTTCGGCCCTCAATCCAGCGGACCTTCCTTCCCGCGG

CCTGCTGCCGGCTCTGCGGCCTCTTCCGCGTCTTCGCCTTCGCCCTCAGACGAGTCGGATCTCC

CTTTGGGCCGCCTCCCCGCCTGGAATTCGAGCTCGAGCTTGTTAACATCGATAAAATAAAAGAT

TTTATTTAGTCTCCAGAAAAAGGGGGGAATGAAAGACCCCACCTGTAGGTTTGGCAAGCTAGCT

TAAGTAACGCCATTTTGCAAGGCATGGAAAAATACATAACTGAGAATAGAGAAGTTCAGATCAA

GGTCAGGAACAGATGGAACAGCTGAATATGGGCCAAACAGGATATCTGTGGTAAGCAGTTCCTG

CCCCGGCTCAGGGCCAAGAACAGATGGAACAGCTGAATATGGGCCAAACAGGATATCTGTGGTA

AGCAGTTCCTGCCCCGGCTCAGGGCCAAGAACAGATGGTCCCCAGATGCGGTCCAGCCCTCAGC

AGTTTCTAGAGAACCATCAGATGTTTCCAGGGTGCCCCAAGGACCTGAAATGACCCTGTGCCTT

ATTTGAACTAACCAATCAGTTCGCTTCTCGCTTCTGTTCGCGCGCTTCTGCTCCCCGAGCTCAA

TAAAAGAGCCCACAACCCCTCACTCGGGGCGCCAGTCCTCCGATTGACTGAGTCGCCCGGGTAC

CCGTGTATCCAATAAACCCTCTTGCAGTTGCATCCGACTTGTGGTCTCGCTGTTCCTTGGGAGG

GTCTCCTCTGAGTGATTGACTACCCGTCAGCGGGGGTCTTTCATTTCCGACTTGTGGTCTCGCT

GCCTTGGGAGGGTCTCCTCTGAGTGATTGACTACCCGTCAGCGGGGTCTTCACATGCAGCATG

TATCAAAATTAATTTGGTTTTTTTTCTTAAGTATTTACATTAAATGGCCATAGTTGCATTAATG

AATCGGCCAACGCGCGGGGAGAGGCGGTTTGCGTATTGGCGCTCTTCCGCTTCCTCGCTCACTG

ACTCGCTGCGCTCGGTCGTTCGGCTGCGGCGAGCGGTATCAGCTCACTCAAAGGCGGTAATACG

GTTATCCACAGAATCAGGGGATAACGCAGGAAAGAACATGTGAGCAAAAGGCCAGCAAAAGGCC

AGGAACCGTAAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGATACCAGGCGTT

TCCCCCTGGAAGCTCCCTCGTGCGCTCTCCTGTTCCGACCCTGCCGCTTACCGGATACCTGTCC

GCCTTTCTCCCTTCGGGAAGCGTGGCGCTTTCTCATAGCTCACGCTGTAGGTATCTCAGTTCGG

TGTAGGTCGTTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCACTGGCAGCA

GCCACTGGTAACAGGATTAGCAGAGCGAGGTATGTAGGCGGTGCTACAGAGTTCTTGAAGTGGT

GGCCTAACTACGGCTACACTAGAAGGACAGTATTTGGTATCTGCGCTCTGCTGAAGCCAGTTAC

CTTCGGAAAAAGAGTTGGTAGCTCTTGATCCGGCAAACAAACCACCGCTGGTAGCGGTGGTTTT

TTTGTTTGCAAGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCATGAGATTATC

AAAAAGGATCTTCACCTAGATCCTTTTAAATTAAAAATGAAGTTTGCGGCCGGCCGCAAATCAA

TCTAAAGTATATATGAGTAAACTTGGTCTGACAGTTACCAATGCTTAATCAGTGAGGCACCTAT

CTCAGCGATCTGTCTATTTCGTTCATCCATAGTTGCCTGACTCCCCGTCGTGTAGATAACTACG

ATACGGGAGGGCTTACCATCTGGCCCCAGTGCTGCAATGATACCGCGAGACCCACGCTCACCGG
```

-continued

```
CTCCAGATTTATCAGCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACGCTCGTCGTTTGGTA

TGGCTTCATTCAGCTCCGGTTCCCAACGATCAAGGCGAGTTACATGATCCCCCATGTTGTGCAA

AAAAGCGGTTAGCTCCTTCGGTCCTCCGATCGTTGTCAGAAGTAAGTTGGCCGCAGTGTTATCA

CTCATGGTTATGGCAGCACTGCATAATTCTCTTACTGTCATGCCATCCGTAAGATGCTTTTCTG

TGACTGGTGAGTACTCAACCAAGTCATTCTGAGAATAGTGTATGCGGCGACCGAGTTGCTCTTG

CCCGGCGTCAACACGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTTCGATGTAAC

CCACTCGTGCACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTTGAATACTCATA

CTCTTCCTTTTTCAAT
```

Items

Item 1. A method of producing a neuronal phenotype in a glial cell, comprising: expressing exogenous NeuroD1 in the glial cell, wherein the glial cell is selected from the group consisting of: an astrocyte, a reactive astrocyte, an NG2 cell and a reactive NG2 cell.

Item 2. The method of item 1, wherein the glial cell is in vitro.

Item 3. The method of item 1, wherein the glial cell is in vivo.

Item 4. The method of any of items 1-3, wherein the glial cell is a human glial cell.

Item 5. The method of any of items 1-4, wherein the glial cell is a non-human mammalian glial cell.

Item 6. The method of any of items 1-5, wherein expressing exogenous NeuroD1 comprises delivering an expression vector comprising a nucleic acid encoding NeuroD1 to the glial cell.

Item 7. The method of any of items 1-6, wherein expressing exogenous NeuroD1 comprises delivering a viral expression vector comprising a nucleic acid encoding NeuroD1 to the glial cell.

Item 8. The method of any of items 1-7, wherein expressing exogenous NeuroD1 comprises delivering a retrovirus expression vector comprising a nucleic acid encoding NeuroD1 to the glial cell.

Item 9. The method of any of items 1-8, wherein the neuronal phenotype comprises one or more of: neuronal morphology, expression of one or more neuronal markers, electrophysiologic characteristics of neurons, synapse formation and release of neurotransmitter.

Item 10. The method of any of items 1-9, wherein NeuroD1 is the only exogenously expressed transcription factor in the glial cell.

Item 11. An in vitro glial cell comprising exogenous NeuroD1.

Item 12. An in vitro glial cell comprising an expression vector encoding NeuroD1.

Item 13. The in vitro glial cell of item 11 or 12, having a neuronal phenotype, wherein the neuronal phenotype comprises one or more of: neuronal morphology, expression of one or more neuronal markers, electrophysiologic characteristics of neurons, synapse formation and release of neurotransmitter.

Item 14. The in vitro glial cell of any of items 11-13, wherein NeuroD1 is the only exogenously expressed transcription factor in the glial cell.

Item 15. An in vitro glial cell substantially as described herein.

Item 16. A method of producing a neuronal phenotype in a glial cell substantially as described herein.

Item 17. A method of treating a neurological condition in a subject in need thereof, comprising: administering a therapeutically effective dose of NeuroD1 to a glial cell of the subject; whereby exogenous NeuroD1 is expressed in the glial cell, producing a neuronal phenotype in the glial cell to ameliorate the neurological condition of the subject.

Item 18. The method of treating a neurological condition in a subject in need thereof, according to item 17, wherein administering the therapeutically effective dose of NeuroD1 comprises administering an expression vector comprising a nucleic acid sequence encoding NeuroD1 protein.

Item 19. The method of treating a neurological condition in a subject in need thereof, according to item 18, wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof.

Item 20. The method of treating a neurological condition in a subject in need thereof, according to any of items 17-19, wherein the neurological condition is characterized by presence of reactive astrocytes.

Item 21. The method of treating a neurological condition in a subject in need thereof, according to any of items 17-20, wherein the neurological condition is an injury to the central or peripheral nervous system.

Item 22. The method of treating a neurological condition in a subject in need thereof, according to any of items 17-21, wherein the neurological condition is selected from the group consisting of: Alzheimer disease, Parkinson disease, amyotrophic lateral sclerosis (ALS), epilepsy and stroke.

Item 23. The method of treating a neurological condition in a subject in need thereof; according to any of items 17-22, wherein administering a therapeutically effective dose of NeuroD1 comprises local administration.

Item 24. The method of treating a neurological condition in a subject in need thereof; according to any of items 17-23, wherein administering a therapeutically effective dose of NeuroD1 comprises systemic administration.

Item 25. The method of treating a neurological condition in a subject in need thereof; according to any of items 17-24, wherein administering the therapeutically effective dose of NeuroD1 comprises administering an expression vector comprising a nucleic acid sequence encoding NeuroD1 protein, the nucleic acid sequence operably linked to a ubiquitous promoter.

Item 26. The method of treating a neurological condition in a subject in need thereof, according to any of items 17-25, wherein administering the therapeutically effective dose of NeuroD1 comprises administering an expression vector comprising a nucleic acid sequence encoding NeuroD1 protein, the nucleic acid sequence operably linked to a cell type-specific promoter selected from the group consisting of: an astrocyte-specific promoter and an NG2 cell-specific promoter.

Item 27. The method of treating a neurological condition in a subject in need thereof, according to any of items 17-26, wherein the expression vector is a viral expression vector.

Item 28. The method of treating a neurological condition in a subject in need thereof, according to any of items 17-27, wherein the expression vector is a retrovirus.

Item 29. The method of treating a neurological condition in a subject in need thereof, according to any of items 17-28, wherein the expression vector is an adenovirus.

Item 30. The method of treating a neurological condition in a subject in need thereof, according to any of items 17-28, wherein the expression vector is an adeno-associated virus.

Item 31. The method of treating a neurological condition in a subject in need thereof, according to any of items 17-28, wherein the expression vector is a lentivirus.

Item 32. The method of treating a neurological condition in a subject in need thereof, according to any of items 17-24, wherein administering the therapeutically effective dose of NeuroD1 comprises administering NeuroD1 protein.

Item 33. The method of treating a neurological condition in a subject in need thereof, according to any of items 17-24, wherein administering the therapeutically effective dose of NeuroD1 comprises administering mRNA encoding NeuroD1 protein.

Item 34. A method of treating a neurological condition in a subject in need thereof, comprising: providing a viral expression vector comprising a nucleic acid encoding NeuroD1; and delivering the viral expression vector to the central nervous system or peripheral nervous system of the subject, whereby the viral vector infects dividing cells of the central nervous system or peripheral nervous system, respectively, producing infected cells and whereby exogenous NeuroD1 is expressed in the infected cells at a therapeutically effective level, wherein the expression of NeuroD1 in the infected cells results in a greater number of neurons in the subject compared to an untreated subject having the same neurological condition, whereby the neurological condition is treated.

Item 35. The method of any of items 17-34, wherein NeuroD1 is the only exogenously expressed transcription factor in the glial cell.

Item 36. A method of treating a neurological condition in a subject in need thereof substantially as described herein.

Item 37. An expression vector, comprising a glial cell specific promoter operably linked to a nucleic acid encoding NeuroD1.

Item 38. The expression vector of item 37 wherein the glial cell specific promoter is an astrocyte specific promoter or an NG2 cell specific promoter.

Item 39. The expression vector of item 37 or 38 wherein the expression vector is a viral vector.

Item 40. The expression vector of any of items 37-39 wherein the expression vector is a retroviral expression vector.

Item 41. The expression vector of any of items 37-40 wherein the expression vector is an adenovirus, adeno-associated virus or lentivirus.

Item 42. The expression vector of any of items 37-41 wherein the promoter is a GFAP promoter, NG2 promoter, Aldh1L1 promoter or LCN2 promoter.

Item 43. The expression vector of any of items 37-41 wherein the nucleic acid sequence encoding NeuroD1 protein comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4, or a functional fragment thereof.

Item 44. An expression vector, comprising a glial cell specific promoter operably linked to a nucleic acid encoding NeuroD1 substantially as described herein.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a neurological condition in a subject in need thereof, wherein the neurological condition is characterized by loss of neurons and presence of reactive NG2 cells, comprising:

administering a therapeutically effective dose of NeuroD1 transcription factor to a NG2 cell of the subject, wherein administering the therapeutically effective dose of NeuroD1 transcription factor comprises administering an expression vector comprising a nucleic acid sequence encoding NeuroD1 transcription factor, wherein no transcription factor other than NeuroD1 is required to be exogenously expressed in the reactive NG2 cell, thereby producing a neuronal phenotype in the NG2 cell to ameliorate the neurological condition of the subject.

2. The method of treating a neurological condition in a subject in need thereof, according to claim 1, wherein the nucleic acid sequence encoding NeuroD1 transcription factor comprises a nucleic acid sequence selected from the group consisting of: a nucleic acid sequence encoding SEQ ID NO:2 or a functional fragment thereof; a nucleic acid sequence encoding SEQ ID NO:4 or a functional fragment thereof; SEQ ID NO:1 or a functional fragment thereof; SEQ ID NO:3 or a functional fragment thereof; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater identity to SEQ ID NO: 2 or SEQ ID NO: 4, or a functional fragment thereof.

3. The method of treating a neurological condition in a subject in need thereof, according to claim 1, wherein the reactive NG2 cells are present in the subject due to a neurological condition selected from the group consisting of: Alzheimer disease, Parkinson disease, amyotrophic lateral sclerosis (ALS), epilepsy, an injury to the central or peripheral nervous system, and stroke.

4. The method of treating a neurological condition in a subject in need thereof, according to claim 1, wherein administering a therapeutically effective dose of NeuroD1 transcription factor comprises local administration or systemic administration.

5. A method of treating a neurological condition in a subject in need thereof, comprising administering a therapeutically effective dose of a composition comprising an expression vector encoding NeuroD1 transcription factor to a NG2 cell of the subject.

6. The method of claim 5, wherein the expression vector is a viral expression vector.

7. The method of claim 6, wherein the expression vector is a retrovirus expression vector.

8. The method of claim 6, wherein the expression vector is an adeno-associated virus (AAV) expression vector.

9. The method of claim 5, wherein the neurological condition is characterized by loss of neurons and presence of reactive NG2 cells.

10. The method of claim 5, wherein the neurological condition is Alzheimer disease, Parkinson disease, amyotrophic lateral sclerosis (ALS), epilepsy, stroke or an injury to the central or peripheral nervous system.

11. The method of claim 5, wherein administering the NeuroD1 transcription factor comprises local administration.

12. The method of claim 11, wherein local administration comprises administration to the central nervous system.

13. The method of claim 11, wherein local administration comprises intracerebral injection, spinal cord injection, or injection into the cerebrospinal fluid.

14. The method of claim 5, wherein the subject is a human.

15. The method of claim 5, wherein administering the composition to the NG2 cell produces a neuronal phenotype in the NG2 cell thereby ameliorating the neurological condition of the subject.

16. The method of claim 15, wherein the neuronal phenotype comprises one or more of neuronal morphology, expression of one or more neuronal markers, electrophysiologic characteristics of neurons, synapse formation, and release of neurotransmitter.

17. The method of claim 15, wherein the neural phenotype is the expression of NeuN.

18. A method of treating a neurological condition in a human subject in need thereof, comprising administering a therapeutically effective dose of a composition comprising a viral expression vector encoding NeuroD1 transcription factor to a NG2 cell of the subject, wherein:
   administration comprises local administration to the central nervous system;
   the expression vector comprises a nucleotide sequence encoding an amino acid sequence having 95%, 96%, 97%, 98%, 99%, or greater sequence identity with the amino acid sequence set forth in SEQ ID NO: 2 or SEQ ID NO: 4, or a functional fragment thereof; and
   administering the composition to the NG2 cell produces a neuronal phenotype in the NG2 cell.

19. The method of claim 18, wherein the expression vector comprises a nucleotide sequence encoding the amino acid sequence set forth in SEQ ID NO: 2 or SEQ ID NO: 4.

* * * * *